United States Patent [19]

Gunther et al.

[11] Patent Number: 4,576,905

[45] Date of Patent: Mar. 18, 1986

[54] PHOTOGRAPHICALLY USEFUL CHALCOGENAZOLES, CHALCOGENAZOLINES, AND CHALCOGENAZOLINIUM AND CHALCOGENAZOLIUM SALTS

[75] Inventors: Wolfgang H. H. Gunther, Webster; Ronald E. Leone; Rosemary Przyklek, both of Rochester, all of N.Y.

[73] Assignee: Eastman Kodak Company, Rochester, N.Y.

[21] Appl. No.: 660,155

[22] Filed: Oct. 12, 1984

Related U.S. Application Data

[63] Continuation-in-part of Ser. No. 529,829, Sep. 6, 1983, abandoned.

[51] Int. Cl.[4] .......... G03C 1/34; G03C 1/28; G03C 1/02; G03C 5/24
[52] U.S. Cl. .......... 430/401; 430/428; 430/434; 430/446; 430/586; 430/598; 430/614; 430/600; 430/564; 430/584; 430/585; 430/587; 430/588; 430/589; 430/582; 430/583; 430/590; 430/592; 430/593; 430/594; 430/940; 430/517; 430/522; 548/100
[58] Field of Search .......... 430/598, 614, 600, 564, 430/584, 585, 940, 587, 588, 586, 589, 582, 428, 434, 401, 446, 583, 590, 517, 522, 593, 592, 594; 548/100; 260/239 R

[56] References Cited

U.S. PATENT DOCUMENTS

| | | |
|---|---|---|
| 2,168,174 | 8/1939 | Schlichting . |
| 2,323,503 | 7/1943 | Wilson . |
| 2,323,504 | 7/1943 | Wilson . |
| 2,339,094 | 1/1944 | Middleton . |
| 4,115,122 | 9/1978 | Adachi et al. .......... 430/598 |
| 4,121,935 | 10/1978 | Nishina et al. .......... 430/587 |
| 4,147,547 | 4/1979 | Koitabashi et al. .......... 430/584 |
| 4,272,614 | 6/1981 | Mifune et al. .......... 430/600 |
| 4,329,284 | 5/1982 | Detty et al. . |
| 4,365,016 | 12/1982 | Detty et al. . |
| 4,365,017 | 12/1982 | Detty et al. . |
| 4,451,557 | 5/1984 | Lok et al. .......... 430/600 |
| 4,471,044 | 9/1984 | Parton et al. .......... 430/598 |

FOREIGN PATENT DOCUMENTS 136420 of 1976 Japan .

OTHER PUBLICATIONS

Chem. Abst. vol. 100, 1984, 174729t (Mbuyi, et al.).
"Un Nouvel Heterocycle Tellure: le Benzisotellurazole-1,2", Campsteyn et al., *Journal of Heterocyclic Chemistry*, vol. 15, Aug. 1978, pp. 745–748.

*Primary Examiner*—Won H. Louie
*Attorney, Agent, or Firm*—Carl O. Thomas

[57] ABSTRACT

Compounds containing an aromatic ring portion fused with a tellurazolium or derivative tellurazole, tellurazoline (including tellurazolinylidene), or tellurazolinium ring portion are disclosed together with processes and intermediates for their preparation. With properly selected pendant groups these tellurazolium and derivative compounds can be usefully employed as dyes, antifoggants or stabilizers, nucleating agents, latent image keeping addenda, or speed or contrast altering addenda in silver halide photographic systems.

122 Claims, No Drawings

PHOTOGRAPHICALLY USEFUL CHALCOGENAZOLES, CHALCOGENAZOLINES, AND CHALCOGENAZOLINIUM AND CHALCOGENAZOLIUM SALTS

This application is a continuation-in-part of U.S. Ser. No. 529,829, filed Sept. 6, 1983, abandoned.

FIELD OF THE INVENTION

This invention is directed to certain novel aromatic chalcogenazoles, chalcogenazolines, and chalcogenazolinium and chalcogenazolium salts, to methods and intermediates for their preparation, to radiation sensitive silver halide emulsions and photographic elements containing these novel heterocyclic compounds, and to methods for producing images with the photographic elements.

BACKGROUND OF THE INVENTION

Aromatic chalcogenazolium salts, such as benzoxazolium, naphthoxazolium, benzothiazolium, naphthothiazolium, benzoselenazolium, and naphthoselenazolium salts, as well as their azole, azoline, and azolinium derivatives, have been widely employed in silver halide photography. These compounds have been employed as nuclei in polymethine dyes, antifoggants or stabilizers, nucleating agents, latent image keeping addenda, and speed or contrast increasing addenda for silver halide photographic systems.

Although Schlichting U.S. Pat. No. 2,168,174 and Wilson U.S. Pat. Nos. 2,323,503 and '504 have extended generic ring formulae to include tellurazoles as extrapolations of investigations of other chalcogenazoles, the true state of the art is summed up by Middleton U.S. Pat. No. 2,339,094:

It may be observed that the difficulty of reaction resulting in the production of azoles containing members of the oxygen group of elements in the azole ring may vary greatly with different elements, becoming greater in proceeding from the non-metallic elements such as oxygen and sulfur to the more strongly metallic elements such as selenium and tellurium. This probably accounts for the fact that many of the oxazoles and thiazoles have been known for years while the preparation of most of the selenazoles has been accomplished more recently and some of them are still unknown although the corresponding oxazoles and thiazoles are known. Furthermore, the tellurazoles from the simplest to the more complex derivatives have not been described up to the present time.

While the art has heretofore been unsuccessful in preparing tellurazolium salts and their derivatives, it should be noted that divalent tellurium atoms have been placed in other ring structures. Benzisotellurazole-1,2 is described in "Un Nouvel Heterocycle Tellure: le Benzisotellurazole-1,2", by Campsteyn et al, *Journal of Heterocyclic Chemistry*, Vol. 15, August 1978, pp. 745-748. Unfortunately no derivative of benzisotellurazole-1,2 is disclosed. Without a 3 position substituent the ring structure is itself severely restricted as a possible photographic addendum. Further, in general isochalcogenazoles are less desirable and more infrequently suggested for use as photographic addendum than the corresponding chalcogenazoles, since the chalcogen to nitrogen bond in the ring is a potential source of instability.

Tellurium atoms have been incorporated in ring structures other than azole or azine rings of various dyes. Japanese Kokai No. 136420, laid open Nov. 25, 1976, discloses a 1-tellura-3,5-cyclohexanedione nucleus in a merocyanine sensitizing dye in a silver halide emulsion. Detty et al U.S. Pat. No. 4,329,284 discloses 1,2-oxachalcogenol-1-ium salts, wherein the chalcogen can be tellurium or selenium, to be useful in photoconductive compositions. Detty et al U.S. Pat. Nos. 4,365,016 and '017 disclose tellurapyrylium dyes for use in photoconductive compositions.

SUMMARY OF THE INVENTION

This invention is directed to compounds containing an aromatic ring and, fused with the aromatic ring, a five membered ring containing a divalent tellurium atom, a nitrogen atom, and a carbon atom interposed between the tellurium and nitrogen atoms.

This invention is in one specific form directed to heterocyclic ammonium salts containing an aromatic ring and, fused with the aromatic ring, a tellurazolinium or tellurazolium ring containing a protonated or quaternized nitrogen atom.

This invention is also directed to processes for preparing protonated tellurazolium salts of the general formula

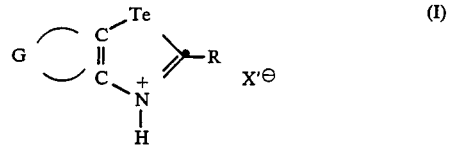

A first process for preparing a protonated tellurazolium salt satisfying the general formula (I) comprises reacting a starting material of the formula

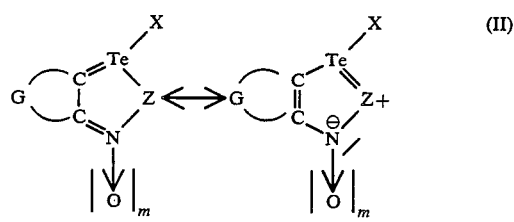

with a strong alkaline reducing agent, acylating with a compound of the formula

treating with a strong nonoxidizing acid, wherein
G represents the atoms completing a fused aromatic nucleus,
R is an optionally substituted hydrocarbon moiety,
m is zero or 1,
X is halogen or pseudohalogen,
X' is an anion,
Y is halogen or R—C(O)—O—,
Z is —O— or —N(R')—, and
R' is an aromatic nucleus.

This invention is additionally directed to a second process for preparing a protonated tellurazolium salt satisfying general formula (I) comprising reacting a starting material of the formula

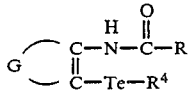 (IV)

with phosphoryl chloride or bromide wherein:
G represents the atoms completing an aromatic nucleus,
R represents hydrogen, an optionally substituted hydrocarbon moiety, or a —C(O)M group, wherein M is chosen to complete an acid, ester, thioester, or salt,
$R^4$ represents a leaving group, and
X' is an anion.

This invention is also directed to a third process for preparing a protonated tellurazolium salt satisfying general formula (I) comprising reacting a starting material of the formula

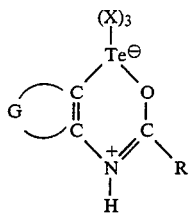 (V)

with a strong alkaline reducing agent, and
treating with a strong nonoxidizing acid, wherein
G represents the atoms completing a fused aromatic nucleus,
R represents an aliphatic or aromatic group comprised of a hydrocarbon moiety optionally linked through a divalent oxy, thio, or carbonyl linkage, an amino group, an amido group, ureido group, a formamidine disulfide group, or a —C(O)M group, wherein M is chosen to complete an acid, ester, thioester, or salt,
X represents halogen or pseudohalogen, and
X' represents an anion.

This invention is further directed to preparing a compound according to formula (V) comprising reacting

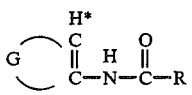 (VI)

with TeX₄ at an elevated temperature, wherein:
H* is an activated hydrogen atom,
G represents the atoms completing an aromatic nucleus,
R represents an aliphatic or aromatic group comprised of a hydrocarbon moiety optionally linked through a divalent oxy, thio, or carbonyl linkage, an amino group, an amido group, a ureido group, a formamidine disulfide group, or a —C(O)M group, wherein M is chosen to complete an acid, ester, thioester, or salt, and
X represents chlorine or bromine atoms.

This invention is also directed to converting a protonated azolium compound satisfying general formula (I) to an azole compound of the formula

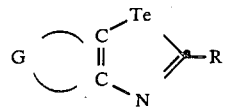 (VII)

by treating with a base.

This invention is further directed to a process of converting to a heterocyclic quaternary ammonium salt an azole compound according to formula (VII) by reacting the azole compound with a quaternizing agent.

This invention is still further directed to preparing a quaternary ammonium salt of the formula

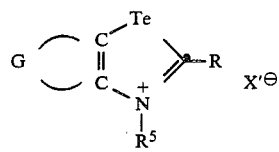 (VIII)

comprising reacting a starting material of the formula

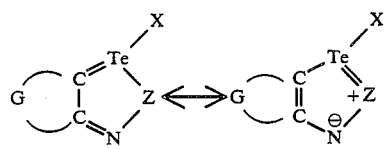 (IX)

with a strong alkaline reducing agent,
treating with an aldehyde,
treating with a second strong reducing agent,
acylating with a compound according to formula (III), and
treating with a strong nonoxidizing acid, wherein
G represents the atoms completing a fused aromatic nucleus,
R is an optionally substituted hydrocarbon moiety,
$R^5$ is an optionally substituted hydrocarbon residue of said aldehyde,
X is chloride, bromide, or iodide,
X' is an anion,
Y is halogen or R—C(O)—O—.
Z is —O— or —N(R')—, and
R' is an aromatic nucleus, This invention is also directed to compounds containing an aromatic ring and, fused with the aromatic ring, a five or six membered ring containing a tellurium atom, a nitrogen atom, and an oxygen atom bonded to the tellurium atom and interposed between the tellurium and nitrogen atoms.

This invention is additionally directed to a dye containing at least one basic nucleus comprised of an aromatic ring and a fused tellurazolium ring.

This invention is still additionally directed to a radiation sensitive silver halide emulsion comprised of
a dispersing medium,
radiation sensitive silver halide grains, and
a photographically useful concentration of an addendum containing an aromatic ring and, fused with said aromatic ring, a five membered ring containing a divalent tellurium atom, a nitrogen atom, and a carbon atom interposed between said tellurium and nitrogen atoms.

This invention is still further directed to an improvement in a photographic element comprised of a support,
coated on the support, at least one silver halide emulsion layer comprised of
a dispersing medium and
radiation-sensitive silver halide grains, and
located to facilitate photographic image formation, an addendum comprised of a chalcogenazole, chalcogenazoline, chalcogenazolinium, or chalcogenazolium heterocyclic ring fused with an aromatic ring,
wherein tellurium is a member of the heterocyclic ring.

Finally, this invention is directed to a process of producing a viewable photographic image comprising photographically processing an imagewise exposed photographic element as described above.

Tellurazolium salts and their derivatives have been long postulated, but sought without success. The present invention for the first time provides the art with aromatic tellurazolium salts as well as their tellurazole, tellurazoline, and tellurazolinium derivatives and processes and intermediates for their preparation.

These aromatic ring structures are, quite unexpectedly, highly stable and therefore can be usefully employed as photographic addenda in place of corresponding nuclei containing other chalcogens, often with unexpectedly advantageous results. When so employed the compounds of this invention are useful as dyes, antifoggants and stabilizers, nucleating agents, latent image keeping addenda, and speed or contrast altering addenda.

When in the form of polymethine dyes, particularly cyanine dyes, the compounds of this invention exhibit heretofore unrealized advantages. In polymethine sensitizing dyes electromagnetic radiation absorption maxima are shifted bathochromically as the number of methine linking groups is increased. Unfortunately, dye desensitization also tends to increase as a function of the number of methine linking groups. It is known that a bathochromic shift in absorption maxima of up to 5 nm per nucleus can be realized when a selenium atom is substituted for a sulfur atom in a chalcogenazolium dye nucleus. Thus, with a symmetrical simple cyanine dye a bathochromic shift of the absorption peak of up to 10 nm can be realized by substituting selenium for sulfur in both nuclei.

It has now been discovered that the substitution of tellurium for sulfur in a chalcogenazolium dye nuycleus is typically capable of producing a bathochromic shift in absorption of 25 nm or more. This can allow a reduction in the number of methine linking groups needed to achieve a selected absorption peak which reduces dye bulk and can reduce dye desensitization. For example, in a simple symmetrical cyanine dye the inclusion of two nuclei containing tellurium can result in a 50 nm or more bathochromic shift in the absorption maximum as compared to that of a corresponding dye containing sulfur in place of tellurium. Thus, although the compounds of this invention can take the form of dyes having absorption peaks ranging from the ultraviolet, through the blue, green, and red portions of the visible spectrum, and into the infrared, the dyes are increasingly attractive as the absorption maxima are shifted bathochromically. Preferred dyes according to this invention are therefore those capable of spectral sensitization in the minus blue (greater than 500 nm) portion of the visible spectrum and in the infrared portion of the spectrum.

It has also been discovered that relatively high extinction coefficients are realized with the dyes of the present invention. This can be advantageous in allowing lower levels of dye to be employed to achieve a desired level of radiation absorption. When adsorbed to silver halide grain surfaces, the dyes of the present invention are useful not only as sensitizers, but also for altering native or intrinsic sensitivity. When not adsorbed to silver halide grain surfaces, the dyes of this invention can function in the emulsion and other layers of photographic elements as inter-grain absorbing, antihalation, and filter dyes.

DESCRIPTION OF PREFERRED EMBODIMENTS

Photographically useful compounds according to this invention contain an aromatic ring portion and, fused with the aromatic ring portion, a five membered ring containing a divalent tellurium atom, a nitrogen, and a carbon atom interposed between the tellurium and nitrogen atoms. From this general description it is apparent that these compounds can form four possible divalent tellurium atom containing ring structures, depending upon ring unsaturation and bonding to the nitrogen atom. These ring structures are tellurazole, tellurazoline (including tellurazolinylidene when the interposed carbon atom is doubly bonded to a single substituent), and, when the nitrogen atom is protonated or quaternized, tellurazolinium and tellurazolium ring structures.

The aromatic ring portion facilitates synthesis of the five membered ring portion with which it is fused. The five membered ring portion is highly stable and should, by analogy to corresponding chalcogen containing heterocycles, be highly stable, once formed, with or without a fused aromatic ring portion. Therefore, compounds lacking a fused aromatic ring portion should offer performance characteristics which are generally equivalent to those of the photographically useful compounds of this invention.

Procedures for synthesizing the photographically useful compounds according to this invention satisfying the above general description, not having been previously known to the art, also constitute subject matter of the present invention. One useful synthetic route is to prepare a protonated tellurazolium salt, such as illustrated by general formula (I) above. The tellurazolium salt can be deprotonated by treatment with a base to form the corresponding tellurazole. The tellurazole can be converted to the corresponding tellurazoline by a conventional 2,3-addition reaction. A quaternizing agent can be employed to convert the tellurazole or tellurazoline to the corresponding quaternized tellurazolium or tellurazolinium salt. When the five membered tellurazolium ring is substituted at its 2-position (i.e., at the interposed carbon atom), conventional procedures can be employed to prepare a polymethine dye containing a tellurazolium nucleus linked chromophorically through its 2-position. In such a polymethine dye the tellurazolium ring is recognized to constitute one resonance extreme while a tellurazolinylidene ring constitutes another resonance extreme. Thus, it is apparent that the preparation procedures of the present invention are capable of producing compounds containing tellurazolium and derivative tellurazole, tellurazoline (including tellurazolinylidene), and tellurazolinium ring portions.

The first process according to this invention for preparing a protonated tellurazolium salt satisfying formula (I) described above employs a starting material satisfying formula (II). When m is zero and Z is —N(R')—, the starting material can be (2-phenylazophenyl-C,N')tellurium(II) chloride, the preparation of which is described by Cobbledick et al, "Some New Organotellurium Compounds Derived from Azobenzene: The Crystal and Molecular Structure of (2-Phenylazophenyl-C,N')tellurium(II) Chloride", *Journal of Chemical Research*, pp. 1901–1924, 1979. Although Cobbledick et al employed chloride as the halogen corresponding to X in formula (II), it is apparent from the reported synthesis that X can be halogen (employed here and elsewhere to designate generically chloride, bromide, or iodide) or a pseudohalogen (i.e., one of the recognized class of substituents known to approximate the substituent properties of halogen), such as a cyano, thiocyanate, or hydroxy substituent. Similarly, G and R' can be varied merely by substituting for one or both of the phenyl groups employed in the phenylazophenyl employed by Cobbledick et al an alternative aromatic nucleus. In general the aromatic nuclei, which form G in each of its various occurrences and are referred to in other occurrences variously as aromatic rings, nuclei, or aryl groups or moieties, are preferably carbocyclic aromatic nuclei having from 6 to 20 carbon atoms, most preferably a phenyl or naphthyl or, in the fused form, a benzo or naphtho, nucleus. In some instances an aromatic nucleus can be fused through a five-membered ring, as is illustrated by acenaphthylene fused at its 1,2 ring edge. Since R' has little influence on the reaction and is not incorporated in the final product, R' can take a particularly wide variety of aromatic forms, but is generally most conveniently chosen from among the preferred forms of carbocyclic aromatic nuclei.

In an alternative form the first process can employ a starting material according to formula (II) in which m is zero and Z is oxygen. This compound, which is a novel compound according to this invention, can be formed by placing in solution an optionally substituted α-tetralone, hydrochloric or hydrobromic acid, tellurium dioxide, and hydroxylamine. This reaction has the advantage that all of the required materials are readily available at relatively low cost. Alcohols are convenient solvents for the reaction, although other nonreactive organic solvents can be employed. Heating is not required, but can accelerate the reaction. The material of formula (II) forms a solid phase which can be separated by routine filtering and washing steps. Both unsubstituted α-tetralone and various substituted derivatives are useful. Preferred α-tetralones can be represented by the formula:

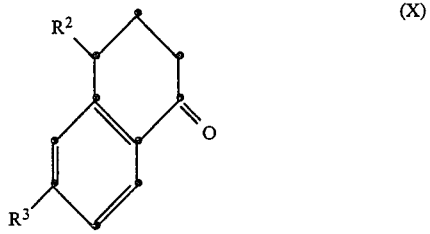

(X)

wherein $R^2$ and $R^3$ are independently selected from among hydrogen, halogen, alkyl, and alkoxy. Since $R^2$ and $R^3$ are naphtho ring substituents in the tellurazolium salt ultimately produced, it is apparent that the number of carbon atoms in the alkyl and alkoxy substituents can be widely varied. Instead of employing an α-tetralone, as described above, it is possible to employ a substituted or unsubstituted acenaphthen-1-one.

In general alkyl substituents and moieties of the tellurazolium salts and their derivatives are limited only by physical considerations, such as solubility, mobility, and molecular bulk. Generally alkyl and other aliphatic moieties of the tellurazolium salts and their derivatives of this invention are contemplated to contain up to 18 or more carbon atoms. Since increasing molecular bulk, except as sometimes required to reduce mobility, is seldom desirable in photographic applications, the preferred aliphatic hydrocarbon moieties contain up to 6 carbon atoms, with the lower alkyls (i.e., methyl, ethyl, propyl, and butyl) being preferred. In general, references to cycloalkyl indicate groups having 4 to 10 carbon atoms in a ring, with 5 or 6 ring carbon atoms being preferred.

Instead of preparing the starting material of formula (II) wherein m is zero and Z is oxygen in the manner described above, an oxime of an α-tetralone or acenaphthen-1-one described above can be reacted with tellurium tetrahalide, preferably tellurium tetrachloride or tellurium tetrabromide. In this and subsequent descriptions of employing tellurium tetrahalides as reactants it should be borne in mind that similar results can usually be obtained by reacting, before or during the α-tetralone or acenaphthen-1-one or reaction, a soluble halide salt, such as an alkali or alkaline earth halide, with tellurium dioxide. This is believed to generate a tellurium tetrahalide. A carboxylic acid can be employed as a solvent for the reaction, and the reaction can be accelerated by heating. The starting material of formula (II) forms a solid phase which can be separated by routine filtering and washing procedures. The preferred α-tetralone oximes correspond to the preferred α-tetralones and can be represented by the formula:

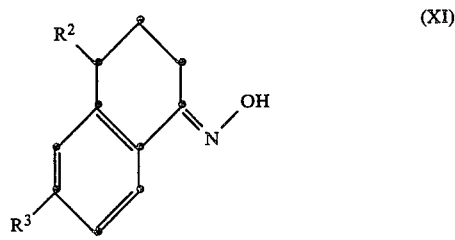

(XI)

wherein $R^2$ and $R^3$ are chosen as described above.

In a third general form of the starting material of formula (II) m can be 1 and Z oxygen. This form of the starting material of formula (II), which also is a novel compound according to this invention, can be prepared by reacting with tellurium tetrahalide a carbocyclic aromatic compound activated for electrophilic substitution. Although naphthalene is illustrative of a fused ring carbocyclic aromatic compound that has been activated for electrophilic substitution, it is generally easiest to activate benzene. Activation can be achieved by employing electron donating substituents, such as hydroxy, hydroxyalkyl, alkyl, alkoxy, aryloxy, hydroxyaryl, amino, and groups of similar negative Hammett sigma values, singly or in combination. The reaction can be carried out in an organic solvent such as a liquid hydrocarbon (e.g., benzene or cyclohexane), a halohydrocarbon (e.g., chlorobenzene or chloroform), a nitrohydrocarbon (e.g., nitromethane), or acetonitrile while heating to reflux. Formation of the starting material of formula (II) can be completed by nitrating and then treating with a reducing agent. Strong reducing agents can be employed in precisely stoichiometric concentrations or less. It is generally preferred to employ a mild or dilute reducing agent. Nitric acid in a suitable diluent, such as water or carboxylic acid, can be used for nitrating while hypophosphorous acid can be employed as the mild reducing agent. The synthetic route described above can be modified by a preliminary treatment with the mild reducing agent before nitrating and employing a strong nonoxidizing acid after nitrating and before employing the mild reducing agent a second time. In general the strong nonoxidizing acids contemplated for use in this and other steps of the preparation procedures herein described include acids such as hydrochloric acid, hydrobromic acid, sulfuric acid, fluoroboric acid, a sulfonic acid, and phosphoric acid.

A particularly preferred starting material, which constitutes a novel compound according to this invention, prepared by the process described in the preceding paragraph can be represented by the formula:

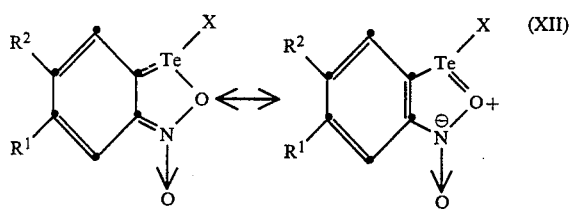

(XII)

wherein at least one of $R^1$ and $R^2$ and preferably both are chosen from among hydroxy, hydroxyalkyl, alkyl, alkoxy, aryloxy, hydroxyaryl, and amino groups. Alternately $R^1$ and $R^2$ together can form an alkanediyldioxy linkage—e.g., a —O—$(CH_2)_n$—O— linkage, where n is preferably from 1 to 3. X is halogen or pseudohalogen, as previously described.

Once the starting material of formula (II) has been prepared, regardless of the choice of alternative preparation routes described above, it is treated with a strong alkaline reducing agent, such as an alkali borohydride (e.g., lithium, sodium, or potassium borohydride). The reaction product is then acylated with a compound according to formula (III). From the values of Y identified above, it is apparent that the acylating agent can be either acyl halide, such as acetyl chloride or acetyl bromide, or an acid anhydride, such as acetic anhydride. By noting the appearance of R in formulas (I) and (III) it is also apparent that the acyl halide or acid anhydride also provides the 2-position substituent in the protonated tellurazolium salt formed as an ultimate product. The R group serves the important purpose of providing a favored reaction site on the tellurazolium ring of the salt ultimately produced. Generally this function is adequately served when R is a methyl group, but a wide variety of alternatives can be generated readily, if desired. When the acylating agent is acetyl halide or acetic anhydride, the 2-position substituent is methyl. By varying the acyl halide or acid anhydride employed, the 2-position substituent of the tellurazolium salt can take the form of various hydrocarbon moieties, such as alkyl, cycloalkyl, alkaryl, aryl, aralkyl, and various substituted derivatives, such as those containing alkoxy, alkylthio, halo, amino, amido, and similar substituents.

Though not isolated, it is believed that acylation according to this invention produces tellurazolines. To avoid opening of the tellurium containing ring, the additional step of producing the stable corresponding protonated tellurazolium salt is undertaken by treatment with a strong nonoxidizing acid, such as any of those mentioned above.

The second process for preparing protonated tellurazolium salts according to formula (I) allows a somewhat more general selection of R or 2-position ring substituents as compared to the first process. The starting material employed for this process is represented by formula (IV). When the second process is employed, R in the starting material of formula (IV) and the protonated tellurazolium salt prepared satisfying formula (I) can include in addition to any of the optionally substituted hydrocarbon moieties discussed above in connection with the first process hydrogen or a —C(O)M group, wherein M is chosen to complete an acid, ester, thioester, or salt (e.g., —C(O)OH, —C(O)OCH$_3$, —C(O)SCH$_3$, or —C(O)ONa). When M completes an ester or thioester, the esterifying moiety can take any of the hydrocarbon or substituted hydrocarbon form(s) previously described by reference to R.

$R^4$ in formula (IV) forms no part of the protonated tellurazolium salt ultimately produced. Thus, $R^4$ can take the form of any convenient group that can be displaced upon treatment with phosphoryl chloride to permit ring closure. Treatment with phosphoryl chloride eliminates Cl—$R^4$. Thus, any group that can be eliminated as the chloride can be chosen as the leaving group. For example, $R^4$ can be chosen from among the same hydrocarbon moieties described above in connection with R. Since $R^4$ forms no part of the protonated tellurazolium salt ultimately produced, it is generally most convenient to select $R^4$ from among lower alkyl substituents.

The starting material of formula (IV) can be prepared from known tellurium compounds by several alternative procedures. One preferred approach is to start with a compound according to formula (II) in which m is zero and Z is —N(R')—, as previously described. This compound is treated with a strong alkaline reducing agent, such as previously described. Thereafter, acylation is performed using an acylating agent according to formula (III), as previously described. This produces the material of formula (IV). To produce the starting material of formula (IV) by another procedure, after treating with a strong alkaline reducing agent, the reaction product is reacted with X—$R^4$, where X is halide, and then acylated with formic acid. In this instance R in formula (IV) is hydrogen. By employing other acylating agents R can take any one of the other forms of formula (IV).

A third process for preparing a protonated tellurazolium salt according to formula (I) comprises employing a starting material according to formula (V), which additionally constitutes a novel compound according to this invention. X in formula (V) can be halogen or pseudohalogen, as previously described. R in the starting material of formula (V) can take an even greater variety of forms than described above in connection with formula (IV). R in the starting material of formula (V) and the protonated tellurazolium salt prepared satisfying formula (I) can include an aliphatic or aromatic group comprised of a hydrocarbon moiety (e.g., alkyl, aryl, alkaryl, or aralkyl moiety) optionally linked through a divalent oxy, thio, or carbonyl linkage (e.g., an alkoxy, aryloxy, alkaryloxy, aralkyloxy, alkylthio, arylthio, alkarylthio, aralkylthio, or acyl moiety);

an amino group, including primary, secondary and tertiary amines; an amido group (e.g., acetamido and butyramido); a ureido group (e.g., 1-ureido, 3-phenyl-1-ureido, and 3-methyl-1-ureido); a formamidine disulfide group (e.g., formamidine disulfide and N'-ethyl-N'-methyl-$\alpha,\alpha'$-dithiobisformamidine groups); or a —C(O)M group, wherein M is chosen to complete an acid, ester, thioester, or salt (e.g., —C(O)OH, —C(O)OCH$_3$, —C(O)SCH$_3$, or —C(O)ONa). The starting material is reacted with a strong alkaline reducing agent, such as described above, and the resulting product is reacted with a strong nonoxidizing acid, such as also described above, to produce the desired protonated tellurazolium salt. By suitable treatment, (e.g., reduction or hydrolysis), the formamidine disulfide can, if desired, be converted to a thioureido group once the protonated tellurazolium salt has been formed. (The structure of formamidine disulfide is described in *International Union of Pure and Applied Chemistry, Nomenclature of Organic Chemistry*, Buttersworth, Longon, 1965, Section 951.5.) When R is a primary amino group, it is in fact in one tautomeric form an imino group, which provides a highly convenient starting material for the synthesis of azacyanine dyes.

Both the starting material of formula (V) and the process for its preparation form a part of the present invention. When the compound of formula (VI) is melted or heated in a suitable solvent (e.g., acetonitrile, butyronitrile, or chloroform) with tellurium tetrachloride or tellurium tetrabromide, the material of formula (V) is produced. Heating to a temperature of at least 60° C. up to about 140° C. is contemplated, with temperatures of from about 110° to 120° C. being preferred. In part the reaction to produce the material of formula (V) is accomplished by choosing G in formula (VI) so that the aromatic nucleus which it completes is activated in the position ortho to the amido substituent. This can be accomplished by including in the aromatic nucleus one or more substituents capable of directing ring substitution in formula (VI) to the ring position of the starred activated hydrogen atom. For carbocyclic aromatic rings, such as benzene and naphthene rings, useful substituents can be chosen from among aliphatic and aromatic groups comprised of hydrocarbon moieties (e.g., alkyl, aryl, alkaryl, or alkaryl) optionally linked through a divalent oxygen or sulfur atom (e.g., an alkoxy, aryloxy, alkaryloxy, alkaryloxy, alkylthio, arylthio, alkarylthio, or alkarylthio group); an amino group, including primary, secondary and tertiary amines; an amido group (e.g., acetamido and butyramido); a sulfonamido group (e.g. an alkyl or arylsulfonamido group); a sulfamoyl group (e.g. an alkyl or arylsulfamoyl group); a ureido group (e.g., 1-ureido, 3-phenyl-1-ureido, and 3-methyl-1-ureido); a thioureido group (e.g., a thioureido group corresponding to the above exemplary ureido groups); hydroxy; or a —C(O)M group or —S(O)$_2$M group, wherein M is chosen to complete an acid, ester, thioester, or salt (e.g., —C(O)OH, —C(O)SCH$_3$, —C(O)OCH$_3$, —C(O)ONa, —S(O)$_2$OH, —S(O)$_2$OCH$_2$C$_6$H$_5$, or —S(O)$_2$OLi). The aromatic nucleus completed by G as well as R can progress unaltered from the compound of formula (VI) to the protonated tellurazolium salt forming the protonated tellurazolium salt ultimate product.

The anion X' shown associated with the protonated tellurazolium salt in formula (I) is usually the anion of the last acid employed in the process. However, it is apparent that conversion from one anion to another can be easily accomplished and that the anion of the tetrazolium salts of this invention can be varied widely.

To obtain the tellurazole corresponding to the protonated tellurazolium salt prepared as described above treatment with a base, such as ammonium hydroxide, an alkali hydroxide, or an alkali carbonate or bicarbonate, can be undertaken. Procedures for performing the same operation on known chalcogenazolium salts are directly applicable. The tellurazole product obtained is generally indicated by formula (VII) above wherein G and R correspond to their values in the parent protonated tellurazolium salt.

To convert the tellurazole of formula (VII) to a corresponding quaternized heterocyclic ammonium salt, as indicated by formula (VIII), the tellurazole of formula (VII) is reacted with a quaternizing agent. In a preferred form the quaternizing agent is a sulfonic acid ester containing the quaternizing radical $R^5$ as the base derived moiety of the ester. Specifically preferred quaternizing agents are strong quaternizing agents, such as poly(fluoro)alkylsulfonic acid esters, such as aryl, alkenyl, alkynyl, aralkyl, or alkaryl esters of poly(fluoro)alkylsulfonic acid. Perfluorinated alkylsulfonic acid esters are particularly preferred quaternizing agents (e.g., trifluoromethylsulfonic acid esters). Arylsulfonic acid esters, such as para-toluenesulfonic acid esters, are also strong quaternizing agents. 1,3,2-Dioxathiane-2,2-dioxide and 1,3,2-dioxathiolane-2,2-dioxide have also been demonstrated to be useful quaternizing agents. Including electron donating ring substituents in the aromatic nuclei forming G in formula (VII) facilitates quaternization while strongly electron withdrawing substituents require strong quaternizing agents to be employed when quaternization occurs after tellurazole ring formation.

A very advantageous approach for preparing quaternized tellurazolium salts according to formula (VIII) is to employ a starting material according to formula (II) wherein m is zero, indicated specifically by formula (IX). The starting material is first treated with a strong alkaline reducing agent, which can be selected from among those described above. The reaction product is then treated with an oxidizing agent, such as oxygen, a peroxide, a disulfide, or a sulfoxide, to produce

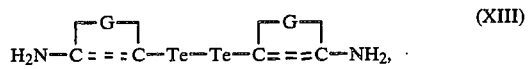 (XIII)

which is treated with an aldehyde, treated with a strong alkaline reducing agent, such as described above, and then treated with an acylating agent according to formula (III), as described above, and a strong nonoxidizing acid, also as described above. Although treatment with an oxidizing agent is preferred, no separate oxidizing step is required. Ambient air will spontaneously perform such oxidation, and treatment with the aldehyde is sufficient in an inert atmosphere. A variety of quaternizing substituents can be introduced in the salt of formula (VIII) in addition to those provided by strong quaternizing agents, merely by appropriate selection of the aldehyde. Thus, $R^5$ in formula (VIII) can take the form of an optionally substituted hydrocarbon residue of an aldehyde quaternizing substituent, such as alkyl, alkenyl, alkynyl, or aralkyl moieties as well as substituted derivatives, such as oxy, thio, sulfo, sulfonyl, sulfato, halo, or carboxy substituted derivatives, often incorporated to modify solubility or other physical properties. Sulfoalkyl and sulfatoalkyl quaternizing substituents having from 1 to 6 carbon atoms are specifically preferred.

In the foregoing discussion the novel compounds of formulae (II), (V), (IX), and (XII) have been described in terms of their utility as starting materials for the preparation of tellurium, nitrogen, and carbon containing ring structures. It should be recognized, however, that these formulae represent specific illustrations of a novel class of cyclic compounds containing tellurium, nitrogen, carbon, and oxygen in the ring structures. The cyclic compounds of this class according to the present invention can be characterized as containing an aromatic ring and, fused with the aromatic ring, a five or six membered ring containing a tellurium atom, a nitrogen atom, and an oxygen atom bonded to the tellurium atom and interposed between the tellurium and nitrogen atoms. From the formulae, it is apparent that the tellurium atom is preferably in either a tetravalent or hexavalent form, and the nitrogen atom is in either a trivalent or pentavalent form.

In a form in which the heterocyclic tellurium containing ring is a five membered ring and the ring nitrogen atom is trivalent, these novel compounds can take the form of 1,2,5-oxatellurazoles which contain an aromatic ring. Specific examples of such compounds are substituted and unsubstituted 2,1,3-benzoxatellurazoles and naphth[2,1-c]-1,2,5-oxatellurazoles. When the nitrogen atom is in a pentavalent form, the compounds can take the form of corresponding N-oxides—e.g., substituted and unsubstituted 2,1,3-benzoxatellurazole-N-oxides and naphth[2,1-c]-1,2,5-oxatellurazole-N-oxides.

In a form in which the heterocyclic tellurium containing ring is a six membered ring, these novel compounds can take the form of 1,2,5-oxatellurazinium salts which contain a fused aromatic ring. Specific examples of such compounds are substituted and unsubstituted 2,1,4-benzoxatellurazinium and naphth[2,1-c]-1,2,5-oxatellurazinium salts.

The ring substituents described in connection with formulae (II), (V), (IX), and (XII) are those preferred for the applications in which these compounds are employed as starting materials in the syntheses described. However, it is apparent that ring substituents can be chosen from among those known for chalcogenazole and chalcogenazolium nuclei to satisfy other specific applications. For example, electron withdrawing substituents other than halogen and pseudohalogen can be present. In addition to being useful intermediates for the syntheses described above, the compounds of this invention containing tellurium, nitrogen, and oxygen atoms in a five or six membered ring can be applied to uses as ultraviolet and visible electromagnetic radiation absorbers.

From the foregoing discussion of synthetic discoveries it is apparent that this invention is in general capable of providing tellurium analogues of the chalcogenazolium salts and their chalcogenazole, chalcogenazoline, and chalcogenazolinium derivatives heretofore known to be useful, particularly those known to be useful in the photographic art. Of particular importance to the preparation of photographically useful polymethine dyes as well as of certain nucleating agent, latent image keeping addenda, and speed or contrast altering addenda is the capability of the processes of this invention to produce compounds substituted in the 2 and 3 positions—that is, the 2-position ring carbon atom and the nitrogen atom—of the divalent tellurium containing ring. A 2-position substituent is essential to providing a favored reaction site on the tellurium containing ring. Contemplated 2-position substituents can be linked to the 2-position ring carbon atom by a single or double carbon to carbon, carbon to nitrogen, or carbon to chalcogen bond. Carbon to carbon double and single bonding is highly useful in forming polymethine dyes containing a methine linkage in the 2-position. Carbon to nitrogen single and double bonds are useful in the 2-position are useful in preparing azacyanine polymethine dyes and in preparing azo dyes incorporating the tellurium containing ring as a portion of the chromophore. Chalcogen single and double bonds in the 2-position provide conveniently addressed reaction sites.

Once formed, the tellurazolium salts of this invention and their tellurazole, tellurazoline, and tellurazolinium derivatives were discovered to form unexpectedly stable heterocyclic nuclei which can thereafter be synthetically modified by synthetic procedures generally applicable to known chalcogen analogues. These procedures, which are well known in the art, are adequately illustrated by the examples.

While the tellurazolium and derivative tellurazole, tellurazoline, and tellurazolinium compounds of this invention can be applied, with or without substituent adaptations, to a variety of known applications for corresponding compounds incorporating a differing divalent chalcogen atom, this invention is particularly directed to applying the tellurazolium and derivative compounds to photographic uses, particularly uses in silver halide photography.

In its most widely employed form silver halide photography employs for imaging radiation sensitive silver halide grains. The grains are suspended in a dispersing medium so that the grains and dispersing medium together form a radiation sensitive silver halide emulsion. The silver halide emulsions are typically coated on a photohgraphic film or paper support to form a photographic element. A simple photographic element can consist of a support and an emulsion layer; however, typically additional layers, such as multiple emulsion layers, subbing layers, interlayers, and overcoats are also present. The silver halide emulsions can be usefully, though incompletely, categorized as those which form predominantly surface or predominantly internal latent images upon exposure. Photographic elements can be conveniently classified as being direct positive photographic elements or negative working photographic elements. Whether a positive or negative viewable image is produced is a function of both the emulsion chosen and the photographic processing undertaken. Although light processing is known and employed for specialized applications, in most instances photographic processing to produce a viewable image is accomplished by development of an imagewise exposed photographic element in an aqueous alkaline processing solution. Usually internal latent image forming emulsions are employed in combination with uniform light exposure or, preferably a nucleating agent, to produce direct positive images. Direct positive images can be produced also by employing initially surface fogged silver halide grains which rely on selective development of unexposed grains to produce direct positive images. Internal latent image emulsions can be used to produce negative images by internal development—that is, developing in the presence of iodide ion or a silver halide solvent capable of rendering the internal latent image site accessible to the developing agent. Aside from solarization effects, surface latent image emulsions cannot produce direct positive images, but are extensively used to produce positive color images by reversal processing. Of extreme importance to obtaining commercially attractive photographic images are a large variety of emulsion, photographic element, and processing solution addenda. A succinct summary of radiation sensitive silver halide emulsions, photographic elements, processing solutions, their basic and modifying components, and significant patents and publications describing their features is contained in *Research Disclosure*, Vol. 176, December 1978, Item 17643. *Research Disclosure* and *Product Licensing Index* are publications of Kenneth Mason Publications Limited; Emsworth; Hampshire P010 7DD; United Kingdom.

In a specifically contemplated photographically useful form a compound according to the present invention can constitute a dye containing at least one basic nucleus comprised of an aromatic ring and a fused tellurazolium ring. The tellurazolium ring preferably forms a part of the chromophore so that it is in the form of a tellurazolium ring in one resonance extreme and rearranges to a tellurazolinylidene ring in a second resonance extreme. When the protonated tellurazolium salts are as described above with R being amine, a corresponding diazo dye can be generated including the novel ring structure of this invention as a part of the dye chromophore.

In a specifically preferred form the dyes of this invention are polymethine dyes. Such dyes include cyanine and merocyanine dyes. The dyes can contain two nuclei joined through a methine linkage, which is the most common occurrence. These dyes are sometimes referred to as simple cyanines or merocyanines to distinguish them from those containing three or more nuclei, referred to as complex cyanine or merocyanine dyes. In addition to the above, the polymethine dyes of this invention can take the form of hemicyanine, styryl, neocyanine, azacyanine, and allopolarcyanine dyes. Such dyes according to the invention are direct analogues of conventional dyes in these classes, the difference being the presence of a divalent tellurium atom in at least one chalcogenazolium nucleus in place of another divalent chalcogen.

In a specifically preferred form the dyes according to the present invention are cyanine dyes. These dyes can be symmetrical, thereby including at least two identical tellurazolium nuclei according to this invention, or asymmetrical, in which instance the nuclei can each be different tellurazolium nuclei according to this invention or can be a combination of at least one tellurazolium nucleus according to this invention together with one or more conventional basic heterocyclic cyanine dye nuclei. The nuclei are joined through a methine linkage, which can consist of a single methine group or a chain of methine groups. As discussed above, since the tellurazolium ring is capable of producing a bathochromic absorption shift, a lesser number of methine groups can be employed to achieve absorption of longer wavelength electromagnetic radiation; however, methine linkages of up to 13 or more successive methine groups can be incorporated in the dyes, if desired.

One preferred class of cyanine dyes according to this invention can be represented by the following formula:

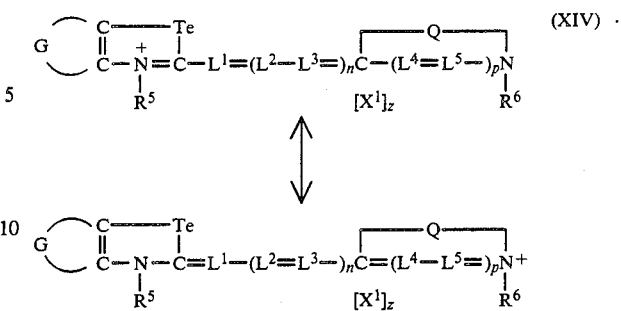

wherein
G represents the atoms completing a fused aromatic nucleus;
$L^1$, $L^2$, $L^3$, $L^4$, and $L^5$ each independently represent a methine group;
n represents zero, 1, or 2;
p represents zero or 1;
Q represents the atoms completing a basic azolinylidene or azinylidene heterocyclic nucleus;
$R^5$ and $R^6$ each independently represent a quaternizing substituent;
$X^1$ represents a counterion, and
z is zero or a positive integer chosen to balance ionic charge.

From the foregoing formula it is apparent that the cyanine dye is a species of the quaternized tellurazolium salt of formula (VIII) wherein the 2-position substituent R has been further elaborated. The tellurazolium nucleus has already been discussed above. Although this nucleus could be characterized as either a tellurazolium or tellurazolinylidene nucleus, for convenience the former nucleus designation is employed while for consistency the remaining nucleus is referred to as an azolinylidene or azinylidene nucleus.

Generally any azolinylidene or azinylidene nucleus satisfying formula (XIV) can be employed in combination with the novel tellurazolium nucleus. It is specifically contemplated that Q can be chosen from among benzotellurazolinylidene, naphthotellurazolinylidene, 2- or 4-pyridylidene, imidazopyridylidene, 2- or 4-quinolinylidene, 1- or 3-isoquinolinylidene, benzoquinolinylidene, thiazoloquinolylidene, imidazoquinolylidene, 3H-indolylidene, 1H or 3H-benzindolylidene, oxazolinylidene, oxazolidinylidene, benzoxazolinylidene, naphthoxazolinylidene, oxadiazolinylidene, thiazolidinylidene, phenanthrothiazolinylidene, acenaphthothiazolinylidene, thiazolinylidene, benzothiazolinylidene, naphthothiazolinylidene, tetrahydrobenzothiazolinylidene, dihydronaphthothiazolinylidene, thiadioxazolinylidene, selenazolidinylidene, selenazolinylidene, benzoselenazolinylidene, naphthoselenazolinylidene, selenadiazolinylidene, pyrazolylidene, imidazolinylidene, imidazolidinylidene, benzimidazolinylidene, naphthimidazolinylidene, diazolinylidene, tetrazolinylidene, and imidazoquinoxalinylidene nuclei. The nuclei can be substituted in any conventional manner consistent with formula (XIV). $R^6$ can, for example, be any conventional quaternizing group and can be chosen from among any of the various forms of $R^5$ described above.

In a specifically preferred form the cyanine dyes of this invention satisfying formula (XIV) are cyanine dyes of the formula

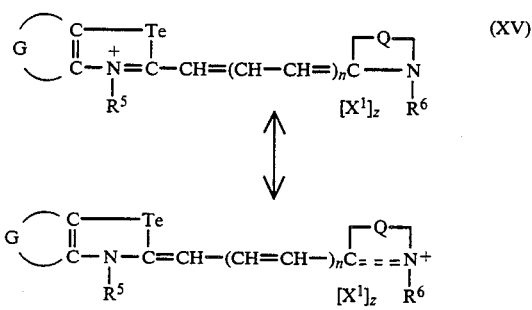

(XV)

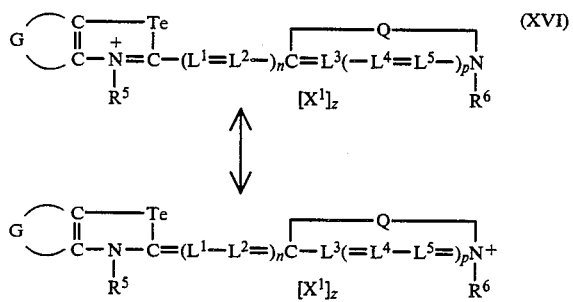

(XVI)

wherein
  G completes a fused benzo or naphtho nucleus;
  n is zero, 1, or 2;
  $R^5$ and $R^6$ are independently alkyl radicals which are optionally sulfo substituted;
  Q represents the atoms completing a basic azolinylidene or azinylidene nucleus optionally including a fused benzo or naptho ring portion;
  $X^1$ is a counterion; and
  z is a zero or a positive integer chosen to balance ionic charge.

In certain optimum forms $R^5$ and $R^6$ are sulfo or sulfato substituted hydrocarbon (e.g., alkyl or aryl) substituents containing from 1 to 6 carbon atoms, such as sulfomethyl, sulfatomethyl, sulfoethyl, sulfatoethyl, sulfopropyl, sulfatopropyl, sulfobutyl, sulfatobutyl, sulfophenyl, or sulfatophenyl substituents. Further, the benzo or naphtho nucleus completed by G, which substituted, can include one or a combination of substituents, such as alkyl, alkoxy, thioalkyl, and hydroxy substituents.

In another preferred form the cyanine dyes of this invention can be represented by the formula

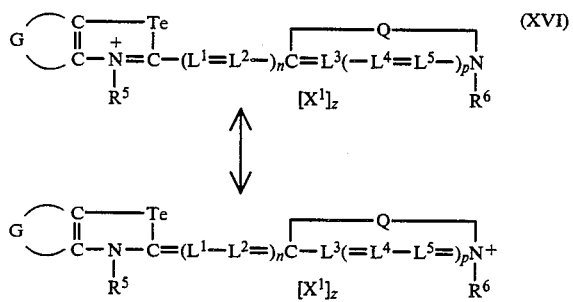

wherein
  G represents the atoms completing a fused aromatic nucleus;
  $L^1$, $L^2$, $L^3$, $L^4$, and $L^5$ each independently represent a methine group;
  n represents zero, 1, or 2;
  p represents zero or 1;
  Q represents the atoms completing a basic heterocyclic azolinylidene or azinylidene nucleus;
  $R^5$ and $R^6$ each independently represent a quaternizing substituent;
  $X^1$ represents a counterion, and
  z is zero or a positive integer chosen to balance ionic charge.

Except for the form of the azolinylidene or azinylidene ring completed by Q, the various components of formula (XVI) can be selected similarly as described above with respect to formula (XIV) and are not again discussed. In optimum forms Q in formula (XVI) is selected from among pyrrolylidene, indolylidene, carbazolylidene, benzindolylidene, pyrazolylidene, indazolylidene, and pyrrolopyridinylidene nuclei. Again, conventional ring substituents consistent with formula (XVI) are contemplated. $R^5$ and $R^6$ are optimally sulfo or sulfato substituted hydrocarbon substituents, as described above.

Preferred merocyanine dyes according to this invention are those of the formula

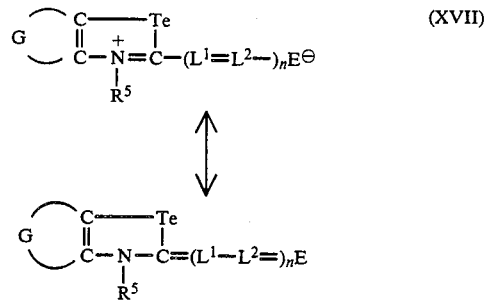

(XVII)

wherein
  E represents an acidic nucleus;
  G represents the atoms completing a fused aromatic nucleus;
  $L^1$ and $L^2$ each independently represent a methine linkage;
  n represents zero, 1, or 2; and
  $R^5$ represents a quaternizing substituent.

From formula (XVII) it is apparent that, except for the acidic nucleus E, the portions constituting the preferred merocyanine dyes can be selected from among corresponding components constituting the cyanine dyes. Accordingly, these corresponding components of the merocyanine dyes are not redescribed.

The acidic nucleus E can take the form of any conventional merocyanine acid nucleus. Typically E is in one resonance extreme comprised of a methylene moiety bonded to a carbonyl, sulfo, or cyano group directly or through a methine linkage. Unlike the nuclei of the cyanine dyes, the acidic nucleus E need not be heterocyclic or even cyclic.

In a preferred form E can be represented by the formula

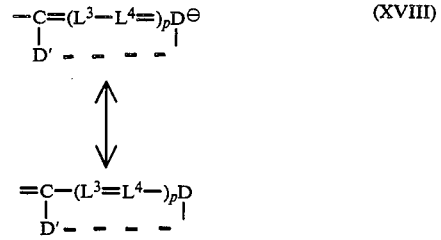

(XVIII)

wherein
  D is a cyano, sulfo, or carbonyl group,
  D' is a methine substituent, which in one form can with D complete a five or six membered heterocyclic ring containing ring atoms chosen from the class consisting of carbon, nitrogen, oxygen, and sulfur.

When E is an acyclic group—that is, when D and D' are independent groups, E can be chosen from among groups such as malononitrile, alkylsulfonylacetonitrile, cyanomethyl benzofuranyl ketone, or cyanomethyl phenyl ketone. In preferred cyclic forms of E, D, and D' together complete a 2-pyrazolin-5-one, pyrazolidene-3,5-dione, imidazoline-5-one, hydantoin, 2 or 4-thiohydantoin, 2-iminooxazoline-4-one, 2-oxazoline-5-one, 2-thiooxazolidine-2,4-dione, isoxazoline-5-one, 2-thiazoline-4-one, thiazolidine-4-one, thiazolidine-2,4-dione, rhodanine, thiazolidine-2,4-dithione, isorhodanine, indane-1,3-dione, thiophene-3-one, thiophene-3-1,1-dioxide, indoline-2-one, indoline-3-one, indazoline-3-one, 2-oxoindazolinium, 3-oxoindazolinium, 5,7-dioxo-6,7-dihydrothiazolo[3,2-a]pyrimidine, cyclohexane-1,3-dione, 3,4-dihydroisoquinoline-4-one, 1,3-dioxane-4,6-dione, barbituric acid, 2-thiobarbituric acid, chroman-2,4-dione, indazoline-2-one, or pyrido[1,2-a]pyrimidine-1,3-dione nucleus. Conventional substituents of the ring are contemplated.

The dyes according to this invention can be applied to any application where otherwise corresponding dyes containing another chalcogen atom are employed. The dyes of this invention are in a preferred application incorporated into silver halide photographic elements. The location and concentration of the dye is dictated by the photographically useful function sought to be realized. The dyes can be located behind one or more silver halide emulsion layers as imagewise exposed to absorb actinic radiation penetrating the silver halide emulsion layer or layers, thereby reducing scattered radiation. In other words, the dyes can be employed as antihalation dyes. They can be incorpoated in interlayers or in overcoats to function as filter dyes. In a preferred application they can be incorporated directly in the silver halide emulsion. The dyes can increase photographic sharpness by intercepting and absorbing actinic radiation that would otherwise be reflected between grains. In other words, the dyes can take the form of inter-grain absorbers.

A highly preferred utility for the dyes is to increase the wavelength of spectral response of silver halide grains to exposing radiation. In such an application the dyes are typically adsorbed to the surfaces of the silver halide grains. In addition the dyes can also serve the function of reducing the sensitivity of the silver halide grains in the spectral region of intrinsic or native sensitivity. This can be a desirable feature apart from spectral sensitization or can be a desirable feature in combination with spectral sensitization to increase the difference between sensitized and intrinsic speeds of the emulsions, as is desired for minus blue recording emulsions in color photography. It is specifically contemplated to employ the dyes of the present invention as spectral sensitizers in both surface and internal latent image forming emulsions. The latter emulsions offer the advantage of permitting more favorable dye concentration densensitization relationships—i.e., more dye is required to reach desensitization levels. When the dyes of the present invention are employed in combination with surface fogged silver halide emulsions intended for use in forming direct positive images, their substituents can be chosen to enhance electron trapping. As discussed above, ultraviolet, blue, green, red, and infrared absorbing dyes according to this invention are contemplated; however, dyes having absorption peaks at 500 nm and longer wavelengths are particularly advantageous.

It is not necessary for the compounds of this invention be in the form of dyes to find photographic utility. A wide variety of chalcogenazolium antifoggants and stabilizers are known in the art, and the corresponding compounds of this invention can be generally substituted therefor.

A class of compounds according the present invention that are particularly useful for photographic purposes are species of the compound of formula (VIII) wherein $R^5$ is an alkynyl substituent and R is a methyl substituent. Such a compound can be represented by the formula:

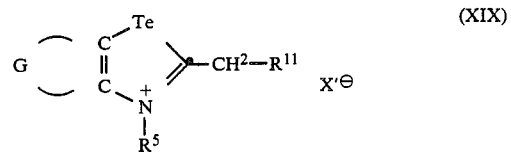

(XIX)

wherein
  G represents the atoms completing a fused aromatic nucleus;
  $R^5$ is an alkynyl radical
  $R^{11}$ can be hydrogen or any substituent which is compatible with the methylene group participating with the alkynyl group in ring closure; and
  X' is an anion.

In formula (XIX) $R^5$ is preferably an alkynyl group containing from 3 to 5 carbon atoms and is most preferably a propargyl or 2-butynyl group. $R^{11}$ is preferably hydrogen or a substituent having a Hammett sigma value derived electron withdrawing characteristic more positive than $-0.2$.

Corresponding compounds differing only by the presence of a differing chalogen atom are known to be highly useful as nucleating agents. Thus, these compounds can be employed in combination with internal latent image forming emulsions to produce direct positive images. Nucleating agents are effective if introduced into the photographic element so as to be present during processing. Thus, the nucleating agents can be present in the photographic element prior to imagewise exposure, which is preferred, or introduced in the processing solution or a pre-processing solution. In a preferred form the nucleating agent is present in the silver halide emulsion layer and, most preferably, adsorbed to the silver halide grain surface. The latter can be achieved by incorporating an adsorption promoting moiety as a substituent of the fused aromatic nuclei completed by G. Useful adsorption promoting groups as well as useful concentration levels for the compounds are disclosed in Parton et al U.s. Pat. No. 4,471,044, here incorporated by reference. Corresponding compounds lacking adsorption promoting moieties are disclosed in Adachi et al U.S. Pat. No. 4,115,122.

The compound of formula (XIX) can also be used to increase photographic speed. In this instance the compound is adsorbed to the surface of radiation sensitive silver halide grains in a surface latent image forming emulsion. Parton et al can also be referred to for details relating to this application.

It is often desired to adsorb hydrazine and hydrazine derivative (e.g., hydrazide and hydrazonoalkyl) nucleating agents to the surfaces of internal latent image forming silver halide grains. To accomplish this chalcogenazolium rings are known to be incorporated in the nucleating agents to promote grain adsorption. In one form the compounds of this invention can take the form of a tellurazolium ring moiety in any of the various forms described above linked directly or through intervening linking groups to a hydrazino or derivative nucleating moiety. For example, the compounds of the present invention can differ from the chalcogenazolium hydrazino and derivative compounds disclosed by Sidhu et al Research Disclosure, Vol. 176, December 1978, Item 17626, Lincoln et al U.S. Pat. Nos. 3,759,901 and 3,854,956, and Suga et al U.S. Pat. No. 4,150,993, merely by the presence of a divalent tellurium atom in the ring in place of the chalcogen disclosed.

Hydrazines and their hydrazide derivatives have also been taught to be useful to increase contrast to very high levels in surface latent image forming negative working emulsions. Mifune et al U.S. Pat. No. 4,272,614, here incorporated by reference, teaches incorporating such contrast increasing addenda containing heterocyclic nuclei forming 5 or 6-membered rings containing carbon, oxygen, sulfur, selenium, and nitrogen atoms. Specific ring structures disclosed are generally similar to those described above as useful as cyanine dye nuclei. It is specifically contemplated that tellurazolium salt and derivative nuclei of this invention can be substituted for the corresponding chalcogenazolium and derivative nuclei disclosed to be useful by Mifune et al. Thus, hydrazine and derivative contrast increasing addenda, particularly hydrazide contrast increasing addenda, containing in addition to the hydrazido or derivative moiety a tellurazolium salt or derivative nucleus are contemplated for use in surface latent image emulsions to increase contrast to very high levels, such as those suitable for lith applications.

In still another form the compounds of this invention can be employed to facilitate latent image keeping. A useful family of latent image keeping addenda according to the present invention correspond to those disclosed by Lok et al in U.S. Pat. No. 4,451,557 here incorporated by reference, except that the compounds of this invention contain a divalent tellurium atom in the ring instead of oxygen, sulfur, and selenium divalent atoms as disclosed by Lok et al. In a preferred form the latent image keeping addenda according to this invention can be represented by the formula:

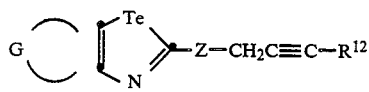 (XX)

wherein:
G completes a fused aromatic nucleus, as previously described;
R¹² is hydrogen or methyl;

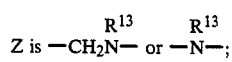

and
R¹³ is hydrogen or alkyl, preferably alkyl of from 1 to 6 carbon atoms.

The following examples further illustrate the invention:

EXAMPLES

A. Preparation of 2-Phenylazophenyltellurium Trichloride

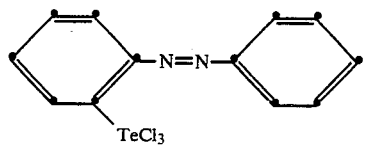

C₁₂H₉Cl₃N₂Te
mw=415.18

A two liter, 3-necked flask was fitted with mechanical stirrer (Teflon ® blade), reflux condenser and nitrogen inlet. A gas outlet from the top of the condenser was connected to a gas bubbler dipping into a magnetically stirred 1000 ml beaker containing 200 ml distilled water and a little phenolphthalein indicator. The system was sufficiently gas tight so that a very gentle stream of nitrogen produced consistent bubbles in the indicator solution.

Into the flask were placed 100 g (0.55 mole) azobenzene, 134 g (0.5 mole) tellurium tetrachloride, and 66 g (0.5 mole) anhydrous aluminum chloride. 1,2-Dichlorobenzene (500 ml) was added, the apparatus closed, the nitrogen flow started, and the mixture stirred until an orange-brown solution was obtained. Five ml of 1N sodium hydroxide were then added to the indicator solution, and the flask contents were heated to reflux with brisk stirring. The start of the reaction was marked by loss of the indicator color. Measured volume increments of 1N sodium hydroxide were then added to the beaker each time the indicator color discharged. Incremental volume and elapsed time of addition are tabulated below:

| Time Minutes | Vol. in NaOH ml |
|---|---|
| 0 | 5 |
| 6.5 | 50 |
| 13.0 | 100 |
| 20.0 | 150 |
| 28.0 | 200 |
| 36.5 | 250 |
| 46.0 | 300 |
| 54.0 | 350 |
| 70.0 | 400 |
| 85.0 | 450 |
| 94.0 | 475 |

Boiling under reflux was continued until 475 ml 1N sodium hydroxide had been consumed. The flask contents were then permitted to cool to about 80° C. Methyl alcohol was then added very slowly to the rapidly stirred solution until the initial vigorous reaction ceased. A total of 500 ml methanol was then added and the mixture cooled in ice for more than one hour. The heavy granular crystalline precipitate was collected by filtration and washed with methanol until the methanol filtrate was pale yellow.

The light brown glittering crystals were dried in vacuum. A yield of 130.3 g (63% of theory), m.p. 261°–263° C. was obtained. The product contained small amounts of oxides that were removed by recrystallization from 1,2-dichlorobenzene. Elemental analyses of the recrystallized product were in agreement with the structural formula.

B. Preparation of 3,4-Dimethoxyphenyltellurium Trichloride $C_8H_9Cl_3O_2Te$
mw = 371.13

1,2-Dimethoxybenzene (veratrole, 13.8 g=0.1 mole) and tellurium tetrachloride (26.9 g=0.1 mole) were heated in chloroform (120 ml) for 2 hours under reflux and with stirring. After 30 minutes yellow crystals started to precipitate. The product (25.2 g, 67.9% of theory) was collected by filtration and dried in a vacuum oven, m.p. 162°–163° C. (dec. with gas evolution). The mass spectra were in agreement with that of the structural formula.

C. Preparation of Bis(3,4-dimethoxyphenyl)ditelluride $C_{16}H_{18}O_4Te_2$
mw = 529.42

3,4-Dimethoxyphenyltellurium trichloride (37.2 g=0.1 mole) was dissolved in absolute ethanol (500 ml), and the slightly turbid solution was filtered. To the rapidly stirred solution was added, at room temperature, 50% aqueous hypophosphorous acid (30 ml, ≃0.3 mole) as rapidly as possible. There was a brief appearance of a brown solution color, before the entire solution set to a mass of black fibrous crystals. The product was collected after 15 minutes by filtration using rubber dam to compact the highly solvated crystal mass. The product was washed with water and then air dried to yield 25.2 g, 95% of theory, black fibrous crystals, m.p. 134°–136° C. Recrystallization from isopropanol raised the m.p. to 136°–139° C. C, H and Te elemental analyses were in agreement with the structural formula.

λ-max = 305 nm.
ε-max = 1.006 × 10$^4$.

EXAMPLE 1

1-Chloro-5,6-dimethoxy-2,1,3-benzoxatellurazole-N-oxide

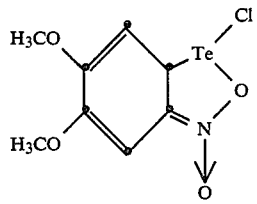

$C_8H_8ClNO_4Te$
mw = 345.21

A. By nitration of product of Preparation C

Bis(3,4-dimethoxyphenyl)ditelluride (10 g=0.018 mole) was added in small portions to 70 mole percent nitric acid (15 ml) with stirring and chilling in ice. The material dissolved rapidly with emission of nitrous fumes. The mixture was then warmed at ≃40° C. for 30 minutes and subsequently stirred at room temperature for one hour. Emission of orange fumes was no longer observed. Water (150 ml) was then added to the orange solution resulting in a yellow precipitate, which (5 g) was mixed with ethanol (100 ml) and concentrated hydrochloric acid (20 ml), then diluted with water to 200 ml (just prior to occurrence of precipitation). Hypophosphorous acid (5 ml of 50 mole percent) was then added. During 15 minutes of stirring at room temperature, a deep red precipitate appeared which was collected by filtration. The product was recrystallized from absolute ethanol (450 ml) to give red prisms, (2.5 g), m.p. 197°–200° C. The yield by this procedure calculated to be ≃32%.

B. By nitration and reduction of product of Preparation B 3,4-Dimethoxyphenyltellurium trichloride (74 g=0.2 mole) was suspended in glacial acetic acid (200 ml) in a 1500 ml Erlenmeyer flask. Nitric acid (18 g of 70%=0.2 mole) was added gradually to the stirred mixture, which caused formation of a clear, red solution and a mildly exothermic reaction. Stirring was continued for one hour at room temperature, then ethanol (1000 ml) and hypophosphorous acid (24.0 g of 50 weight percent aqueous) were added in order. Over a period of 30 minutes there occurred crystallization of a red solid, which was collected by filtration to give 47.3 g, 68.8% of theory, m.p. 199°–200° C. The material was identical to product isolated by procedure A. Elemental analyses were in agreement with that calculated for the structural formula.

EXAMPLES 2–5

Examples 2 through 5 illustrate the preparation of compounds according to the following general formula

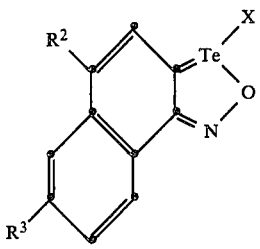

EXAMPLE 2

3-Chloronaphth[2,1-c]-1,2,5-oxatellurazole, $R^3 = R^2 = H$, $X = Cl$ $C_{10}H_6ClNOTe$
mw = 319.22

Tellurium dioxide (80 g, 0.5 mole) was dissolved in concentrated hydrochloric acid (200 ml, 2.0 moles) with stirring. When solution was complete, a suspension of hydroxylamine hydrochloride (69 g, 1.0 mole) in ethyl alcohol (300 ml) was added. When all solid was dissolved, α-tetralone (73 g, 0.5 mole) in ethyl alcohol (1200 ml) was added. The clear reaction mixture rapidly turned red and dark crystals began to form within an hour. After the reaction mixture had been kept five days at room temperature, the product was isolated by filtration and dried in a vacuum. Yield 123.2 g.

The product was separated from elemental tellurium by continuous extraction with dichloromethane in a Soxhlet extractor, using about 1300 ml of solvent. Chilling the extract yielded a first crop of 84.9 g. Diluting the filtrate with twice its volume of heptane yielded a second crop of 6.1 g. The combined yield of 91.0 g represented a 57% yield. mp. 182°–183° C. λ-max (in pyridine) was 503 nm. ε-max = 0.82 × 10$^4$. C, H, Cl, N, O and The elemental analyses results and the mass spectra were in agreement with those expected for the structural formula.

EXAMPLE 3

3-Bromonaphth[2,1-c]-1,2,5-oxatellurazole,
$R^3=R^2=H$, $X=Br$ $C_{10}H_6BrNOTe$
mw=363.68

Alpha-tetralone oxime (24 g=0.05 mole), tellurium dioxide (35 g=0.22 mole), lithium bromide (60 g), and acetic acid (350 ml) were combined, and the mixture was heated to a gentle boil for 20 minutes. The precipitated solid was collected by filtering the reaction mixture hot and washing the product with water to give 38.9 g, 71% of theory, of a deep maroon solid. The product was recrystallized from carbon tetrachloride (m.p. 183°-185° C.). Elemental analyses and the mass spectra were in agreement with the those expected for structural formula.

EXAMPLE 4

3-Chloro-5-methylnaphth[2,1-c]-1,2,5-oxatellurazole,
$R^3=H$, $R^2=CH_3$, $X=Cl$ $C_{11}H_8ClNOTe$
mw=333.24

Tellurium dioxide (79.5 g=0.5 mole) was dissolved in concentrated hydrochloric acid (200 ml). Hydroxylamine hydrochloride (35 g=0.5 mole) was added and then ethanol to bring the total volume to 2000 ml. To the slightly turbid solution was added 4-methyl-α-tetralone (80 g=0.5 mole) and the stirred mixture heated briefly to boil. The clear deep red solution was then kept overnight at room temperature. The solid mass of crystalline product was collected, washed well with water and dried in a vacuum oven at 90° C. to give a first crop (111.1 g) of dark red needles. The filtrate was heated once again and kept at room temperature for 24 hours. A second crop of 14.3 g crude product was obtained. The well-dried product was placed into a Soxhlet thimble and extracted with methylene chloride. The majority of purified product crystallized from the solvent during the course of the extraction to give a yield of 97.0 g=58.3% of theory, m.p. 196°-198° C. Elemental analyses results were in agreement with the structural formula. The ultraviolet and visible spectra in dichloromethane showed three maxima.

| | |
|---|---|
| λ-max 507 nm | ε-max = 1.21 × 10⁴ |
| λ-max 300 nm | ε-max = 1.06 × 10⁴ |
| λ-max 256 nm | ε-max = 2.30 × 10⁴ |

EXAMPLE 5

3-Chloro-7-methoxynaphth[2,1-c]-1,2,5-oxatellurazole,
$R^3=OCH_3$, $R^2=H$, $X=Cl$ $C_{11}H_8ClNO_2Te$
mw=349.24

This compound was prepared in the same general way as the corresponding compound of Example 4, except that 6-methoxy-α-tetralone (88.1 g=0.5 mole) was used as the starting ketone. The step of heating of the reaction mixture to boil and then keeping it at room temperature was repeated three times, giving a combined crude yield of 84.8 g. Recrystallization by Soxhlet extraction with dichloromethane gave 72.5 g, 41.5% yield, of small dark needles (m.p. 237°-239° C.). Elemental analyses results were in agreement with the structural formula. The ultraviolet and visible spectra in dichloromethane showed four maxima.

| | |
|---|---|
| 510 nm | ε-max = 0.89 × 10⁴ |
| 454 nm | ε-max = 0.93 × 10⁴ |
| 312 nm | ε-max = 0.81 × 10⁴ |
| 245 nm | ε-max = 2.63 × 10⁴ |

EXAMPLE 6

1-Chloroacenaphtho[1,2-d]-2,1,5-oxatellurazole

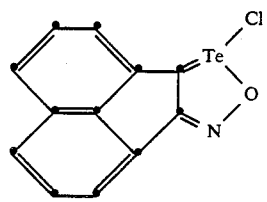

Acenaphthylen-1-one (83.5 g, 0.05 mole), hydroxylamine hydrochloride (35 g, 0.05 mole), and tellurium dioxide (80 g, 0.05 mole) were combined in ethanol (3 l). The mixture was heated to reflux and maintained at that temperature for an hour. It was then allowed to cool to room temperature and stirring at room temperature continued for 12 days. The solid was isolated by filtration, washed with ethanol, and air dried. Yield of brown powder was 106 g. This was extracted with toluene in a Soxlet extractor. The yield of product was 67.6 g, 46% of theory. The ultraviolet and visible spectra in dichloromethane solution showed four maxima, at 489.6, 429, 372, and 316 nanometers.

EXAMPLES 7-11

These examples refer to novel 1,1,1-trihalo (substituted) 2,1,4-benzotellurazinium, inner salts.

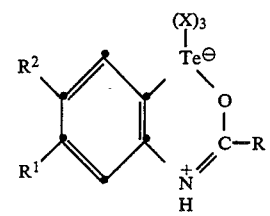

EXAMPLE 7

1,1,1-Trichloro-6-methoxy-3-methyl-2,1,4-benzoxatellurazinium, inner salt $R^1=OCH_3$, $R^2=H$, $R=CH_3$,
$X=Cl$ $C_9H_{10}Cl_3NO_2Te$
mw=398.05

3-Methoxyacetanilide, (34 g=0.2 mole) and tellurium tetrachloride (54 g=0.2 mole) were jointly stirred into chloroform (100 ml) in a 500 ml Erlenmeyer flask. After an initial solution had been formed, the mass set solid with a fine yellow precipitate. The mixture was immersed in an oil bath kept at 115° C. The mixture was manually stirred until all solids had redissolved or melted. After most of the chloroform had evaporated, there resulted a clear yellow melt that rapidly became opaque while gaseous HCl was being emitted. The temperature was raised to 120° C. and heating continued with occasional manual stirring until the entire mass had set to a brittle solid. The reaction was terminated after 2 hours. Ethanol was added to the still hot reaction mixture to disperse the product. Recrystallization from ethanol (1300 ml) yielded colorless needles (47.1 g, 59% of theory), m.p. 245°–246° C.

C, H, N and Te elemental analyses were in agreement with those calculated for the structural formula.

EXAMPLE 8

1,1,1-Trichloro-3,6-dimethyl-2,1,4-benzoxatellurazinium, inner salt $R=R^1=CH_3$, $R^2=H$, $X=Cl$ $C_9H_{10}Cl_3NOTe$
mw=382.05

3-Methylacetanilide (m-acetotoluidide) (82 g=0.55 mole) and tellurium tetrachloride (148 g, 0.55 mole) were combined with chloroform (300 ml) and the mixture heated for 20 hours in an oil bath kept at 115° C. with continuous removal of HCl. The hot reaction product was dispersed in ethanol (200 ml) and the product collected by filtration to give a yield of 149 g, 71% of theory, colorless prisms, m.p. >300° C. For analyses the compound was recrystallized from boiling acetonitrile.

The elemental analyses were in agreement with those expected for the structural formula.

EXAMPLE 9

1,1,1-Trichloro-3,6,7-trimethyl-2,1,4-benzoxatellurazinium, inner salt $R=R^1=R^2=CH_3$, $X=Cl$ $C_{10}H_{12}Cl_3NOTe$
mw=396.07

3,4-Dimethylacetanilide (56 g=0.37 mole) was combined with TeCl$_4$ (100 g, 0.37 mole) in acetonitrile (100 ml) and immersed in an oil bath, first for one hour at 120° C. and then for 3 more hours at 130° C. Additional acetonitrile was added, and the partial solution was chilled. The product was collected by filtration to give 74.7 g, 52% of theory, colorless crystals, m.p.>300° C. after darkening at >280° C. Recrystallization from acetonitrile required 400 ml solvent for 15 g of the substance. C, H, Cl, N and Te elemental analyses were in agreement with those expected for the structural formula.

EXAMPLE 10

1,1,1-Trichloro-3-methyl-6-methylthio-2,1,4-benzoxatellurazinium, inner salt $R=CH_3$, $R^1=SCH_3$, $R^2=H$, $X=Cl$ $C_9H_{10}Cl_3NOSTe$
mw=413.95

3-Methylthioacetanilide (68 g=0.37 mole), prepared by acetylation of commercial 3-methylthioaniline, was combined with TeCl$_4$ (100 g=0.37 mole) in chloroform (100 ml). The mixture was heated for 3 hours in an oil bath kept at 130° C., then introduced hot into acetonitrile (300 ml), chilled, and filtered. A crystalline solid yielding 68 g, 49% of theory was obtained. For analysis the material was recrystallized from boiling acetonitrile (100 ml dissolves≈4 g) with the aid of decolorizing charcoal and was recovered as lustrous, pale yellow prisms, m.p. 251°–253° C. The elemental analyses were in agreement with those expected for the structural formula.

EXAMPLE 11

1,1,1-Trichloro-6-hydroxy-3-methyl-2,1,4-benzoxatellurazinium, inner salt $R=CH_3$, $R^1=OH$, $R^2=H$, $X=Cl$ $C_8H_8Cl_3NO_2Te$
mw=383.95

3-Hydroxyacetanilide (60 g=0.4 mole) and TeCl$_4$ (107.6 g=0.4 mole) were combined in acetonitrile (80 ml) and the mixture immersed for 2 hours in an oil bath maintained at 120° C. To the hot melt was then added enough acetonitrile to make a paste. The mixture chilled overnight and filtered with suction to give 86.5 g, 56% of theory, colorless crystalline solid. For analysis this was recrystallized from hot acetonitrile, where 25 g required 150 ml of solvent and gave a recovery of 10 g colorless needles, m.p. 247°–248° C. The elemental analyses were in agreement with that expected for the structural formula.

D. Preparation of Bis(2-acetamido-4-methoxyphenyl)ditelluride $C_{18}H_{20}N_2O_4Te_2$
mw=583.23

1,1,1-Trichloro-6-methoxy-3-methyl-2,1,4-benzoxatellurazinium, inner salt (Example 11) (5.0 g=0.0125 mole) was dissolved in 50% aqueous ethanol (200 ml). The solution heated to boil, and hydrazine (1 ml) was added with stirring. The deep orange solution was cooled slowly to room temperature to deposit fibrous needles which, upon filtration and drying, yielded a tan solid (3.25 g, 89% of theory), m.p. 181°–182° C.

EXAMPLES 12–17

Examples 12 through 17 illustrate the preparation of benzotellurazolium hydro salts.

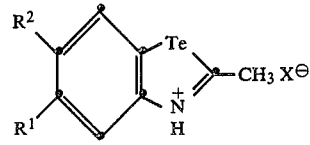

EXAMPLE 12

5,6-Dimethoxy-2-methylbenzo-3H-tellurazolium Chloride, $R^1=R^2=OCH_3$, $X=Cl$ $C_{10}H_{12}ClNO_2Te$
mw=341.26

1-Chloro-5,6-dimethoxy-2,1,3-benzoxatellurazole-N-oxide (Example 1) (103 g=0.3 mole) was suspended in a mixture of tetrahydrofuran (1000 ml) and methanol (150 ml) using a 3 liter, 3 necked flask fitted with a stirrer, a nitrogen inlet, a reflux condenser, and a powder addition funnel. Under nitrogen, sodium borohydride (61.5 g-1.6 mole) was added gradually to the stirred solution until the color was a pale cream. The amount of borohydride was determined empirically by the disappearance of the starting material red color. The reaction mixture was then chilled, and acetic anhydride was added until the color had turned a bright orange. This required 41.3 g=0.4 mole acetic anhydride. The reaction was permitted to proceed for 10 minutes, and then concentrated hydrochloric acid (300 ml) was added in one portion. The mixture turned black immediately, indicating that considerable quantities of tellurium had been generated.

The black mixture was stirred for another 30 minutes, then filtered to collect the precipitate. The solid was washed briefly with dichloromethane and air dried. The crude product was then added to 1200 ml boiling methanol containing a little hydrochloric acid and filtered hot with the aid of Celite ® diatomaceous earth. The filtrate was chilled overnight to give pale grey crystals (15.6 g). Two more crops of product were extracted from the black solid, giving a total yield of 21.34 g, 19.9% of theory. For further purification, the material was recrystallized from boiling water containing a little hydrochloric acid. The pale cream colored needles did not have a distinct melting point, but decomposed gradually >150° C.

EXAMPLE 13

5-Methoxy-2-methyl-3H-benzotellurazolium Chloride, $R^1=OCH_3$, $R^2=H$, $X=Cl$ $C_9H_{10}ClNOTe$ mw=311.24

1,1,1-Trichloro-6-methoxy-3-methyl-2,1,4-benzoxatellurazinium, inner salt (Example 7) (40 g=0.1 mole) was suspended in methanol (400 ml), and a solution of sodium hydroxide (8.0 g=0.2 mole) in water (75 ml) was added. This formed a clear solution which was placed into a vessel fitted with a stirrer, a nitrogen inlet, and a condenser. Under nitrogen, sodium borohydride (10.6 g, 0.28 mole) was added in small increments until the solution no longer turned red or orange with further additions, eventually turning colorless. Partway into the reduction, the mixture solidified, but liquified again as the reduction progressed. To the suspension, which had been cooled to ≃10° C., was then added concentrated hydrochloric acid (100 ml) in one portion. The precipitate was filtered after 15 minutes (yield 42 g dark solid), and the filtrate was chilled for a second crop of 12 g solids. The first crop was recrystallized from 700 ml of hot water containing a little hydrochloric acid. The recovery was 16.1 g of almost white needles. The second crop also contained sodium chloride. It was recrystallized from 125 ml methanol, also containing a little hydrochloric acid, to give 3.6 g product. The combined yield of 19.7 g represented 63% of theory. For analysis, the material was crystallized once more from acidic methanol, 105° C. (sinter), 130°-135° C. (turned black), no clear melt <270° C.

EXAMPLE 14

2,5-Dimethyl-3H-benzotellurazolium Chloride, $R^1=CH_3$, $R^2=H$, $X=Cl$ $C_9H_{10}ClNTe$ mw=295.24

1,1,1-Trichloro-3,6-dimethyl-2,1,4-benzoxatellurazinium, inner salt (Example 8) (17.3 g=0.05 mole) was dissolved in a mixture of methanol (300 ml and 1N sodium hydroxide (100 ml, 0.1 mole) in a vessel fitted with a nitrogen inlet, a condenser, and a magnetic stirrer. Through the condenser was added sodium borohydride until further addition no longer produced a transient orange color. This required about 3.0 g. The mixture was stirred for a few minutes under nitrogen, then concentrated hydrochloric acid (100 ml) was added in one portion. The mixture was clarified by filtration with Celite ®, then evaporated under reduced pressure to 200 ml, again filtered from inorganic salts and chilled overnight. Filtration yielded 9.15 g of colorless solid, which was rinsed with isopropanol and air dried. The material was not pure and contained inorganic salt contaminants.

EXAMPLE 15

2,5,6-Trimethyl-3H-benzotellurazolium Chloride, $R^1=R^2=CH_3$, $X=Cl$ $C_{10}H_{12}ClNTe$ mw=309.25

1,1,1-Trichloro-3,6-7-trimethyl-2,1,4-benzoxatellurazinium, inner salt (Example 9) (39.6 g=0.1 mole) was placed into 400 ml of methanol in a 1000 ml, three necked flask fitted with a stirrer, a nitrogen inlet, a condenser, and a powder addition funnel. Sodium hydroxide (8.0 g=0.2 mole) in water (30 ml) was added, followed by sodium borohydride (8.56 g=0.225 mole) until the reduction mixture was a pale brown. This required heating to aid in dissolving the starting material and the initial reduction products. When the reduction was complete, the mixture was cooled to about 10° C., and concentrated hydrochloric acid (100 ml) was added in one portion. There was a granular black precipitate, which was removed by filtration. The filtrate was evaporated in vacuum to ≃250 ml, diluted with water to twice the volume, and stirred until crystallization was complete. A yield of 29.5 g, 94.8% of theory, was obtained. After two recrystallizations from methanol, the salt melted at 180°-184° C. (dec.).

EXAMPLE 16

2-Methyl-5-methylthio-3H-benzotellurazolium Chloride, $R^1=SCH_3$, $R^2=H$, $X=Cl$ $C_9H_{10}ClNSTe$ mw=327.30

1,1,1-Trichloro-3-methyl-6-methylthio-2,1,4-benzotellurazinium, inner salt (Example 10) (20.7 g=0.05 mole) was placed in methanol (200 ml), and sodium hydroxide (4 g=0.1 mole) dissolved in water (10 ml) was added. The material did not completely dissolve. Sodium borohydride was added in portions with stirring under a nitrogen atomsphere. The starting material underwent vivid color changes to orange and then to blue with the addition of each portion of reducing agent. The mass became difficult to stir. Eventually, the reaction mixture became more liquid, though the orange color kept returning after each portion was added, as the rather insoluble starting material underwent the first reduction step. The reaction mixture was kept overnight under an atmosphere of nitrogen. The reduction was continued the next day by heating the mixture to near reflux temperature while sodium borohydride was being added. When the stage was reached where the reaction turned colorless after a portion was added and the orange color did not return upon further stirring (after the addition of 6.65 g=0.175 mole sodium borohydride), the mixture was cooled to ≃10° C. and concentrated hydrochloric acid (50 ml=0.5 mole) was added in one portion. The mixture turned orange, then yellow, and a copious beige precipitate formed. This was stirred for 45 minutes and then collected by filtration to yield 27.5 g solids. On recrystallization from methanol (300 ml), using Celite ® to clarify the solution, there were obtained 13.5 g, 81.9% of theory, cream colored needles, m.p. 130°-145° C. (dec.).

EXAMPLE 17

5-Hydroxy-2-methyl-3H-benzotellurazolium Chloride, $R^1=OH$, $R^2=H$, $X=Cl$ $C_8H_8ClNOTe$
mw=297.23

1,1,1-Trichloro-6-hydroxy-3-methyl-2,1,4-benzoxatelluarzinium, inner salt (Example 11) (19.2 g=0.05 mole) was dissolved in methanol (200 ml) with addition of sodium hydroxide (4 g) in water (20 ml). The reduction was carried out under a nitrogen atmosphere, using sodium borohydride (4.3 g=0.11 mole), after the addition of which the solution became clear. The reaction mixture was cooled to ≃10° C., and concentrated hydrochloric acid (65 ml) was added in one portion. Considerable black precipitate (11.7 g) formed, which was collected by filtration. The filtrate was evaporated to 50 ml and chilled to give a second crop (12.3 g). The products were recrystallized from isopropanol to give a combined yield of 9.45 g, 63.9% of theory, cream colored powder, m.p. 125°-132° C. (dec.).

EXAMPLES 18-25

Examples 18 through 25 illustrate the preparation of benzotellurazoles.

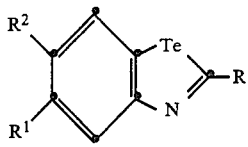

EXAMPLE 18

2-Methylbenzotellurazole, $R=CH_3$, $R^1=R^2=H$ $C_8H_7NTe$
mw=244.74

A mixture of 2-phenylazophenyltellurium trichloride (Preparation A) (20.7 g, 0.05 mole) and ethanol (200 ml) was placed in a 1 liter, 3 necked flask fitted with a nitrogen inlet, a powder addition funnel, and a reflux condenser. To the magnetically stirred mixture was added, under nitrogen, sodium borohydride (7.5 g, 0.2 mole) in increments at a rate sufficient to generate an elevated temperature. When the reaction mixture was nearly colorless the powder funnel was replaced by a stopper, taking care not to interrupt the flow of nitrogen. The flask was then chilled in an ice bath to 5° C. Acetic anhydride (5.5 g, 0.054 mole) was then added, with continued stirring and at such a rate that a temperature of 10° C. was not exceeded in the flask.

The mixture was stirred for another 20 minutes in the ice bath and then 50 ml concentrated aqueous hydrochloric acid was added rapidly. The mixture was stirred for about 10 minutes at room temperature. A black precipitate, which formed during the acid addition, was removed by filtration, washed with ethanol, and discarded, leaving a yellow filtrate.

The yellow filtrate was concentrated under reduced pressure with a bath temperature of about 45° C. When the volume was about 75 ml, the liquid was diluted with water to about 200 ml. The warm solution was clarified by filtration over Celite ® diatomaceous earth and then chilled in ice for two hours. A fluffy, crystalline solid (10.5 g) was collected by filtration. The solid was suspended in water (200 ml), and aqueous ammonium hydroxide was added until precipitation appeared to be complete. The somewhat gummy product was collected by filtration, dried superficially in a stream of air and then recrystallized from about 50 ml of isopropanol using charcoal and Celite ® to give a clear filtered solution. The compound crystallized in rod-like needles, mp 93°-95° C., yield 5.0 g, 41% of theory. Another 0.8 g was obtained from the acidic filtrate by precipitation with ammonia and subsequent diethyl ether extraction.

EXAMPLE 19

5,6-Dimethoxy-2-methylbenzotellurazole, $R=CH_3$, $R^1=R^2=OCH_3$ $C_{10}H_{11}NO_2Te$
mw=304.80

5,6-Dimethoxy-2-methylbenzotellurazolium chloride (Example 12) (10 g) was ground with an equal quantity of sodium bicarbonate and a little water in a mortar until evolution of carbon dioxide ceased. The product was collected by filtration, washed with water and dried in a vacuum to yield ≃8.5 g of colorless powder, m.p. 78°-80° C. Slow crystallization from cyclohexane yielded well defined prisms, m.p. 80°-83° C. The mass spectra and nuclear magnetic resonance spectra were in agreement with that expected for the structural formula.

EXAMPLE 20

5-Methoxy-2-methylbenzotellurazole, $R=CH_3$, $R^1=OCH_3$, $R^2=H$ $C_9H_9NOTe$
mw=274.77

5-Methoxy-2-methylbenzotellurazolium chloride (Example 13) (3.7 g=0.012 mole) was suspended in water, sodium bicarbonate in excess of that stoichiometrically required was added, and the free base product was extracted with diethyl ether. After washing with saturated sodium sulfate solution, the organic phase was dried and evaporated under reduced pressure to give a residual oil (3.2 g) which was identified by its nuclear magnetic resonance spectra. C, H, N, O and Te elemental analyses were in agreement with that expected for the structural formula.

EXAMPLE 21

2,5-Dimethylbenzotellurazole, $R=R^1=CH_3$, $R^2=H$ $C_9H_9NTe$
mw=258.69

2,5-Dimethylbenzotellurazolium chloride (Example 14) (3.5 g) was treated in an aqueous suspension with sodium bicarbonate in excess of that stoichiometrically required. The free base product was isolated by extraction with diethyl ether and evaporation to dryness. The residue was recrystallized from ≃50 ml isopropanol to yield 1.7 g colorless needles, m.p. 126°-128° C.

EXAMPLE 22

2,5,6-Trimethylbenzotellurazole, $R=R^1=R^2=CH_3$ $C_{10}H_{11}NTe$
mw=272.81

2,5,6-Trimethylbenzotellurazolium chloride (Example 15) was converted to the free base product by treatment with sodium carbonate (15 g) in water and extraction with dichloromethane (300 ml). The extract was washed as described above, dried, and evaporated to a cream colored crystalline residue (10.45 g), which was recrystallized from isopropanol (50 ml). A yield of faintly yellow needles, m.p. 101°-103° C. was obtained.

EXAMPLE 23

2-Methyl-5-methylthiobenzotellurazole, $R=CH_3$, $R^1=SCH_3$, $R^2=H$ $C_9H_9NSTe$
mw=290.84

2-Methyl-5-methylthiobenzotellurazolium chloride (Example 16) (11.5 g=0.035 mole) was suspended in water and sodium bicarbonate in excess of that stoichiometrically required was added. The free base was extracted into dichloromethane. The organic solution was washed with saturated aqueous sodium sulfate, dried, and evaporated in vacuum to a yellow oil (9.06 g). Upon addition of isopropanol (40 ml) the oil crystallized spontaneously to almost white needles to give 8.18 g, 79.8% of theory, m.p. 64°-67° C.

EXAMPLE 24

5-Hydroxy-2-methylbenzotellurazole, $R=CH_3$, $R^1=OH$, $R^2=H$ $C_8H_7NOTe$
mw=260.75

5-Hydroxy-2-methylbenzotellurazolium chloride (Example 17) (7.45 g) was dissolved in warm water (300 ml) and a slurry of sodium bicarbonate (8 g) in water was added slowly. The free base product separated as a cream colored amorphous solid, which was collected by filtration, washed with water, and dried in a vacuum over Drierite ® brand calcium sulfate drying agent, yield 6.3 g. The material was then recrystallized from isopropanol (50 ml) to give a recovery of ≃4.0g, m.p. 190°-192° C.

EXAMPLE 25

2-Ethylbenzotellurazole, $R=C_2H_5$, $R^1=R^2=H$ $C_9H_9NTe$
mw=258.76

2-Phenylazophenyltellurium trichloride (Preparation A) (10.4 g, 0.025 mole) was suspended in ethanol (100 ml) in a flask equipped with a nitrogen gas inlet, magnetic stirrer, reflux condenser, and powder addition funnel. While stirring, under a nitrogen atmosphere, at room temperature, sodium borohydride (3.8 g, 0.10 mole) was added in increments at a rate sufficient to maintain a vigorous exothermic reaction. Stirring of the reaction mixture at room temperature was continued for 30 minutes after the addition was complete, maintaining the nitrogen atmosphere. A thermometer was inserted while still maintaining a nitrogen atmosphere and propionic anhydride (3.9 g, 0.03 mole) was added dropwise. The reaction temperature rose from 25° C. to 30° C. Upon completion of the addition, stirring was continued until the temperature returned to 25° C. Concentrated hydrochloric acid (25 ml) was added dropwise to the reaction mixture, resulting in formation of a black solid. The temperature rose to around 50° C. Stirring was continued until the temperature returned to 25° C. The black solid was removed by filtration, and washed with ethanol, and discarded. The filtrate was concentrated in a rotary evaporator, diluted with about an equal volume of water, filtered through a Celite ® pad, and neutralized to a pH of about 7 with sodium bicarbonate. Extraction with diethyl ether and removal of the ether from the extracts left a red, oily semi-solid, which was purified by being dissolved in dichloromethane and being applied to a thick layer silica gel chromatography plate. An ultraviolet absorbing substance separated as a pale yellow oil. This was determined to be pure by thin layer chromatography. The infrared and nuclear magnetic resonance spectra were in agreement with that expected for the structural formula.

EXAMPLES 26-28

Examples 26 through 28 illustrate the preparation of naphthotellurazoles.

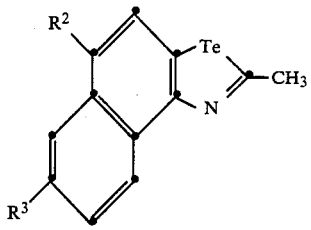

EXAMPLE 26

2-Methylnaphtho[1,2-d]tellurazole, $R^3=R^2=H$ $C_{12}H_9NTe$
mw=294.80

3-Chloronaphth[2,1-c][1,2,5]oxatellurazole (Example 2) (48.0 g=0.15 mole) was suspended in a mixture of methanol (150 ml) and tetrahydrofuran (700 ml) in a two liter 3 necked flask fitted with a mechanical stirrer, a condenser, a powder addition funnel, and a nitrogen inlet. The starting compound was reduced by gradual addition of sodium borohydride (14.2 g=0.375 mole) until the reaction mixture was a pale brown. The powder addition funnel was removed and replaced with a stopper. Final addition of sodium borohydride then took place through the condenser until the appearance of the reduced material no longer changed. The mixture was chilled in ice, still under nitrogen, and acetic anhydride (15.3 g=0.15 mole) was added dropwise. The acetylation was permitted to proceed for about 30 minutes. Concentrated hydrochloric acid (75 ml=0.75 mole) was added in one portion. After stirring the mixture, which now contained a black precipitate, for 30 minutes until it reached room temperature, the precipitate was collected by vacuum filtration, rinsed with tetrahydrofuran and air dried.

The solid was then suspended in 350 ml isopropanol, 25 ml concentrated ammonium hydroxide was added, and the mixture was heated to boiling and filtered rapidly with suction. On cooling, needles (18.65 g, 42% of theory) precipitated from the filtrate. For analyses the product was recrystallized once from isopropanol and exhibited m.p. 101°-103° C. Elemental analyses were in agreement with that expected for the structural formula.

EXAMPLE 27

7-Methoxy-2-methylnaphtho[1,2-d]-tellurazole, $R^3=OCH_3$, $R^2=H$ $C_{13}H_{11}NOTe$
mw=324.83

3-Chloro-7-methoxynaphth[2,1-c][1,2,5]oxatellurazole (Example 5) (17.45 g=0.05 mole) was reduced, acetylated, and treated with hydrochloric acid using the same method and reagent quantities as given for Example 26. Following the procedure described in Example 26, there were obtained 4.93 g, 30.2% of theory, silvery fluffy needles (m.p. 120°-123° C.). The elemental analyses were in agreement with that expected for the structural formula.

EXAMPLE 28

2,5-Dimethylnaphtho[1,2-d]tellurazole, $R^3=H$, $R^2=CH_3$ $C_{13}H_{11}NTe$
mw = 308.83

3-Chloro-5-methylnaphth[2,1-c][1,2,5]oxatellurazole (Example 4) (16.7 g=0.05 mole) was suspended in a mixture of tetrahydrofuran (THF, 200 ml) and methanol (40 ml) in a 500 ml three necked flask fitted with a nitrogen inlet, a condenser, and a powder addition funnel. Sodium borohydride was added under a nitrogen atmosphere and in small portions until the reaction mixture was a pale orange yellow. This required about 5 to 6 g. The powder addition funnel was then removed and replaced with a stopper. The reaction mixture was then cooled to 5° C. and acetic anhydride (5.1 g=0.05 mole) added slowly through the condenser. The reaction mixture transiently turned a bright orange. Concentrated hydrochloric acid (25 ml) was then added in one portion, the ice bath removed, and the mixture stirred to room temperature. As the reaction mixture warmed up, a crystalline deposit appeared and was collected by filtration. The crystalline deposit was washed with tetrahydrofuran until the filtrate was colorless and clear. The filtrate was then heated to boiling with a mixture of isopropanol (175 ml) and concentrated ammonium hydroxide (25 ml) and filtered hot with Celite®, the cooled filtrate was diluted with water until crystallization started. A first crop of pale yellow needles (5.06 g), m.p. 110°-112° C. was obtained. A further 1.65 g of product were obtained by two further extractions with the same solvent mixture, giving a total yield of 6.71 g=43.3% of theory. For analysis, the material was recrystallized from isopropanol. This did not change the melting point. Elemental analyses were in agreement with that expected for the structural formula.

EXAMPLE 29

2-Methyl-3H-benzotellurazolium Iodide

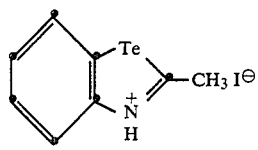

$C_8H_8INTe$
mw = 372.67

To a solution of 2-methylbenzotellurazole (Example 18) (0.81 g, 0.0033 mole) in acetone (25 ml), chilled in an ice bath, was added slowly with stirring 55 mole percent hydriodic acid (1 ml). The product began precipitating from solution. After the addition was complete, the mixture was stirred at ice bath temperature for approximately 10 minutes. The solid was isolated by filtration, washed with diethyl ether, and dried under vacuum at room temperature. Yield 1.13 g (92%) of yellow powder, m.p. 209°-211° C. The C, H, and N elemental analyses and the infrared, nuclear magnetic resonance, and mass spectra of the sample were in agreement with that expected for the structural formula.

EXAMPLES 30-59

Examples 30 through 59 illustrate the preparation of N-alkylated benzotellurazolium salts.

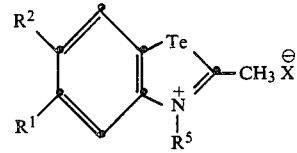

EXAMPLE 30

2,3-Dimethylbenzotellurazolium Trifluoromethanesulfonate, $R^5=CH_3$, $R^1=R^2=H$, $X=CF_3SO_3$ $C_{10}H_{10}F_3NO_3STe$
mw = 408.85

2-Methylbenzotellurazole (Example 18) (10.5 g, 0.043 mole) was dissolved in dry dichloromethane (75 ml). Freshly distilled methyl trifluoromethanesulfonate (7.5 g, 0.045 mole) was added to the solution. An exothermic reaction occurred immediately. After a few minutes a crystalline product separated which was collected by filtration, washed with diethyl ether, and dried. Yield 16.86 g (96%). The pale yellow powder was dissolved in acetone (100 ml) and reprecipitated by adding diethyl ether to the solution until it became turbid. Colorless plates separated on chilling. Yield 15.33 g (87% of theory); mp 160°-162° C.

EXAMPLE 31

5,6-Dimethoxy-2,3dimethylbenzotellurazolium Trifluoromethanesulfonate, $R^5=CH_3$, $R^1=R^2=OCH_3$, $X=CF_3SO_3$ $C_{12}H_{14}F_3NO_5STe$
mw = 468.90

5,6-Dimethoxy-2-methylbenzotellurazole (Example 19) (4.8 g=0.013 mole) was dissolved in dichloromethane (75 ml), and methyl trifluoromethanesulfonate (2.48 g=1.66 ml=0.013 mole) was added. The solution turned cloudy and crystals started to deposit within a few minutes. Precipitation was completed by addition of diethyl ether. The product was collected by filtration to give 5.5 g, 86.5% of theory, m.p. 210°-234° C. The product was recrystallized from boiling acetone (≈130 ml required) m.p. 242°-243° C.

The quaternary ammonium salts prepared in Examples 32 through 36 below were all prepared in high yield by combining stoichiometric quantities of the respective base and methyl trifluoromethanesulfonate in dichloromethane, precipitating with diethyl ether, and recrystallization from acetone, with diethyl ether in some instances being added. The C, H, F, N and Te elemental analyses and the nuclear magnetic resonance spectra were consistent with that expected for the structures of each of the quaternary salts.

EXAMPLE 32

5-Methoxy-2,3-dimethylbenzotellurazolium Trifluoromethanesulfonate, $R^5=CH_3$, $R^1=OCH_3$, $R^2=H$, $R^5=CH_3$, $X=CF_3SO_3$ $C_{11}H_{12}F_3NO_4STe$ mw=438.87
m.p. 197°–198° C.

EXAMPLE 33

2,3,5-Trimethylbenzotellurazolium Trifluoromethanesulfonate, $R^5=R^1=CH_3$, $R^2=H$, $X=CF_3SO_3$ $C_{11}H_{12}F_3NO_3STe$
mw=422.77
m.p. 215°–217° C.

EXAMPLE 34

2,3,5,6-Tetramethylbenzotellurazolium Trifluoromethanesulfonate, $R^5=R^1=R^2=CH_3$, $X=CF_3SO_3$ $C_{12}H_{14}F_3NO_3STe$
mw=436.1
m.p. 230°–233° C.

EXAMPLE 35

2,3-Dimethyl-5-methylthiobenzotellurazolium Trifluoromethanesulfonate, $R^5=CH_3$, $R^1=SCH_3$, $R^2=H$, $X=CF_3SO_3$ $C_{11}H_{12}F_3NO_3S_2Te$
mw=454.94
m.p. 195°–195° C.

EXAMPLE 36

5-Hydroxy-2,3-dimethylbenzotellurazolium Trifluoromethanesulfonate, $R^5=CH_3$, $R^1=OH$, $R^2=H$, $X=CF_3SO_3$ $C_{10}H_{10}F_3NO_4STe$
mw=424.85
m.p. 171°–175° C.

EXAMPLE 37

3-Ethyl-5,6-dimethoxy-2-methylbenzotellurazolium Trifluoromethanesulfonate, $R^5=C_2H_5$, $R^1=R^2=OCH_3$, $X=CF_3SO_3$ $C_{13}H_{16}F_3NO_5STe$
mw=482.93 (15.7 g, 0.005 mole)

5,6-Dimethoxy-2-methylbenzotellurazole (Example 19) was dissolved in chloroform (150 ml). A stoichiometric amount of ethyl trifluoromethanesulfonate was added, and the solution was refluxed for two hours under a condenser protected with a drying tube. After cooling the solution was poured slowly into cold diethyl ether (700 ml) with rapid stirring. The product crystallized and was collected by filtration. Yield 19.3 g (77.3% of theory).

The quaternary salts of the next three examples were obtained in the same gneral way as that of Example 37, except as noted, using the appropriate benzotellurazole.

EXAMPLE 38

3-Ethyl-5-methoxy-2-methylbenzotellurazolium Trifluoromethanesulfonate, $R^5=C_2H_5$, $R^1=OCH_3$, $R^2=H$, $X=CF_3SO_3$ $C_{12}H_{14}F_3NO_4STe$
mw=452.90

The alkylation was carried out in diethyl ether at room temperature. Several crops of crystalline product were collected over three days. Total yield 15.0 g (73% of theory).

EXAMPLE 39

3-Ethyl-2,5,6-trimethylbenzotellurazolium Trifluoromethanesulfonate, $R^5=C_2H_5$, $R^1=R^2=CH_3$, $X=CF_3SO_3$ $C_{13}H_{16}F_3NO_3STe$
mw=450.93

The product precipitated directly from chloroform. Yield 16.6 g (91% of theory).

EXAMPLE 40

3-Ethyl-2-methyl-5-methylthiobenzotellurazolium Trifluoromethanesulsulfonate, $R^5=C_2H_5$, $R^1=SCH_3$, $R^2=H$, $X=CF_3SO_3^{\ominus}$ $C_{12}H_{14}F_3NO_3S_2Te$
mw=468.96

The product separated from chloroform to which diethyl ether was added to aid precipitation. A gummy residue was recrystallized from ethanol.

EXAMPLES 41–44

Examples 41 through 44 use 2-propen-1-yl trifluoromethanesulfonate in a dry solution of carbon tetrachloride. This was prepared by dissolving trifluoromethanesulfonic anhydride in carbon tetrachloride (about 10 ml of solvent per g of anhydride) and chilling the solution to near 0° C. Under a nitrogen atmosphere a solution of equimolar amounts of 2-propen-1-ol (allyl alcohol) and pyridine in carbon tetrachloride (about 5 ml of solvent per g of anhydride) was added dropwise to the chilled anhydride solution. Stirring was continued for about 30 minutes after the addition was complete, maintaining the nitrogen atmosphere and ice-bath temperature. The reaction mixture was then filtered through a pad of sodium sulfate, and the dried solution was used in the subsequent examples.

EXAMPLE 41

A. 2-Methyl-3-(2-propen-1-yl)benzotellurazolium Trifluoromethanesulfonate, $R^5=CH_2-CH=CH_2$ $R^1=R^2=H$, $X=CF_3SO_3$ $C_{12}H_{12}F_3NO_3STe$
mw=434.90

The dried solution of 2-propen-1-yl trifluoromethanesulfonate (0.008 mole) in carbon tetrachloride was placed in a dropping funnel and added to a solution of 2-methylbenzotellurazole (Example 18) (1.62 g, 0.0066 mole) in dichloromethane (25 ml) under a nitrogen atmosphere at room temperature. After the addition was complete, stirring was continued for 18 hours. The solid was isolated by filtration, washed with diethyl ether, and dried at room temperature under vacuum. Yield 0.43 g (15%), m.p. 90°–93° C. Infrared, nuclear magnetic resonance, and mass spectra were in agreement with that expected for the structural formula.

B. 2-Methyl-3-(2-propen-1-yl)benzotellurazolium Iodide, $R^5=CH_2-CH=CH_2$, $R^1=R^2R^2=H$, $X=I$ $C_{11}H_{12}INTe$
mw=412.73

The solvents from the filtrates above were removed under vacuum and the dark orange semisolid redissolved in acetone (about 30 ml). The solution was stirred, and treated with a saturated solution of sodium iodide in acetone (about 5 ml). The solid was isolated by filtration, washed with acetone, diethyl ether, and dried. Yield 0.52 g (21% of theory) m.p. 205°-207° C. Elemental analyses and nuclear magnetic resonance spectra were in agreement with that expected for the structural formula.

EXAMPLE 42

5,6-Dimethoxy-2-methyl-3-(2-propen-1-yl)benzotellurazolium Trifluoromethanesulfonate,
$R^5 = CH_2-CH=CH_2$ $R^1 = R^2 = OCH_3$, $X = CF_3SO_3$ $C_{14}H_{16}F_3NO_5STe$
mw = 494.95

A dried solution of 2-propen-1-yl tri-fluoromethanesulfonate (0.002 mole) in carbon tetrachloride was added dropwise to a solution of 5,6-dimethoxy-2-methylbenzotellurazole (Example 19) (0.50 g, 0.0016 mole) in dichloromethane (25 ml) under a nitrogen atmosphere at room temperature. After the addition was complete, stirring was continued for 7 hours. The solid was isolated by filtration, washed with diethyl ether, and dried at room temperature under vacuum. Yield 0.38 g. A mass spectrogram of the compound was in agreement with that expected for the structural formula.

EXAMPLE 43

5-Methoxy-2-methyl-3-(2-propen-1-yl)benzotellurazolium Trifluoromethanesulfonate,
$R^5 = CH_2CH=CH_2$, $R^1 = OCH_3$, $R^2 = H$, $X = CF_3SO_3$ $C_{13}H_{14}F_3NO_4STe$
mw = 464.92

5-Methoxy-2-methylbenzotellurazole (Example 20) (0.91 g, 0.033 mole), dissolved in dichloromethane (25 ml), was added at room temperature under a nitrogen atmosphere to the solution of 2-propen-1-yl trifluoromethanesulfonate (0.004 mole) from a dropping funnel. The mixture was stirred at room temperature for another 21 hours after the addition was complete, maintaining the nitrogen atmosphere. The solid was isolated by filtration, washed with diethyl ether, and dried at room temperature under vacuum. Yield 0.90 g.

EXAMPLE 44

2,5,6-Trimethyl-3-(2-propen-1-yl)benzotellurazolium Trifluoromethanesulfonate, $R^5 = CH_2CH=CH_2$,
$R^1 = R^2 = CH_3$, $X = CF_3SO_3$ $C_{14}H_{16}F_3NO_3STe$
mw = 462.94

To a solution of 2,5,6-trimethylbenzotellurazole (Example 22) (9.90 g, 0.0033 mole) in dichloromethane (30 ml) was added the solution of 2-propen-1-yl trifluoromethanesulfonate (0.004 mole) rapidly at room temperature under a nitrogen atmosphere, with good stirring. Solid began separating 10 minutes after the addition was complete. Stirring under a nitrogen atmosphere was continued for about 18 hours. The solid was isolated by filtration, washed with diethyl ether, and dried under vacuum at room temperature. Yield 1.0 g, m.p. 162°-164° C. The mass spectra agreed with the assigned structural formula.

EXAMPLES 45-48

2-Propyn-1-yl trifluoromethanesulfonate was prepared in carbon tetrachloride solution and used as a dried solution in Examples 45 through 48 in the same way that 2-propen-1-yl trifluoromethanesulfonate was prepared and was used in Examples 41 through 44 starting with 2-propyn-1-ol (propargyl alcohol) and trifluoromethanesulfonic anhydride.

EXAMPLE 45

2-Methyl-3-(2-propyn-1-yl)benzotellurazolium Trifluoromethanesulfonate, $R^5 = CH_2C\equiv CH$,
$R^1 = R^2 = H$, $X = CF_3SO_3$ $C_{12}H_{10}F_3NO_3STe$
mw = 432.87

2-Methylbenzotellurazole (Example 18) (0.81 g, 0.0033 mole) was dissolved in dichloromethane (30 ml). A solution in carbon tetrachloride (25 ml) of 2-propyn-1-yl trifluoromethanesulfonate, prepared as described above, (0.004 mole) was placed in a dropping funnel and added at room temperature under a nitrogen atmosphere to the benzotellurazole solution. The mixture was stirred for about 20 hours after the addition was complete, forming a white solid, which was isolated by filtration, washed with dichloromethane, and dried at room temperature under vacuum. Yield 0.60 g (42% of theory), m.p. 150°-152° C. The infrared, nuclear magnetic resonance and mass spectra were consistent with the structural formula.

EXAMPLE 46

5,6-Dimethoxy-2-methyl-3-(2-propyn-1-yl)benzotellurazolium Trifluoromethanesulfonate,
$R^5 = CH_2-C\equiv CH$, $R^1 = R^2 = OCH_3$, $X = CF_3SO_3$ $C_{14}H_{14}F_3NO_5STe$
mw = 492.92

5,6-Dimethoxy-2-methylbenzotellurazole (Example 19) (1.0 g, 0.033 mole) was dissolved in dichloromethane (25 ml). The solution of 2-propyn-1-yl trifluoromethanesulfonate, prepared as described above, was added from a dropping funnel under a nitrogen atmosphere. After completion of the addition the mixture was stirred for 16 hours at room temperature. The solid was isolated by filtration, washed with diethyl ether, and dried under vacuum at room temperature. Yield, 1.14 g (70% of theory). The infrared, nuclear magnetic resonance, and mass spectra were in agreement with that expected for the structural formula.

EXAMPLE 47

5-Methoxy-2-methyl-3-(2-propyn-1-yl)benzotellurazolium Trifluoromethanesulfonate,
$R^5 = CH_2C\equiv CH$, $R^1 = OCH_3$, $R^2 = H$, $X = CF_3SO_3$ $C_{13}H_{12}F_3NO_4STe$
mw = 462.89

This compound was prepared in the same way and on the same scale as the compound of Example 46, except that 5-methoxy-2-methylbenzotellurazole (Example 20) was used in place of the 5,6-dimethoxy-2-methylbenzotellurazole. Yield 1.23 g, 80% of theory, pale tan powder, m.p. 172°-174° C. (dec). The infrared, nuclear magnetic resonance, and mass spectra were in agreement with that expected for the structural formula.

EXAMPLE 48

2,5,6-Trimethyl-3-(2-propyn-1-yl)benzotellurazolium Trifluoromethanesulfonate, $R^5 = CH_2C\equiv CH$,
$R^1 = R^2 = CH_3$, $X = CF_3SO_3$ $C_{14}H_{14}F_3NO_3STe$
mw = 460.93

This compound was prepared in the same way and on the same molar scale as the compound of Example 46, except that 2,5,6-trimethylbenzotellurazole (Example 22) was used in place of 5,6-dimethoxy-2-methylbenzotellurazole. Yield 1.10 g (72% of theory) cream colored powder, m.p. 189°–192° C. dec. The infrared, nuclear magnetic resonance, and mass spectra were in agreement with that expected for the structural formula.

EXAMPLES 49–52

Ethoxycarbonylmethyl trifluoromethanesulfonate was prepared in carbon tetrachloride solution and used as a dried solution in Examples 49 through 52 in the same way that 2-propen-1-yl trifluoromethanesulfonate was prepared and used in Examples 41 through 44, starting with hydroxyacetic acid, ethyl ester (ethyl glycolate).

EXAMPLE 49

3-Ethoxycarbonylmethyl-2-methylbenzotellurazolium Trifluoromethanesulfonate

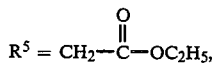

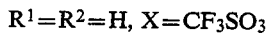

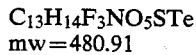

$C_{13}H_{14}F_3NO_5STe$
mw=480.91

2-Methylbenzotellurazole (Example 18) (0.81 g, 0.0033 mole) was dissolved in dichloromethane (30 ml). The solution of ethoxycarbonylmethyl trifluoromethanesulfonate (0.004 mole) in carbon tetrachloride prepared as described above, was placed in a dropping funnel and added to the benzotellurazole solution at room temperature under a nitrogen atmosphere. After the addition was complete, the mixture was stirred at room temperature, while maintaining a nitrogen atmosphere for 22 hours. The solid was isolated by filtration and dried at room temperature under vacuum. Yield was 0.62 g (39% of theory) of a white powder, m.p. 156°–158° C. The C, H, N and S elemental analyses and the infrared, nuclear magnetic resonance, and mass spectra were all in agreement with that expected for the structural formula.

EXAMPLE 50

3-Ethoxycarbonylmethyl-5,6-dimethoxy-2-methylbenzotellurazolium Iodide

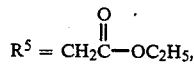

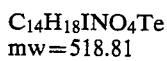

$C_{14}H_{18}INO_4Te$
mw=518.81

5,6-Dimethoxy-2-methylbenzotellurazole (Example 19) (1.22 g, 0.004 mole) was dissolved in dichloromethane (25 ml). The solution of ethoxycarbonylmethyl trifluoromethanesulfonate (0.004 mole) in carbon tetrachloride, which was prepared as described above, was placed in a dropping funnel and added slowly at room temperature and under a nitrogen atmosphere to the benzotellurazole solution. The reaction mixture was filtered to remove the small amount of solid that had formed. The solvents were removed from the filtrate under reduced pressure, and the residue was redissolved in acetone. The solution was treated with saturated sodium iodide in acetone. This was stirred for 15 minutes. After crystallization began, the mixture was chilled and then filtered. The solid was washed with diethyl ether and dried at room temperature under a vacuum. Yield 0.45 g (22% of theory) of pale yellow crystals, m.p. 184°–186° C. The infrared, nuclear magnetic resonance, and mass spectra were in agreement with that expected for the structural formula.

EXAMPLE 51

Ethoxycarbonylmethyl-5-methoxy-2-methyl-3-benzotellurazolium Iodide

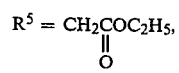

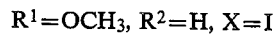

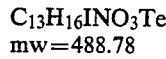

$C_{13}H_{16}INO_3Te$
mw=488.78

This compound was prepared in the same way and on the same scale as the compound of Example 50, except that 5-methoxy-2-methylbenzotellurazole (Example 20) was used in place of 5,6-dimethoxy-2-methylbenzotellurazole. Yield 0.45 g (28% of theory) of a greenish yellow powder, m.p. 215°–217° C. (dec). The infrared, nuclear magnetic resonance, and mass spectra were in agreement with that expected for the structural formula.

EXAMPLE 52

3-Ethoxycarbonylmethyl-2,5,6-trimethylbenzotellurazolium Trifluoromethanesulfonate

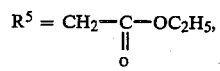

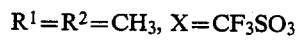

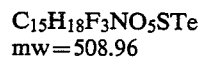

$C_{15}H_{18}F_3NO_5STe$
mw=508.96

2,5,6-Trimethylbenzotellurazole (Example 22) (0.90 g, 0.0033 mole) was dissolved in dichloromethane (25 ml). A solution of ethoxycarbonylmethyl trifluoromethanesulfonate was placed in a dropping funnel and added rapidly to the benzotellurazole solution, at room temperature and under a nitrogen atmosphere. Stirring was continued for 20 hours after the addition was complete at room temperature while maintaining a nitrogen atmosphere. The solid was isolated by filtration, washed with diethyl ether, and dried at room temperature under vacuum. Yield 0.83 g (49% of theory) of gray-white powder, m.p. 177°–179° C. (dec). The infrared, nuclear magnetic resonance, and mass spectra were in agreement with that expected for the structural formula.

An additional quantity of the compound as the iodide salt was obtained by removing the solvents from the filtrate under reduced pressure, redissolving the residue in acetone, and treating with a saturated solution of sodium iodide in acetone. The yellow solid which formed was isolated by filtration, washed, and dried as before. Yield 0.30 g, m.p. 222°–224° C. (dec.). The various spectra were also in agreement with that expected for the structural formula.

EXAMPLES 53-55

Benzyl trifluoromethanesulfonate was prepared in carbon tetrachloride solution and used as a dried solution in Examples 53 through 55, in the same way the 2-propen-1-yl trifluoromethanesulfonate was prepared and used in Examples 41 through 44, starting with benzyl alcohol and trifluoromethanesulfonic anhydride.

EXAMPLE 53

3-Benzyl-2-methylbenzotellurazolium Trifluoromethanesulfonate

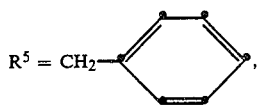

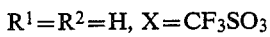

$R^1 = R^2 = H$, $X = CF_3SO_3$ $C_{16}H_{14}F_3NO_3STe$
mw = 484.94

2-Methylbenzotellurazole (Example 18) (0.81 g, 0.0033 mole) was dissolved in dichloromethane (25 ml). The solution of benzyl trifluoromethanesulfonate (0.004 mole) in carbon tetrachloride, prepared as described above, was placed in a dropping funnel and added at room temperature under a nitrogen atmosphere to the benzotellurazole solution. Stirring was continued for 18 hours at room temperature after the addition was complete, maintaining a nitrogen atmosphere. The solid was isolated by filtration, washed with diethyl ether, and dried at room temperature under a vacuum. Yield 0.30 g (19% of theory) of a white powder, m.p. 120°-122° C. The infrared, nuclear magnetic resonance, and mass spectra of this compound were in agreement with that expected for the structural formula.

EXAMPLE 54

3-Benzyl-5,6-dimethoxy-2-methylbenzotellurazolium Trifluoromethanesulfonate

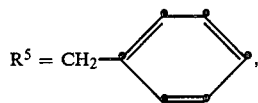

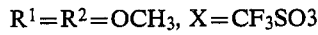

$R^1 = R^2 = OCH_3$, $X = CF_3SO_3$ $C_{18}H_{18}F_3NO_5STe$
mw = 544.99

This compound was prepared in the same way and on the same scale as the compound of Example 53, except that 5,6-dimethoxy-2-methylbenzotellurazole (Example 19) was used in place of 2-methylbenzotellurazole. Yield 0.50 g of a pale gray powder, m.p. 179°-182° C. (dec). The infrared, nuclear magnetic resonance, and mass spectra were in agreement with that expected for a mixture of desired compound and the hydro salt 5,6-dimethoxy-2-methylbenzotellurazole.

EXAMPLE 55

3-Benzyl-2,5,6-trimethylbenzotellurazolium Iodide

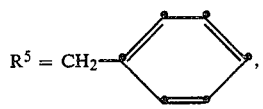

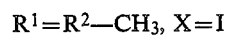

$R^1 = R^2 = CH_3$, $X = I$ $C_{17}H_{18}INTe$
mw = 490.84

This compound was prepared in the same way and on the same scale as the compound of Example 53, except that 2,5,6-trimethylbenzotellurazole (Example 22) was used in place of 2-methylbenzotellurazole and the product which was isolated directly from the reaction mixture was primarily the hydro salt of 2,5,6-tri-methylbenzotellurazole. The solvents were removed from the filtrate under reduced pressure. The residue was redissolved in acetone and treated with a standard solution of sodium iodide in acetone. The solid isolated was washed and dried as before. Yield 0.10 g, m.p. 203°-206° C. (dec). The infrared and nuclear magnetic resonance spectra were in agreement with that expected for the structural formula.

EXAMPLE 56

2-Methyl-3-[2-(2,2-dimethyl-1,3-dioxolan-4-yl)ethyl]-benzotellurazolium Iodide

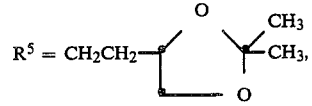

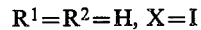

$R^1 = R^2 = H$, $X = I$ $C_{15}H_{20}INO_2Te$
mw = 500.84

2-(2,2-Dimethyl-1,3-dioxolan-4-yl)ethyl trifluoromethane sulfonate was prepared in carbon tetrachloride solution and used as a dried solution in this example in the same way as 2-propen-1-yl trifluoromethanesulfonate was prepared and used in Examples 41 through 44, starting with 2,2-di-methyl-4-(2-hydroxyethyl)1,3-dioxolane and trifluoromethanesulfonate.

2-Methylbenzotellurazole (Example 18) (0.81 g, 0.0033 mole) was dissolved in dichloromethane (20 ml), and a solution of 2-(2,2-dimethyl-1,3-dioxolan-4-yl)ethyl trifluoromethanesulfonate in carbon tetrachloride was added from a dropping funnel at room temperature under a nitrogen atmosphere. After the addition was complete, the mixture was stirred for 21 hours at room temperature while maintaining a nitrogen atmosphere. The reaction mixture was filtered, and the solvent was removed from the filtrate under reduced pressure. The residue was dissolved in a small amount of acetone, and the solution was then treted with a saturated solution of sodium iodide in acetone. Diethyl ether was added to precipitate the product, which was isolated by filtration, washed with diethyl ether, and dried at room temperature under vacuum. The yield of pale yellow powder was 0.67 g (41% of theory), m.p. 158°-160° C. C, H and N elemental analyses and the infrared, nuclear magnetic resonance, and mass spectra of this sample were in agreement with that expected for the structural formula.

EXAMPLES 57-59

The following three compounds, Examples 57 through 59, were prepared by the same general procedure. The appropriate 2-methylbenzotellurazole base, 2-methylbenzotellurazole for Example 57, 5,6-dimethoxy-2-methylbenzotellurazole for Example 58, and 5-methoxy-2-methylbenzotellurazole for Example 59, was heated with trimethylene sulfate in equimolar amounts at 75° to 80° C. in a flask equipped with a magnetic stirrer and reflux condenser for 18 hours (3 hours in Example 59). The reactants initially formed a melt, but ultimately the mass became solid. After cooling to room temperature the solid was removed and then crushed and stirred in acetone until a uniform slurry was obtained. The solid was isolated by filtration, washed with more acetone and dried at room temperature under a vacuum. At least one product, Example 59, was observed to decompose on standing in air. Infrared, nuclear magnetic resonance, and mass spectra of each of these three examles were in agreement with that expected for the structural formulae.

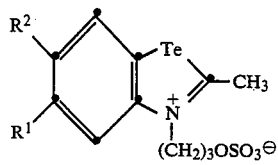

EXAMPLE 57

Anhydro-2-methyl-3-(3-sulfatopropyl)benzotellurazolium Hydroxide, $R^1=R^2=H$ $C_{11}H_{13}NO_4STe$
mw=382.88

Yield 79%, tan powder, m.p. 202°-204° C. (dec.).

EXAMPLE 58

Anhydro-5,6-dimethoxy-2-methyl-3-(3-sulfatopropyl)-benzotellurazolium Hydroxide, $R^1=R^2=OCH_3$ $C_{13}H_{17}NO_6STe$
mw=442.93

Yield 61%, tan powder, m.p.>250° C.

EXAMPLE 59

Anhydro-5-methoxy-2-methyl-3-(3-sulfatopropyl)benzothiazolium Hydroxide, $R^1=OCH_3$, $R^2=H$ $C_{12}H_{15}NO_5STe$
mw=412.91

Yield 79%, tan powder.

EXAMPLES 60-62

Examples 60 through 62 illustrate the preparation of the 3-substituted naphtho[1,2-d]tellurazolium salts:

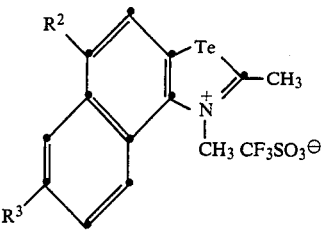

EXAMPLE 60

1,2-Dimethylnaphtho[1,2-d]tellurazolium Trifluoromethanesulfonate, $R^3=R^2=H$ $C_{14}H_{12}F_3NO_5STe$
mw=458.92

2-Methylnaphtho[1,2-d]tellurazole (Example 26) (14.8 g=0.05 mole) was dissolved in dry dichloromethane, and methyl trifluoromethanesulfonate (5.52 ml=0.05 mole) was added. The flask was sealed and kept over a weekend. Pale yellow plates (16.1 g, 70% of theory) formed. The product was recrystallized from 150 ml of acetone by addition of diethyl ether (m.p. 178°-183° C.). The mass and nuclear magnetic resonance spectra were in agreement with that expected for the structural formula.

EXAMPLE 61

7-Methoxy-1,2-dimethylnaphtho[1,2-d]tellurazolium Trifluoromethanesulfonate, $R^3=OCH_3$, $R^2=H$ $C_{15}H_{14}F_3NO_4STe$
mw=488.93

7-Methoxy-2-methylnaphtho[1,2-d]tellurazole (Example 27) (0.98 g=0.03 mole) was alkylated as described above for Example 60. The reaction mixture was kept at room temperature for 5 days to yield 0.68 g, 46% of theory, yellow fluffy needles (m.p. 174°-183° C.). The mass and nuclear magnetic resonance spectra were in agreement with that expected for the structural formula.

EXAMPLE 62

1,2,5-Trimethylnaphtho[1,2-d]tellurazolium Trifluoromethanesulfonate, $R^3=H$, $R^2=CH_3$ $C_{15}H_{14}F_3NO_3STe$
mw=472.93

2,5-Dimethylnaphtho[1,2-]tellurazole (Example 28) (0.93 g=0.003 mole) was dissolved in dry dichloromethane, and methyl trifluoromethanesulfonate (0.33 ml=0.003 mole) was added. The flask was sealed and kept over a weekend. Bright yellow plates (0.88 g, 61% of theory) formed. The product was recrystallized from 10 ml of acetone by addition of 20 ml of diethyl ether. The melting point was 224°-230° C. The mass and nuclear magnetic resonance spectra were in agreement with that expected for the structural formula.

Polymethine Dye

The following examples illustrate the number and variety of polymethine dyes that can be prepared and illustrate procedures than can be used to obtain them.

EXAMPLES 63-67

Examples 63 through 67 illustrate the preparation of symmetrical cyanine dyes.

EXAMPLE 63

3,3'-Dimethyltelluracarbocyanine Trifluoromethanesulfonate

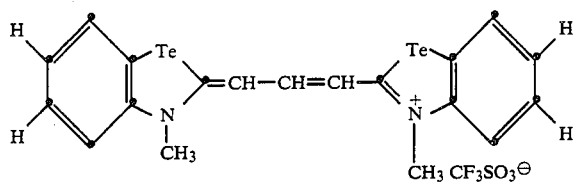

C$_{20}$H$_{17}$F$_3$N$_2$O$_3$STe$_2$
mw=677.62

2-(2-Acetanilidovinyl-3-methylbenzotellurazolium trifluoromethylsulfonate (1.1 g, 0.002 mole), prepared by reaction of the corresponding 2-methyl quaternary salt with diphenylformamidine, and 2,3-dimethylbenzotellurazolium trifluoromethanesulfonate (Example 30) (0.81 g, 0.002 mole) were dissolved in acetonitrile (50 ml). A solution of triethylamine (0.20 g) in acetonitrile (20 ml) was added dropwise. The mixture was stirred at room temperature for 15 minutes after addition of the triethylamine was complete. The solid was isolated by filtration, washed with diethyl ether, and dried. Yield 0.87 g (79% of theory). The dye was recrystallized from m-cresol by the addition of methanol. The due purity was verified by thin layer chromatography and electrophoresis.
λ-max methanol: 601 nm
ε-max: 10.64×10$^4$

EXAMPLE 64

5,5'-Dihydroxy-3,3'-dimethyltelluracarbocyanine Trifluoromethanesulfonate

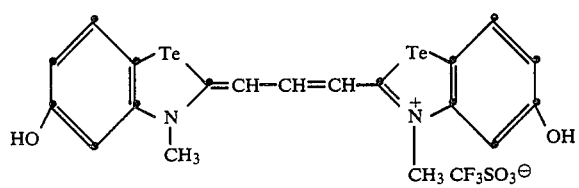

C$_{20}$H$_{17}$F$_3$N$_2$O$_5$STe$_2$
mw=709.61

5-Hydroxy-2,3-dimethylbenzotellurazolium trifluoromethanesulfonate (Example 36) (1.70 g., 0.004 mole) was dissolved in dimethylformamide (50 ml). Triethoxymethane (0.30 g., 0.002 mole) was added, and the solution was refluxed for 30 minutes. After chilling the dye was precipitated by the addition of diethyl ether, isolated by filtration, and dried at room temperature under vacuum. Yield 0.65 g. It was recrystallized from m-cresol with diethyl ether added to aid reprecipitation. Yield 0.40 g. (28% of theory). Dye purity was verified by thin layer chromatography and electrophoresis.
λ-max (methanol)=625 nm. ε-max=8.455×10$^4$.

EXAMPLE 65

3,3'-Dimethyltelluradicarbocyanine Trifluoromethanesulfonate

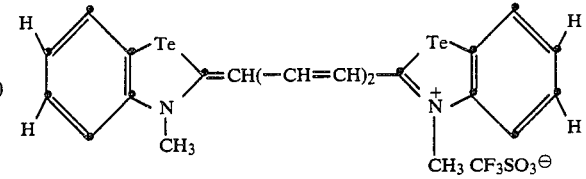

C$_{22}$H$_{19}$F$_3$N$_2$O$_3$STe$_2$
mw=703.64

2-(4-Acetanilido-1,3-butadienyl)-3-methylbenzotellurazolium trifluoromethanesulfonate (Example 87) (2.90 g, 0.005 mole), 2,3-dimethylbenzotellurazolium trifluoromethanesulfonate (2.0 g, 0.005 mole) (Example 30), and sodium bicarbonate were dissolved in a solvent mixture of acetonitrile (75 ml) and water (10 ml). The mixture was warmed gently (to about 30° C.). After stirring for ½ hour the solid was isolated by filtration and dried. Yield 1.36 g (39%). The solid was recrystallized from methanol (2 liters). After a second recrystallization from warm m-cresol (20 ml) by the addition of methanol (20 ml) the dye was pure by ionographic and thin layer chromatographic tests.
λ-max: 686.5 nm
ε-max: 19.65×10$^4$

EXAMPLE 66

5,6-Dimethoxy-3,3'-dimethyltelluradicarbocyanine Trifluoromethanesulfonate

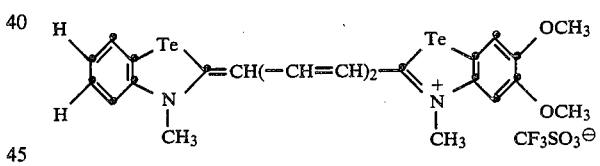

C$_{24}$H$_{23}$F$_3$N$_2$O$_5$STe$_2$
mw=763.09

2-(4-Acetanilido-1,3-butadienyl)-3-methylbenzotellurazolium trifluoromethanesulfonate (Example 89) (1.16 g, 0.002 mole), and 5,6-dimethoxy-2,3-dimethylbenzotellurazolium trifluoromethanesulfonate (0.94 g 0.002 mole) were suspended in acetonitrile (75 ml). A solution of triethylamine (0.20 g) in acetonitrile (20 ml) was added slowly. After 20 minutes stirring at room temperature water was added. The solid was isolated by filtration, and the product was washed with methanol and dried. Yield 1.12 g.

The dye was purified by dissolving it in a small amount of m-cresol (about 50 ml), heated by a steam bath, filtered quickly, diluted with methanol, and cooled to reprecipitate the dye as a very fine coppery-grey powder. Dye purity was verified by thin layer chromatography and electrophoresis.
λ-max: 703 nm
ε-max: 16.39×10$^4$

EXAMPLE 67

5,5',6,6'-Tetramethoxy-3,3'-dimethylteIluradicarbocyanine Trifluoromethanesulfonate

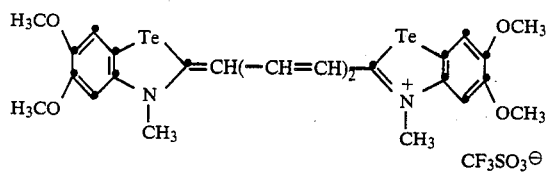

mw=823.75

2-(4-Acetanilido-1,3-butadienyl)-5,6-dimethoxy-3-methanebenzotellurazolium trifluoromethanesulfonate (Example 88) (1.28 g, 0.002 mole), and 5,6-dimethoxy-2,3-dimethylbenzotellurazolium trifluoromethanesulfonate (0.94 g, 0.002 mole) were suspended in acetonitrile (75 ml). A solution of triethylamine (0.20 g) in acetonitrile (10 ml) was added. The mixture slowly turned orange-brown. After 15 minutes stirring the solid which precipitated was isolated by filtration, washed with methanol and dried. The dye was recrystallized by dissolving it in a small amount of m-cresol and reprecipitation by the addition of methanol. Yield 0.40 g (25%).

λ-max methanol: 723 nm
ε-max: 17.45×10$^4$

The syntheses of the dyes of examples 68 through 79 were carried out by suspending or dissolving both the benzotellurazolium or naphtho[1,2-d]tellurazolium quaternary salt, Reactant A, and a suitable Reactant B in dry acetonitrile (AcCN). A stoichiometrically calculated quantity of triethylamine was added to the mixture with stirring at room temperature. Stirring was continued until the dye forming reaction appeared to be completed, either because no further change in light absorption was observed or because product precipitation had ceased. The cationic dyes were converted to their iodide salts by addition of sodium iodide to their methanolic solutions. The dyes were then purified by recrystallization, usually from methanol or ethanol. The zwitterionic dyes were purified by recrystallization from m-cresol by the addition of methanol (5 ml/100 ml).

EXAMPLES 68–79

Examples 68 through 79 illustrate the preparation of unsymmetrical cyanine dyes:

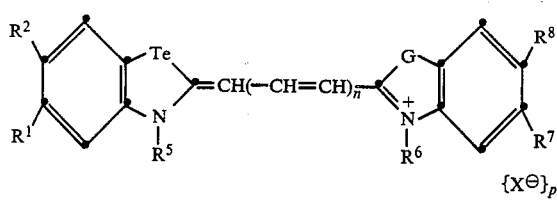

EXAMPLE 68

3'-Ethyl-3-methyltellurathiacyanine Iodide, n=0, G=S, X=I, p−1, R$^5$=CH$_3$, R$^6$=C$_2$H$_5$, R$^1$=R$^2$=R$^7$=R$^8$=H

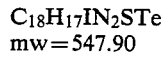
mw=547.90

EXAMPLE 69

3-Ethyl-3'-methyloxatelluracarbocyanine Iodide, n−1, G=O, X=I, p=1, R$^5$=CH$_3$, R$^6$=C$_2$H$_5$, R$^1$=R$^2$=R$^7$=R$^8$=H

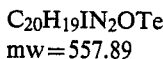
mw=557.89

EXAMPLE 70

3'-Ethyl-3-methyltellurathiacarbocyanine Iodide, n−1, G=S, X=I, p=1, R$^5$=CH$_3$, R$^6$=C$_2$H$_5$, R$^1$=R$^2$=R$^7$=R$^8$=H

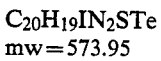
mw=573.95

EXAMPLE 71

Anhydro
5,6-dichloro-3-ethyl-3'-5'-dimethyl-3'-(3-sulfopropyl)-benzimidazolotelluracarbocyanine Hydroxide, n=1, p=0, R$^1$=R$^5$=CH$_3$, R$^8$=R$^7$=Cl R$^2$=H, R$^6$=SO$_3$(CH$_2$)$_3$, G=N-C$_2$H$_5$

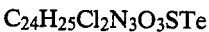
mw=634.05

EXAMPLE 72

Anhydro
5=-Chloro-3,5-dimethyl-3'-(3-sulfopropyl)tellurathiacarbocyanine Hydroxide, G=S, n=1, p=0, R$^1$=R$^5$=CH$_3$, R$^6$=SO$_3$(CH$_2$)$_3$, R$^7$=Cl, R$^2$=R$^8$=H

mw=589

EXAMPLE 73

Anhydro
5-Chloro-3',5'-dimethyl-3-(3-sulfopropyl)selenateIluracarbocyanine Hydroxide, n−1, p=0, G=Se, R$^1$=R$^5$=CH$_3$, R$^6$=SO$_3$(CH$_2$)$_3$, R$^8$=Cl, R$^2$=R$^7$=H

mw=636

EXAMPLE 74

3-Ethyl-5',6'-dimethoxy-3'-methyloxatelluracarbocyanine Iodide, n−1, G=O, X=I, p−1, R$^5$=CH$_3$, R$^6$=C$_2$H$_5$, R$^1$=R$^2$=OCH$_3$, R$^8$=R$^7$=H

mw=617.94

EXAMPLE 75

3'-Ethyl-5,6-dimethoxy-3-methyltellurathiacarbocyanine Iodide, n−1, G=S, X=I, p−1, R$^5$=CH$_3$, R$^6$=C$_2$H$_5$, R$^1$=R$^2$=OCH$_3$, R$^8$=R$^7$=H

mw=633.78

EXAMPLE 76

3'-Ethoxycarbonylmethyl-3-ethyloxatelluracarbocyanine Iodide

$n=1$, $G=O$, $R^6=C_2H_5$, $R^1=R^2=R^8=R^7=H$, $X=I$, $p=1$ $C_{23}H_{23}IN_2O_3Te$
mw=630

EXAMPLE 77

3'-[2-(2,2-Dimethyl-1,3-dioxolan-4-yl)-ethyl]-3-ethyloxatelluracarbocyanine Iodide, $n-1$, $G=O$,

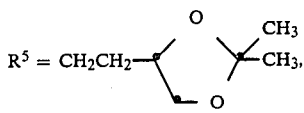

EXAMPLE 79

1-Ethyl-5',6'-dimethoxy-3'-methylnaphtho[1,2-d]thiazolotelluracarbocyanine Iodide, $R^1=R^2=OCH_3$ $C_{26}H_{25}IN_2O_2STe$
mw=684.07

The preparative details are in Table I. Reactants B are listed below; λ-max values in the table were determined in methanol. Wavelengths (e.g., λ-max values) are expressed in nanometers in each occurrence. Extinction coefficients (i.e., ε-max values) are expressed in units of liters/mole-cm in each occurrence throughout the examples.

TABLE I

| Dye Ex. No. | Reactant A | grams/moles | Reactant B | grams/moles | Solv (ml) | Time | Recrystallization Solv | grams/ml | Yield % | λ-max (nm) | ε-max |
|---|---|---|---|---|---|---|---|---|---|---|---|
| 68 | Ex. 30 | 0.80/0.002 | (b) | 0.50/0.0024 | 50 | 17 hr | — | — | 36 | 437 | 6.30 × 10⁴ |
| 69 | Ex. 30 | 0.80/0.002 | (a) | 0.90/0.0021 | 100 | 30 min | MeOH | 0.54/300 | 36 | 539 | 12.16 × 10⁴ |
| 70 | Ex. 30 | 0.80/0.002 | (c) | 0.90/0.0020 | 80 | 17 hr | MeOH | 0.57/800 | 50 | 578 | 12.63 × 10⁴ |
| 71 | Ex. 86 | 0.96/0.002 | (e) | 0.70/0.002 | 25ᵖ | 5 min | Cresol/MeOH | 0.57/150 | 35 | 541 | 7.20 × 10⁴ |
| 72 | Ex. 33 | 0.84/0.002 | (f) | 0.61/0.002 | 30ᵍ | 2 min | Cresol/MeOH | — | 36 | 590 | 10.40 × 10⁴ |
| 73 | Ex. 33 | 0.84/0.002 | (g) | 0.71/0.002 | 30ᵍ | 2 min | Cresol/MeOH | — | 31 | 598ˣ | 8.60 × 10⁴ |
| 74 | Ex. 31 | 0.95/0.002 | (a) | 1.25/0.0028 | 20 | 30 min | MeOH | 0.97/800 | — | 556.5 | 10.38 × 10⁴ |
| 75 | Ex. 31 | 0.95/0.002 | (a) | 1.25/0.0028 | 20 | 30 min | MeOH | 1.20/1100 | — | 597 | 10.70 × 10⁴ |
| 76 | Ex. 39 | 0.24/0.005 | (a) | 0.22/0.0005 | 5 | 5 min | EtOH | — | 31 | 541 | 11.34 × 10⁴ |
| 77 | Ex. 56 | 0.25/0.0005 | (a) | 0.22/0.0005 | 5 | 5 min | EtOH | — | 38 | 541 | 11.83 × 10⁴ |
| 78 | Ex. 30 | 0.80/0.002 | (d) | 1.00/0.0021 | 50ʳ | 30 min | MeOH | 0.57/150 | 46 | 597 | 11.86 × 10⁴ |
| 79 | Ex. 33 | 1.00/0.002 | (d) | 1.00/0.0021 | 50ʳ | 10 min | AcCN | 1.22/1500 | — | 614 | 8.76 × 10⁴ |

(a) 2-(2-Acetanilidovinyl)-3-ethylbenzoxazolium Iodide
(b) Anhydro 3-ethyl-2-sulfatobenzothiazolium Hydroxide Iodide
(c) 2-(2-Acetanilidovinyl)-3-ethylbenzothiazolium Iodide
(d) 2-(2-Anilinovinyl)-1-ethylnaphtho[1,2-d]thiazolium Iodide
(e) Anhydro 5,6-Dichloro-1-ethyl-2-methyl-3-(3-sulfopropyl)benzimidazolium Hydroxide
(f) Anhydro 5-Chloro-2-methyl-3-(3-sulfopropyl)benzothiazolium Hydroxide
(g) Anhydro 5-Chloro-2-methyl-3-(3-sulfopropyl)benzoselenazolium Hydroxide
ᵖacetonitrile-water 80/20 was used. 1,5-Diazabicyclo[3,2,2]-nonane was used instead of triethylamine
ᵍacetonitrile-water 80/20 was used
ʳacetic anhydride also present in calculated quantity
ˣsolvent was cresol (10%)-methanol (90%)

$X=I$, $p-1$, $R^6=C_2H_5$, $R^1=R^2=R^8=R^7=H$ $C_{26}H_{29}IN_2O_3Te$
mw=672.05

Examples 78 and 79 illustrated unsymmetrical dyes having a naphtho[1,2-d]thiazole nucleus.

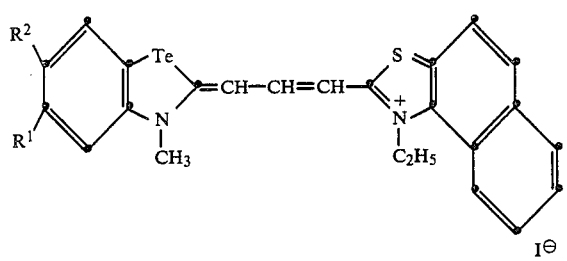

EXAMPLE 78

1-Ethyl-3'-methylnaphtho[1,2-d]thiazolotelluracarbocyanine Iodide, $R^1=R^2=H$ $C_{24}H_{21}IN_2STe$
mw=624.01

EXAMPLES 80 AND 81

Examples 80 and 81 illustrate oxatelluracarbocyanine dyes.

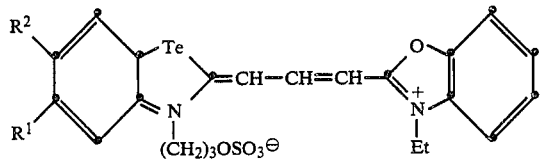

EXAMPLE 80

Anhydro-3-ethyl-3'-(3-sulfatopropyl)oxatelluracarbocyanine Hydroxide, $R^1=R^2=H$ $C_{22}H_{22}N_2O_5STe$
mw=554.22

Anhydro-2-methyl-3-(3-sulfatopropyl)benzotellurazolium hydroxide (Example 57) (0.38 g, 0.001 mole) and 2-(2-acetanilidovinyl)-3-ethylbenzoxazolium iodide (0.44 g, 0.001 mole) were suspended in an acetonitrile-dimethylformamide solvent mixture (25 ml-5 ml). Triethylamine (0.10 g) was added, and with stirring the mixture was heated to reflux. A deep maroon colored solution formed. After a few minutes of refluxing the mixture was cooled to room temperature, crystallization was induced, and the mixture was chilled thoroughly. The solid dye was isolated by filtration, washed with diethyl ether, and dried at room temperature under vacuum. Yield 0.27 g.

The dye was recrystallized from methanol (80 ml). Yield 0.17 g (31% of theory).

The elemental analysis and infrared and nuclear magnetic resonance spectra were consistent with the dye structure. The sample was pure as determined by a battery of thin layer chromatograms and an ionogram.
λ-max (methanol)=542 nm
ε-max=11.63×10⁴

EXAMPLE 81

Anhydro 3-ethyl-5',6'-dimethoxy-3'-(3-sulfatopropyl)oxatelluracarbocyanine Hydroxide, $R^1=R^2=OCH_3$ $C_{24}H_{26}N_2O_7STe$
mw=614.27

Anhydro-2-methyl-5,6-dimethoxy-3-(3-sulfatopropyl)benzotellurazolium hydroxide (Example 58) (0.44 g, 0.001 mole) and 2-(3-acetanilidovinyl)-3-ethyl benzoxazolium iodide (0.43 g, 0.001 mole) were suspended in an acetonitrile-dimethylformamide solvent mixture (25 ml-10 ml). Triethylamine (0.11 g) was added with stirring. The mixture was heated with stirring at reflux for about five minutes and then chilled. The purple solid which crystallized was isolated by filtration, washed with diethyl ether, and dried at room temperature under vacuum. Yield 0.41 g. The dye was recrystallized from a 5:1 (volume ratio) methanol dimethylformamide solution, washed with diethyl ether, and dried as before. Yield 0.16 g (26%).

The elemental analyses and infrared and nuclear magnetic resonance spectra were in agreement with that expected for the dye structural formula. The sample was pure as determined by a battery of thin layer chromatograms and an ionogram.
λ-max (methanol)=561 nm
ε-max=9.39×10⁴

EXAMPLES 82 AND 83

Examples 82 and 83 illustrate naphtho[1,2-d]tellurazolocarbocyanine dyes.

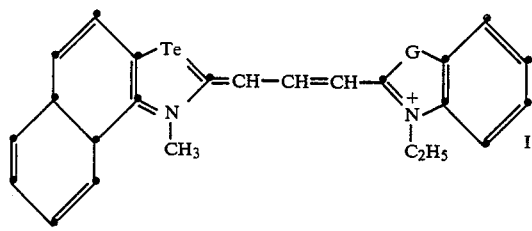

EXAMPLE 82

3'-Ethyl-1-methylnaphtho[1,2-d]tellurazolooxacarbocyanine Iodide, G=O $C_{24}H_{21}IN_2OTe$
mw=607.97
λ-max (methanol)=564 nm
ε-max=11.98×10⁴

EXAMPLE 83

3'-Ethyl-1-methylnaphtho[1,2-d]tellurazolothiacarbocyanine Iodide, G=S $C_{24}H_{21}IN_2STe$
mw=624.03
λ-max (methanol)=603 nm
ε-max=10.58×10⁴

The dyes of Examples 82 and 83, were prepared by dissolving one equivalent of 2,3-dimethylnaphtho[1,2-d]tellurazolium trifluoromethanesulfonate and two equivalents of either 2-(2-acetanilidovinyl)-3-ethylbenzoxazolium iodide (for Example 82) or 2-(2-acetanilidovinyl)-3-ethylbenzothiazolium iodide (for Example 83) in dimethylformamide. Triethylamine, one equivalent plus 25%, was added dropwise with stirring at room temperature, and the reaction mixture was stirred for a few additional minutes before diethyl ether was added to precipitate the product. The product was isolated by filtration, redissolved in methanol, treated with sodium iodide, and chilled. The crystalline dye was isolated by filtration, dried, and recrystallized once more from methanol. The yield of dye of Example 82 was 36%. The yield of Example 83 was 45%. The dyes were pure according to thin layer chromatograms and ionograms that were obtained.

EXAMPLES 84 and 85

Examples 84 and 85 illustrate bridged dyes.

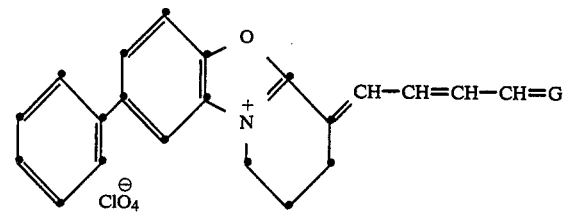

EXAMPLE 84

3'-Methyl-5-phenyl-3,8-trimethyleneoxatelluradicarbocyanine perchlorate

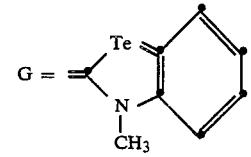

$C_{29}H_{25}ClN_2O_5Te$
mw=644.58

1,2,3-Trihydro-4-(3-methoxy-2-propen-1-ylidene)-8-phenylpyrido[2,1-b]benzoxazolium p-toluenesulfonate (0.85 g, 0.002 mole), 2,3-dimethylbenzotellurazolium trifluoromethanesulfonate (Example 30) (0.75 g, 0.002 mole), and triethylamine (0.4 g) were added in order to acetonitrile (about 30 ml) and stirred for 30 minutes. The dye which precipitated was isolated by filtration, washed with acetone, and dried. Yield 0.55 g. The dye was dissolved in hot methanol (about 75 ml) and filtered. The filtrate was treated with an aqueous solution of tetrabutylammonium perchlorate. After chilling, the solid dye was isolated by filtration and dried. Yield 0.40 g. A 0.30 g sample of dye was recrystallized again from methanol. Yield 0.25 g.
λ-max (methanol)=646 nm
ε-max=17.6×10⁴

EXAMPLE 85

1-Methyl-5'-phenyl-3',8'-trimethylenenaphtho[1,2-d]tellurazolooxadicarbocyanine Perchlorate

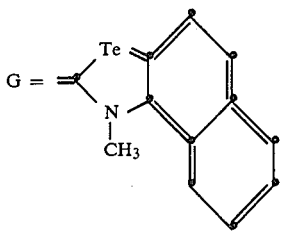

$C_{33}H_{27}ClN_2O_5Te$
mw=694.64

This dye was prepared in a manner analogous to that of Example 84 except that 1,2-dimethylnaphtho[1,2-d]tellurazolium trifluoromethanesulfonate (Example 60) was used in place of the 2,3-dimethylbenzotellurazolium salt. Except for λmax and εmax determinations, the dye was kept in the dark to insure its stability.
λ-max=670 nm (5% m-cresol/95% methanol)
ε-max=17.22×10⁴*

EXAMPLE 86

2-(2-Ethoxyvinyl)-3,5-dimethylbenzotellurazolium Trifluoromethanesulfonate $C_{14}H_{16}F_3NO_4STe$
mw=478.95

2,3,5-Trimethylbenzotellurazolium trifluoromethanesulfonate (Example 33) (0.84 g, 0.002 mole) was dissolved in m-cresol (1 ml). Triethoxymethane (0.89 g, 0.006 mole) was added, and the reaction mixture was heated in a 140° C. oil bath for five minutes. After cooling, diethyl ether (25 ml) was added with stirring. The solid was isolated by filtration, washed with diethyl ether, and dried at 40° C. under vacuum. Yield 0.85 g (89% of theory). The nuclear magnetic resonance spectra of the sample were in agreement with that expected for the structural formula.

EXAMPLES 87-90

Examples 87 through 90 illustrate hemicyanine dyes:

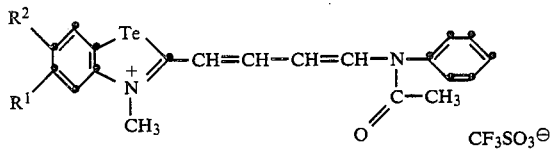

EXAMPLE 87

2-(4-Acetanilido-1,3-butadienyl)-3-methylbenzotellurazolium Trifluoromethanesulfonate, $R^1=R^2=H$ $C_{23}H_{23}F_3N_2O_6STe$
mw=640.11

EXAMPLE 88

2-(4-Acetanilido-1,3-butadienyl)-5,6-dimethoxy-3-methylbenzotellurazolium Trifluoromethanesulfonate, $R^1=R^2=OCH_3$ $C_{25}H_{27}F_3N_2O_8STe$
mw=700.17

EXAMPLE 89

2-(4-Acetanilido-1,3-butadienyl)-5-methoxy-3-methylbenzotellurazolium Trifluoromethanesulfonate, $R^1=OCH_3, R^2=H$ $C_{24}H_{25}F_3N_2O_7STe$
mw=670.14

The foregoing three dyes, Examples 87 through 89 were prepared by the same general procedure. The appropriately substituted, 2,3-dimethylbenzotellurazolium trifluoromethanesulfonate (1 equivalent) and anilinoacrolein anil hydrochloride (2 equivalents) were suspended in acetic anhydride (about 25 ml/gram benzotellurazolium salt) and heated at reflux for five to ten minutes. After cooling and diluting with diethyl ether, the crude product was isolated by filtration, washed with diethyl ether, and dried. Purification was by recrystallization from methanol. The purity of the dyes was checked by thin layer chromatography and ionography. Ultraviolet-visible, nuclear magnetic resonance, and mass spectra were in agreement with that expected for the structural formulae. The C, H, N, F, S, and Te elemental analyses of Example 87 also were in agreement with the structural formula.

The following example illustrates the preparation of a styryl dye.

EXAMPLE 90

2-(4-Dimethylaminostyryl)-3-methylbenzotellurazolium Trifluoromethanesulfonate $C_{19}H_{19}F_3N_2O_3STe$
mw=540.03

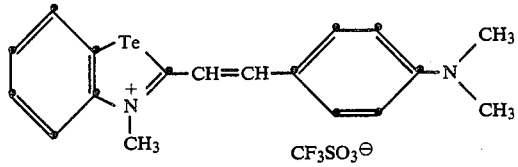

2,3-Dimethylbenzotellurazolium trifluoromethanesulfonate (Example 30) (0.80 g, 0.002 mole) and 4-dimethylaminobenzaldehyde (0.30 g, 0.002 mole) were heated together in ethanol (about 30 ml), with one drop of piperidine present, to boiling and maintained at boiling for ten minutes. An intense red color developed. The dye separated as crystals on cooling. After overnight chilling they were isolated by filtration and recrystallized from ethanol, using diethyl ether to aid in reprecipitation. Yield 0.21 g (19% of theory).
λ-max=541 nm
ε-max=5.94×10⁴

EXMPLES 91-95

Examples 91 through 95 illustrate the preparation of merocyanine dyes.

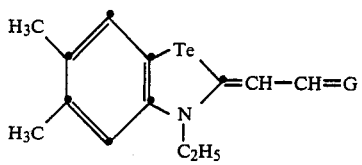

EXAMPLE 91

3-Ethyl-5-[(3-ethyl-5,6-dimethyl-2-benzotellurazolinylidene)ethylidene]rhodanine

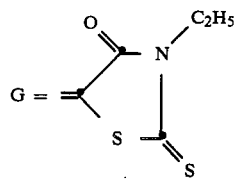

$C_{18}H_{20}N_2OS_2Te$
mw = 472.30

2-(2-Ethoxyvinyl)-3-ethyl-5,6-dimethylbenzotellurazolium trifluoromethanesulfonate (prepared by a procedure analogous to that of Example 86) (1.0 g, 0.002 mole) and 3-ethyl rhodanine (0.40 g, 0.0025 mole) were dissolved in dimethylformamide (15 ml), and triethylamine (0.30 ml) in dimethylformamide (2 ml) was added slowly with stirring. Stirring was continued for five minutes during which time the dye precipitated to form a thick slurry. The slurry was diluted with methanol, and the solid was isolated by filtration. The solid was washed with methanol until all of the blue symmetrical carbocyanine dye, formed as a by-product, was removed. The solid was air dried. Yield 0.31 g. The dye was purified by recrystallization from hot dimethylformamide (about 25 ml). Yield 0.23 g (24% of theory)
λ-max (10% m-cresol/90% methanol) = 551 nm
ε-max = 8.39 × 10$^4$

EXAMPLE 92

3-Ethyl-5-[(3-ethyl-5,6-dimethyl-2-benzotellurazolinylidene)ethylidene]-1-phenyl-2-thiohydantoin

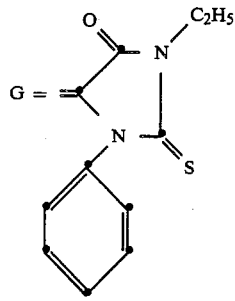

$C_{24}H_{25}N_3OSTe$
mw = 530.78

2-(2-Ethoxyvinyl)-3-ethyl-5,6-dimethylbenzotellurazolium trifluoromethylsulfonate (prepared by a procedure analogous to that of Example 86) (1.0 g, 0.002 mole) and 3-ethyl-1-phenyl-2-thiohydantoin (0.50 g, 0.0025 mole) were dissolved in warm acetonitrile (5 ml). Tetramethylguanidine (0.35 ml) in acetonitrile (2 ml) was added slowly. The solution turned red immediately and crystals formed quickly. After stirring for 15 minutes at room temperature, the solid was isolated by filtration, washed with acetonitrile and recrystallized from 5 ml m-cresol by adding 10 ml of methanol.
λ-max (10% m-cresol/90% methanol) = 539 nm
ε-max = 7.01 × 10$^4$

EXAMPLE 93

4-[(3-Ethyl-5,6-dimethyl-2-benzotellurazolinylidene)ethylidene]-3-methyl-1-phenyl-2-pyrazolin-5-one

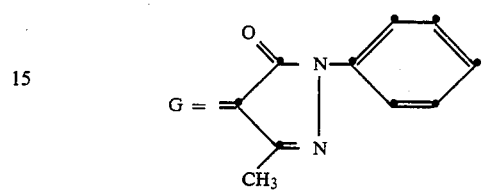

$C_{23}H_{23}N_3OTe$
mw = 484.79

2-(2-Ethoxyvinyl)-3-ethyl-5,6-dimethylbenzotellurazolium trifluoromethylsuflonate (prepared by a procedure analogous to that of Example 86) (1.0 g, 0.002 mole) and 3-methyl-1-phenyl-2-pyrazolin-5-one (0.40 g, 0.0025 mole) were dissolved in dimethylformamide. Triethylamine (0.30 ml) in dimethylformamide (2 ml) was added slowly. Red-orange color formed immediately. After 30 minutes stirring at room temperature, water (about 8 ml) was added. The solid dye which formed was isolated by filtration and air dried. It was recrystallized from toluene. Yield 0.31 g (32% of theory).
λ-max (10% m-cresol/90% methanol = 518 nm
ε-max = 7.17 × 10$^4$

EXAMPLE 94

1,3-Diethyl-5-[(3-ethyl-5,6-dimethyl-2-benzotellurazolinylidene)ethylidene]barbituric Acid

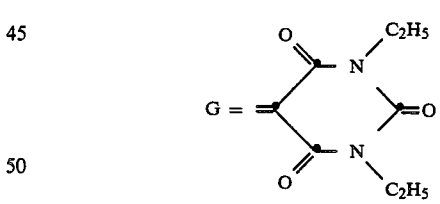

$C_{21}H_{25}N_3O_3Te$
mw = 494.79

2-(2-Ethoxyvinyl)-3-ethyl-5,6-dimethylbenzotellurazolium trifluoromethylsulfonate (prepared by a procedure analogous to that of Example 86) (1.0 g, 0.002 mole) and 1,3-diethylbarbituric acid were dissolved in dimethylformamide (10 ml). Triethylamine (0.30 ml) in dimethylformamide (2 ml) was added slowly. A thick slurry formed which was diluted with methanol (20 ml). The solid was isolated by filtration, washed with methanol until the green color disappeared. The solid dye was recrystallized from hot dimethylformamide (35 ml). Yield 0.38 g (39% of theory).
λ-max (10% m-cresol/90% methanol) = 504 nm
ε-max = 7.30 × 10$^4$

EXAMPLE 95

1,3-Diethyl-5-[(3-ethyl-5,6-dimethyl-2-benzotellurazolinylidene)ethylidene]-2-thiobarbituric acid

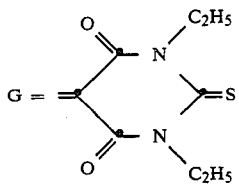

$C_{21}H_{25}N_3O_2STe$
mw = 510.77

This dye was prepared in the same way as the dye of Example 94 except that 1,3-diethyl-2-thiobarbituric acid (0.44 g, 0.0022 mole) was used in place of 1,3-diethylbarbituric acid. The crude solid dye was slurried in hot methanol (200 ml) and filtered again before being recrystallized. Yield 0.38 g (37% of theory).
λ-max (10% m-cresol/90% methanol)—524 nm
ε-max = 7.97 × 10⁴

EXAMPLES 96–98

Examples 96 through 98 illustrate the preparation of hemicyanine dyes that are readily converted to merocyanine dyes.

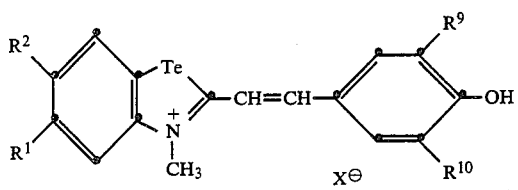

EXAMPLE 96

2-(4-Hydroxystyryl)-3-methylbenzotellurazolium Trifluoromethanesulfonate, $R^1=R^2=R^9=R^{10}=H$, $X=CF_3SO_3$ $C_{17}H_{14}F_3NO_4STe$
mw = 512.97

2,3-Dimethylbenzotellurazolium trifluoromethanesulfonate (Example 30) (1.43 g, 0.0035 mole) and 4-hydroxybenzaldehyde (0.85 g, 0.007 mole) were combined with enough ethanol to make a uniform slurry and heated in an open vessel in an oil bath at 120° C. for three and a half hours. After removing from heat, the red viscous mass was treated with ethanol (2–3 ml). The crystalline solid was isolated by filtration. Yield 0.96 g. The solid was recrystallized from ethanol (125 ml). Yield 0.61 g (35% of theory). The dye was pure according to thin layer chromatograms and an ionogram.

EXAMPLE 97

2-(4-Hydroxystyryl)-3,5,6-trimethylbenzotellurazolium Trifluoromethanesulfonate, $R^1=R^2=CH_3$, $R^9=R^{10}=H$, $X=CF_3SO_3$ $C_{19}H_{18}F_3NO_4STe$
mw = 541.00

This dye was prepared in the same way and on the same scale as that of Example 96, except that 2,3,5,6-tetramethylbenzotellurazolium trifluoromethanesulfonate (Example 34) was used in place of the 2,3-dimethylbenzotellurazolium compound. The reaction time was six hours. Yield 0.86 g (45% of theory). The dye was pure according to thin layer chromatograms and an ionogram.

EXAMPLE 98

2-(3,5-Di-t-butyl-4-hydroxystyryl)-3-methylbenzotellurazolium Trifluoromethanesulfonate, $(R^1=R^2=H, R^9=R^{10}=t-C_4H_9, X=CF_3SO_3$ $C_{25}H_{30}F_3NO_4STe$
mw = 625.18

This dye was prepared in the same way as that of Example 96 except that 2-methyoxyethanol was used as solvent and 3,5-di-tert-butyl-4-hydroxybenzaldehyde was used in place of 4-hydroxybenzaldehyde. The reaction time was 24 hours. The dye was recrystallized twice from isopropanol to yield a sample that was pure according to the thin layer chromatograms and an ionogram.

The three dyes of Examples 96 through 98 were observed to be easily converted in solution in the presence of base such as triethylamine to a merocyanine by the loss of hydrogen trifluoromethanesulfonate. In the next three examples the dyes were isolated in the merocyanine form. The conversion to merocyanine of all six hydroxy styryl dyes of Examples 96 through 101 is easily and completely reversible by the addition of acid to the solutions of the dyes.

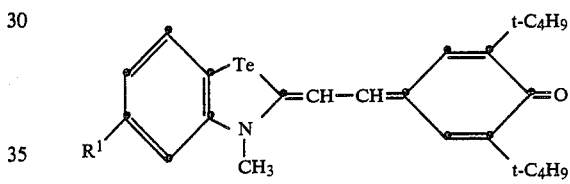

EXAMPLE 99

2,6-Di-tert-butyl-4-[2-(5-methoxy-3-methylbenzotellurazolinylidene)ethylidene]-2,5-cyclohexadien-1-one, $R^1=OCH_3$ $C_{25}H_{31}NO_2Te$
mw = 504.76

This dye was prepared in the same way as that of Example 98, except that 5-methoxy-2,3-dimethylbenzotellurazolium trifluoromethanesulfonate (Example 32) was used in place of 2,3-dimethylbenzotellurazolium trifluoromethanesulfonate, up to the point where the crude product was redissolved in isopropanol. Triethylamine was added to the solution. After chilling, the crystals were isolated by filtration. The example was recrystallized once more from acetonitrile. Yield 17% of theory.
λ-max (methanol) = 584 nm
ε-max = 6.56 × 10⁴

EXAMPLE 100

2,6-Di-tert-butyl-4-[2-(3-methyl-5-methylthiobenzotellurazolinylidene]-2,5-cyclohexadien-1-one, $R^1=SCH_3$ $C_{25}H_{31}NOSTe$
mw = 520.82

2,3-Dimethyl-5-methylthiobenzotellurazolium trifluoromethanesulfonate (Example 35) (1.38 g, 0.0030 mole and 3,5-di-tert-butyl-4-hydroxybenzaldehyde (0.85, 0.0030 mole) were suspended in 2-methoxyethanol (20 ml). The reaction mixture was heated in an oil bath at 120° C. for 20 hours. The mixture turned orange after five minutes, and crystals began to appear after 90 minutes. After chilling, the solid was isolated by filtration, washed with diethyl ether and dissolved in boiling acetonitrile (175 ml) (plus three drops of hydrochloric acid), and filtered by gravity. Triethylamine (0.5 g) was added to the filtrate. The purple solution was chilled. The solid was isolated by filtration and dried. Yield 1.0 g (64% of theory). The dye was pure according to thin layer chromatograms and ionograms.
λ-max (methanol)=581 nm
ε-max=9.06×10$^4$

EXAMPLE 101

2,6-Di-tert-butyl-4-[2-(5-hydroxy-3-methylbenzotellurazolinylidene)ethylidene]-2,5-cyclohexadien-1-one, R$^1$=OH $C_{24}H_{29}NO_2Te$
mw=490.83

This dye was prepared in the same way and on the same scale as that of Example 100, except that 5-hydroxy-2,3-dimethylbenzotellurazolium trifluoromethanesulfonate (Example 36) was used in place of 2,3-dimethyl-5-methylthiobenzotellurazolium trifluoromethanesulfonate. Yield 1.07 g (72% of theory). The dye was pure according to thin layer chromatograms and ionograms.
λ-max (methanol)=586 nm
ε-max=5.66×10$^4$ Examples 102 through 104 illustrate the antifoggant activity of the 3-alkyl-2-methylbenzotellurazolium salts.

EXAMPLES 102-104

The antifoggant activity of 2,3-dimethylbenzotellurazolium trifluoromethanesulfonate, 1, (Example 30) is illustrated and compared with that of analogous chalcogenazolium salts and with that of quaternary salt 4, a known antifoggant.

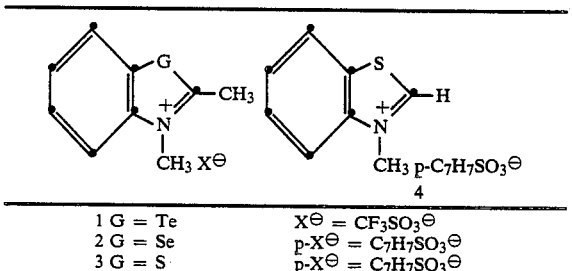

| | | |
|---|---|---|
| 1 G = Te | X$^\ominus$ = CF$_3$SO$_3^\ominus$ | |
| 2 G = Se | p-X$^\ominus$ = C$_7$H$_7$SO$_3^\ominus$ | |
| 3 G = S | p-X$^\ominus$ = C$_7$H$_7$SO$_3^\ominus$ | |

These compounds were evaluated in a sulfur plus gold sensitized silver bromoiodide emulsion. The compounds were added at the levels indicated in Table II and coated on a cellulose acetate support to achieve a silver coverage of 4.9 g/m$^2$ and a gelatin coverage of 11.1 g/m$^2$. Samples of the coatings were exposed to a tungsten light source in an Eastman 1B sensitometer through a wedge spectrograph. The coatings were developed for five minutes in a hydroquinone-Elon ® (N-methylaminophenol hemisulfate) developer, fixed, washed, and dried. Additional samples of each of the coatings were incubated for two weeks at 49° C. under 50% relative humidity before being exposed and processed as described above. A characteristic curve was plotted for each coating. The sensitivity and fog (D-min) data were determined from these curves and are presented in Table II.

TABLE II

Antifoggant Activity of 2,3-Dimethylchalcogenazolium Salts

| Compound | Level mmole/ mole Ag | Relative Sensitivity and Fog | | | |
|---|---|---|---|---|---|
| | | Fresh | Fog | Incubation | Fog |
| Control | — | 100 | 0.10 | 59 | 0.49 |
| 1 | 0.05 | 95 | 0.08 | 59 | 0.28 |
| | 0.10 | 87 | 0.09 | 67 | 0.20 |
| | 0.30 | 91 | 0.07 | 74 | 0.10 |
| 2 | 0.05 | 95 | 0.08 | 39 | 0.41 |
| | 0.10 | 94 | 0.07 | 69 | 0.35 |
| | 0.30 | 89 | 0.07 | 89 | 0.25 |
| 3 | 0.05 | 97 | 0.09 | 53 | 0.46 |
| | 0.10 | 95 | 0.08 | 50 | 0.44 |
| | 0.30 | 102 | 0.09 | 55 | 0.41 |
| 4 | 0.05 | 95 | 0.09 | 63 | 0.41 |
| | 0.10 | 89 | 0.08 | 58 | 0.28 |
| | 0.30 | 82 | 0.07 | 76 | 0.15 |

As shown by Table II the tellurazolium salt produced lower minimum densities on incubation than the comparison antifoggants. Viewed another way, it can be seen that half the concentration of tellurazolium salt reduced Dmin on incubation to the level observed with 0.10 mmol of 4, which is a known highly effective antifoggant.

EXAMPLE 105

This example shows that the antifoggant activity of the compound of Example 30 is a property of other benzotellurazolium salts as well and also of naphtho[1,2-d]tellurazolium salts. The compounds were evaluated in the same way as those of Examples 102 through 104. The results are presented in Table III.

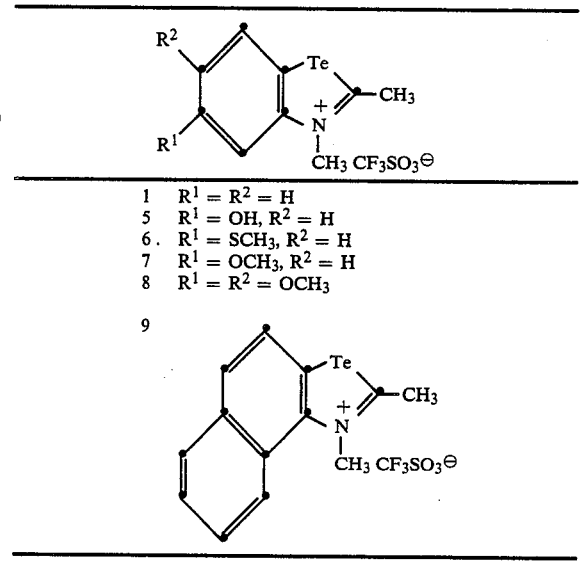

| | |
|---|---|
| 1 | R$^1$ = R$^2$ = H |
| 5 | R$^1$ = OH, R$^2$ = H |
| 6. | R$^1$ = SCH$_3$, R$^2$ = H |
| 7 | R$^1$ = OCH$_3$, R$^2$ = H |
| 8 | R$^1$ = R$^2$ = OCH$_3$ |

9

TABLE III

Antifoggant Activity of Other Tellurazolium Salts

| Compound | Level mmole mole Ag | Relative Speed and Fog | | | |
|---|---|---|---|---|---|
| | | Fresh | Fog | Incubated | Fog |
| Control | — | 100 | 0.11 | 50 | 0.62 |
| 1 | 0.01 | 95 | 0.13 | 60 | 0.57 |
| | 0.10 | 85 | 0.09 | 78 | 0.22 |
| | 0.30 | 71 | 0.09 | 54 | 0.10 |
| 5 | 0.01 | 100 | 0.12 | 33 | 0.56 |
| | 0.10 | 74 | 0.12 | 80 | 0.21 |

TABLE III-continued
Antifoggant Activity of Other Tellurazolium Salts

| Compound | Level mmole mole Ag | Relative Speed and Fog | | | |
|---|---|---|---|---|---|
| | | Fresh | Fog | Incubated | Fog |
| | 0.30 | 43 | 0.13 | 39 | 0.12 |
| 6 | 0.01 | 89 | 0.10 | 47 | 0.48 |
| | 0.10 | 74 | 0.08 | 68 | 0.18 |
| | 0.30 | 52 | 0.07 | 35.5 | 0.10 |
| 7 | 0.01 | 97 | 0.10 | 39 | 0.48 |
| | 0.10 | 78 | 0.08 | 69 | 0.13 |
| | 0.30 | 52 | 0.08 | 49 | 0.10 |
| 8 | 0.01 | 100 | 0.12 | 67 | 0.45 |
| | 0.10 | 78 | 0.10 | 68 | 0.16 |
| | 0.30 | 50 | 0.07 | 45 | 0.10 |
| 9 | 0.01 | 95 | 0.11 | 57 | 0.48 |
| | 0.10 | 80 | 0.08 | 80 | 0.17 |
| | 0.30 | 52 | 0.06 | 39 | 0.09 |

Examples 106 through 110 illustrate the utility of the dyes of this invention as spectral sensitizers of silver halide photographic emulsions.

EXAMPLES 106–108

The dyes of Examples 69, 70, and 78 were tested in a 0.2 μm sulfur and gold sensitized, monodispersed gelatino-silver bromide emulsion containing 2.5 mole % iodide, based on silver. The dyes were added to separate portions of the emulsions at the concentrations indicated, and the resulting mixtures were coated to obtain silver coverage of 1.07 g/m² and a gelatin coverage of 7.32 g/m² on a cellulose ester support. A portion of each coating was exposed in a spectral sensitometer to a quartzhalogen light source through a Wratten ® 80B color correcting filter, diffraction grating with filters to remove second order transmission, and through a superimposed step wedge. The coatings were developed in a Kodak X-omat ® processor for 80 sec at 35° C. in a Kodak Rapid ® X-ray developer, fixed, washed, and dried. A characteristic (D log E) curve was determined for each coating at 400 nm and at each 10 nm interval between 400 nm and 700 nm. The speed at 0.3 density units above fog was read from each characteristic curve, adjusted for a uniform energy distribution over the spectral range, and plotted against wavelength to obtain a relative log spectral sensitivity curve. The sensitizing maximum and the relative speed at the sensitizing maximum for each dye was determined from this curve.

The results of these tests are summarized in Table IV. The levels are expressed as (moles of dye per mole of silver)×10⁴. (For example, the dye of Example 69 was present at 0.0008 mole/mole Ag.) Sensitivity maxima and ranges are expressed in nanometers.

TABLE IV

| Dye | Level | Rel. Sens. (400 nm) | Sens. (Max) | Sens. Range (nm) |
|---|---|---|---|---|
| Undyed | — | 100 | — | to 490 |
| Example 69 | 8.0 | 234 | 570 | 490 to 620 |
| Example 70 | 8.0 | 118 | 620 | 490 to 680 |
| Example 78 | 6.0 | 159 | 630 | 490 to 690 |

EXAMPLE 109

The following dyes were evaluated in the same way as the dyes tested in Examples 106 through 108. The results of these tests are summarized in Table V.

TABLE V

| Dye Example No. | Level | Rel. Sens. (400 nm) | Sens. Max (nm) Primary | Sens. Max (nm) Secondary | Sens. Range (nm) |
|---|---|---|---|---|---|
| Control | — | 100 | — | — | to 490 |
| 63 | 8.0 | 69 | 650 | — | 580–690 |
| 64 | 6.0 | 74 | 670 | — | 610–700 |
| 74 | 6.0 | 347 | 590 | 550 | 470–650 |
| 75 | 6.0 | 224 | 640 | — | 500–700 |
| 76 | 8.0 | 182 | 570 | — | 460–620 |
| 77 | 8.0 | 191 | 570 | — | 480–630 |
| 79 | 8.0 | 219 | 670 | — | 550–720 |
| 80 | 8.0 | 204 | 570 | 540 | 460–630 |
| | 2.0 | 263 | 570 | 550 | 490–590 |
| 81 | 6.0 | 178 | 590 | 550 | 470–650 |
| | 8.0 | 148 | 590 | 550 | 460–670 |
| 82 | 6.0 | 123 | 610 | — | 480–660 |
| 83 | 2.0 | 123 | 640 | — | 560–700 |
| | 6.0 | 40 | 640 | — | 560–690 |
| 84 | 6.0 | 126 | 680 | 640 | 550–740 |
| 85 | 8.0 | 151 | 700 | 730 | 680–750 |
| 92 | 8.0 | 170 | 540 | 510 | 440–620 |
| 93 | 8.0 | 269 | 520 | — | 440–560 |

EXAMPLE 110

The three dyes identified below were selected for investigation of infrared sensitizing properties in an internal latent image forming silver halide emulsion. The solution absorption maxima of the three dyes in methanol ranged from 686 nm to 721 nm.

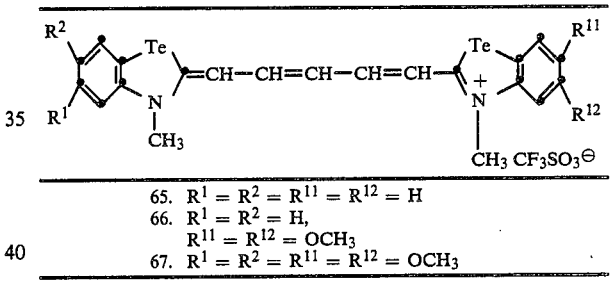

65. $R^1 = R^2 = R^{11} = R^{12} = H$
66. $R^1 = R^2 = H,$
    $R^{11} = R^{12} = OCH_3$
67. $R^1 = R^2 = R^{11} = R^{12} = OCH_3$

The emulsion used in these examples was a 0.25 μm cubic internal latent image forming silver bromide core-shell emulsion in which the core was sulfur and gold sensitized and the surface was unsensitized. The dyes were added to separate portions of the emulsion at the levels indicated in Tables VI and VII. Each portion was divided so that one also contained an addenda package of composition below and one did not. The amount of each component in the addenda package is expressed in grams/mole Ag.

Addenda Package 65.5 g—Dispersion of 5.07% 2,5-dioctylhydroquinone in 7.6% gelatin
0.5 g—Triazine stilbene sulfonic acid supersensitizer
2.0 g—4-hydroxy-6-methyl-1,3,3A,7-tetraazaindene, sodium salt The several portions of the emulsion were each coated on cellulose acetate film support to achieve silver coverage of 1.8 g/m² and gelatin coverage of 4.3 g/m². A portion of each coating was exposed in a spectral sensitometer, to a tungsten light source in both the visible and infrared region through a diffraction grating, with filters to remove second order transmission, and a continuous step wedge. Another portion was exposed to a tungsten lamp at 3000° K. through a Wratten ® 87 filter (which combination transmits radiation at wavelengths of 735 nm or longer). Still another portion was exposed to the 365 nm mercury emission line using a mercury lamp and a Wratten ® 18A filter. The coatings were developed twelve minutes in Kodak Rapid X-ray ® developer (which also contained in addition potassium iodide) at room temperature, fixed, washed, and dried.

Table VI contains a summary of the relative intrinsic sensitivities (from the 365 nm line exposures) and the relative infrared sensitivities from the 3000° K. Wratten ® 87 exposure).

Results in Table VII demonstrate that all three dyes spectrally sensitize. The photographic response in coatings containing the addenda was better than in coatings without the addenda.

Table VII contains a summary of spectral sensitizing data.

TABLE VI

| | | Relative Sensitivities | | | |
|---|---|---|---|---|---|
| | | Intrinsic | | Infrared | |
| Dye | mole/ mole Ag | No Addenda | With Addenda | No Addenda | With Addenda |
| Undyed | — | 100 | 74 | — | — |
| 65 | 1.0 × 10⁻⁴ | 49 | 68 | 100 | 562 |
| 66 | 1.0 × 10⁻⁴ | 46 | 59 | 339 | 1132 |
| 67 | 4.0 × 10⁻⁴ | 6.8 | 3.6 | 71 | 95 |

TABLE VII

| | | | Sens. Max (nm) | | Sens. Range (nm) | |
|---|---|---|---|---|---|---|
| Dye | λmax (MeOH) (nm) | Level × 10⁴ | No Addenda | With Addenda | No Addenda | With Addenda |
| 65 | 686 | 1.0 | 730 | 745 | 640–790 | 600–810 |
| 66 | 703 | 1.0 | 740 | 765 | 590–800 | 570–840 |
| 67 | 721 | 4.0 | 760 | 775 | 695–785 | 580–820 |

EXAMPLES 111 TO 508

Using preparation procedures similar to those already described a variety of tellurocyanine dyes were synthesized having differing tellurazolium nuclei, methine linkages, or coupled azolinylidene (which in some instances were tellurazolinylidene nuclei) or azinylidene nuclei. The wavelength of absorption of each dye was measured in methanol, and the wavelength of maximum absorption was noted. Absorption maxima wavelengths are reported in nanometers. In some instances the dyes correspond to dyes previously exemplified.

Tellurazole ion nuclei fragments, identified by letters, are listed below.

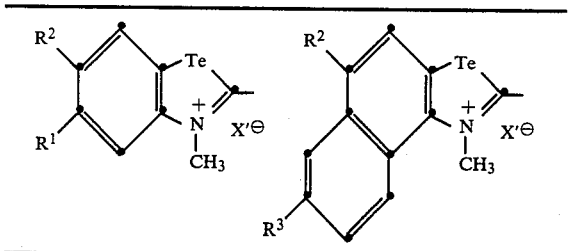

| A | $R^1 = R^2 = H$ |
|---|---|
| B | $R^1 = CH_3, R^2 = H$ |
| C | $R^1 = R^2 = CH_3$ |
| D | $R^1 = SCH_3, R^2 = H$ |
| E | $R^1 = OCH_3, R^2 = H$ |
| F | $R^1 = OH, R^2 = H$ |
| G | $R^1 = R^2 = OCH_3$ |

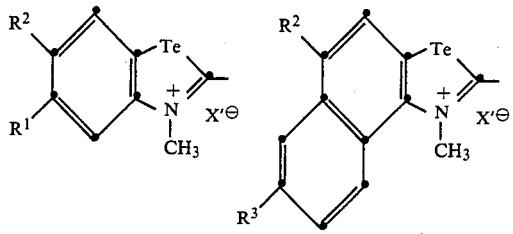

| H | $R^2 = R^3 = H$ |
|---|---|
| I | $R^2 = CH_3, R^3 = OCH_3$ |
| J | $R^2 = H, R^3 = OCH_3$ |

The other heterocyclic nucleus used to complete each cyanine dye structure is listed below by number in the left hand column.

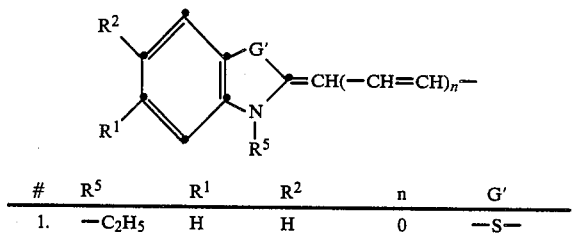

| # | $R^5$ | $R^1$ | $R^2$ | n | G' |
|---|---|---|---|---|---|
| 1. | —C₂H₅ | H | H | 0 | —S— |
| 3. | —C₂H₅ | H | H | 1 | —O— |
| 4. | —CH₃ | H | H | 1 | >C(CH₃)₂ |
| 5. | —CH₃ | H | H | 1 | —S— |
| 6. | —C₂H₅ | H | H | 1 | —S— |
| 7. | —C₂H₅ | H | H | 1 | —Se— |
| 13. | —CH₃ | H | H | 1 | —Te— |
| 14. | —CH₃ | —CH₃ | H | 1 | —Te— |
| 15. | —CH₃ | —CH₃ | —CH₃ | 1 | —Te— |
| 16. | —CH₃ | —SCH₃ | H | 1 | —Te— |
| 17. | —CH₃ | —OCH₃ | H | 1 | —Te— |
| 18. | —CH₃ | —OH | H | 1 | —Te— |
| 19. | —CH₃ | —OCH₃ | —OCH₃ | 1 | —Te— |
| 24. | —CH₃ | H | H | 2 | >C(CH₃)₂ |
| 25. | —CH₃ | H | H | 2 | —S— |
| 26. | —C₂H₅ | H | H | 2 | —S— |
| 27. | —C₂H₅ | H | H | 2 | —Se— |
| 30. | —CH₃ | H | H | 2 | —Te— |
| 34. | —CH₃ | —CH₃ | H | 2 | —Te— |
| 35. | —CH₃ | —CH₃ | —CH₃ | 2 | —Te— |
| 36. | —CH₃ | —SCH₃ | H | 2 | —Te— |
| 37. | —CH₃ | —OCH₃ | H | 2 | —Te— |
| 38. | —CH₃ | —OH | H | 2 | —Te— |
| 39. | —CH₃ | —OCH₃ | —OCH₃ | 2 | —Te— |

2. 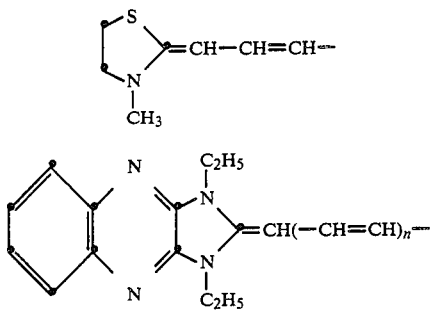

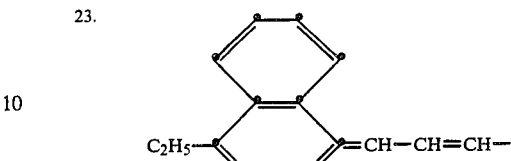

| 8. | n = 1 |
| 31. | n = 2 |

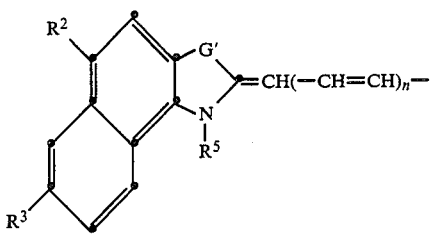

| # | R⁵ | R² | R³ | n | G' |
|---|---|---|---|---|---|
| 9. | —CH₃ | H | H | 1 | —S— |
| 10. | —C₂H₅ | H | H | 1 | —S— |
| 20. | —CH₃ | H | H | 1 | —Te— |
| 21. | —CH₃ | —CH₃ | H | 1 | —Te— |
| 22. | —CH₃ | H | —OCH₃ | 1 | —Te— |
| 28. | —CH₃ | H | H | 2 | —S— |
| 29. | —C₂H₅ | H | H | 2 | —S— |
| 40. | —CH₃ | H | H | 2 | —Te— |
| 41. | —CH₃ | —CH₃ | H | 2 | —Te— |
| 42. | —CH₃ | H | —OCH₃ | 2 | —Te— |

| | R⁵ | n |
|---|---|---|
| 11. | —CH₃ | 1 |
| 12. | —C₂H₅ | 1 |
| 32. | —CH₃ | 2 |
| 33. | —C₂H₅ | 2 |

23.

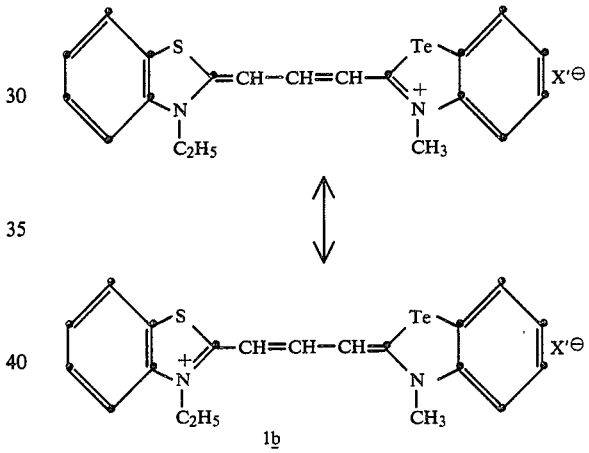

In tabulating the dyes by their composite structural fragments the fragments A-J in the quaternary form (with an associated positive change) and the numbered fragments are shown in the uncharged form. It is to be understood that a cyanine dye should be considered as a resonance hybrid of two (or more) structures and that the positive charge is not actually localized on any one part of the dye molecule. For example, dye 6A of the table can be considered as a hybrid of two structures 1a and 1b. Hence, it would be just as correct to show the positive charge on the numbered fragments and to show the fragments A-J in the uncharged form.

TABLE VIII

Telluracyanine Dye Absorption Maxima in Methanol

| # | A | B | C | D | E | F | G | H | I | J |
|---|---|---|---|---|---|---|---|---|---|---|
| 1 | 438 | 442 | 445 | 447 | 448 | 449 | 457 | 461 | 465 | 466 |
| 2 | 523 | 528 | 532 | 533 | 534 | 533 | 543 | 550 | 548 | 558 |
| 3 | 539 | 543 | 546 | 549 | 551 | 552 | 557 | 564 | 569 | 573 |
| 4 | 564 | 568 | 569 | 574 | 576 | 577 | 580 | 592 | 597 | 598 |
| 5 | 569 | 582 | 583 | 587 | 589 | 592 | 598 | 602 | 606 | 607 |
| 6 | 578 | 584 | 587 | 588 | 590 | 593 | 597 | 603 | 610 | 610 |
| 7 | 583 | 590 | 589 | 594 | 596 | 593 | 604 | 610 | 614 | 616 |
| 8 | 592 | 597 | 601 | 603 | 603 | 605 | 594 | 617 | 621 | 624 |
| 9 | 592 | 603 | 604 | 607 | 606 | 603 | 615 | 620 | 624 | 625 |
| 10 | 597 | 602 | 603 | 603 | 607 | 608 | 614 | 620 | 625 | 627 |
| 11 | 600 | 609 | 612 | 619 | 609 | 615 | — | 619 | 625 | 628 |
| 12 | 600 | 605 | 609 | 609 | 611 | 610 | — | 622 | 627 | 629 |
| 13 | 601 | 607 | 609 | 613 | 613 | 615 | 620 | 628 | 631 | 633 |
| 14 | 607 | 608 | 615 | 617 | 612 | 623 | — | — | — | 635 |
| 15 | 609 | 612 | 614 | 617 | 616 | 615 | 625 | — | — | — |
| 16 | 613 | 615 | 617 | 621 | 623 | 620 | 627 | 623* | 628 | 632 |
| 17 | 613 | 617 | 616 | 623 | 622 | — | 629 | 638 | 641 | 643 |
| 18 | 615 | 610 | 615 | 620 | — | — | — | — | — | 636 |
| 19 | 620 | 623 | 625 | 627 | 629 | 631 | 635 | 636 | 643 | 644 |
| 20 | 628 | — | — | 623 | 638 | — | 636 | 653 | 656 | 658 |
| 21 | 631 | — | — | 628 | 641 | — | 643 | 656 | 658 | 660 |

TABLE VIII-continued

Telluracyanine Dye Absorption Maxima in Methanol

| # | A | B | C | D | E | F | G | H | I | J |
|---|---|---|---|---|---|---|---|---|---|---|
| 22 | 633 | 635 | — | 632* | 643 | — | 644 | 658 | 660 | 663 |
| 23 | 650 | 657 | 663 | 655* | 659 | 648* | 677 | 671 | 682 | 703 |
| 24 | 660 | 663 | 663 | 669 | 686* | 664 | 681 | 688 | 689 | 693 |
| 25 | 667 | 663 | 660 | 674 | 675 | 667 | 688 | 696 | 699 | 701 |
| 26 | 671 | 664* | 663* | 678 | 680 | 665* | 690 | 696 | 703 | 703 |
| 27 | 671 | 674 | 676 | 679 | 669 | 676 | 687 | 700 | 705 | 707 |
| 28 | 688 | 693 | 694 | 694 | 697 | 690 | 697 | 712 | 716 | 717 |
| 29 | 688 | 693 | 693 | 695 | 698 | 694 | 699 | 712 | 716 | 718 |
| 30 | 687 | 694 | 694 | 698 | 698 | 692 | 703 | 712 | 715 | 718 |
| 31 | 693 | 698 | 700 | 703 | 703 | 698 | 711 | 720 | 725 | 728 |
| 32 | 694 | 699 | 705 | 700 | 703 | 700 | 716 | 713 | 719 | 717 |
| 33 | 694 | 700 | 703 | 700 | 701 | 698 | 718 | 713 | 717 | 718 |
| 34 | 692 | 696 | 698 | 699 | 703 | 697 | 708 | 718 | 718 | 721 |
| 35 | 693 | 698 | 702 | 703 | 704 | 696 | 711 | 718 | 717 | 720 |
| 36 | 696 | 700 | 702 | 703 | 706 | 700 | 710 | 723 | 725 | 723 |
| 37 | 698 | 703 | 704 | 706 | 707 | 704 | 713 | 723 | 726 | 728 |
| 38 | 692 | 697 | 698 | 700 | 704 | 705 | 708 | 717 | 721 | 723 |
| 39 | 703 | 708 | 711 | 713 | 713 | 708 | 723 | 728 | 732 | 733 |
| 40 | 712 | 715 | 714 | 723 | 723 | 717 | 728 | 737 | 742 | 744 |
| 41 | 715 | 718 | 719 | 725 | 726 | 721 | 732 | 742 | 745 | 746 |
| 42 | 718 | 723 | 721 | 727 | 728 | 723 | 733 | 744 | 746 | 748 |

*Broad absorption maximum peak

From the foregoing discussion it is apparent that the compounds of this invention can take a variety of forms and be readily applied to a variety of photographic uses. This invention has been described in detail with reference to preferred embodiments thereof, but it will be understood that variations and modifications can be effected within the spirit and scope of the invention.

What is claimed is:

1. A radiation sensitive silver halide emulsion comprised of
   a dispersing medium,
   radiation sensitive silver halide grains, and
   a photographically useful concentration of an addendum containing an aromatic ring and, fused with said aromatic ring, a five membered ring containing a divalent tellurium atom, a nitrogen atom, and a carbon atom interposed between said tellurium and nitrogen atoms.

2. In a photographic element comprised of
   a support,
   coated on said support, at least one silver halide emulsion layer comprised of
      a dispersing medium and
      radiation-sensitive silver halide grains, and
   located to facilitate photographic image formation, an addendum comprised of a chalcogenazole, chalcogenazoline, chalcogenazolinium, or chalcogenazolium heterocyclic ring fused with an aromatic ring,
   the improvement wherein tellurium is a member of said heterocyclic ring.

3. A photographic element according to claim 2 wherein said addendum is present in said element during processing to produce a visible photographic image.

4. A photographic element according to claim 3 wherein said radiation sensitive silver halide grains form a predominantly internal latent image and said addendum is a nucleating agent.

5. A photographic element according to claim 3 wherein said addendum is a 2-alkyl-N-alkynyltellurazolium salt.

6. A photographic element according to claim 5 wherein said alkyl moiety contains from 1 to 6 carbon atoms and said alkynyl moiety contains from 3 to 5 carbon atoms.

7. A photographic element according to claim 6 wherein said alkynyl moiety is a propargyl or 2-butynyl moiety.

8. A photographic element according to claim 3 wherein said addendum contains a hydrazino moiety.

9. A photographic element according to claim 3 wherein said addendum contains a hydrazido moiety.

10. A photographic element according to claim 2 wherein said addendum is present in said photographic element in a stabilizing concentration.

11. A photographic element according to claim 2 wherein said silver halide grains form a predominantly surface latent image and said addendum is present in said photographic element in a speed increasing concentration.

12. A photographic element according to claim 3 wherein said silver halide grains form a predominantly surface latent image and said addendum is present in said photographic element in a contrast increasing concentration.

13. In a photographic element comprised of
    a support,
    coated on said support, at least one silver halide emulsion layer comprised of
       a dispersing medium and
       radiation-sensitive silver halide grains, and located to facilitate photographic image formation, a dye containing an aromatic ring and, fused with said aromatic ring, a five membered ring containing a divalent chalcogen atom, a nitrogen atom, and a carbon atom interposed between said chalcogen and nitrogen atom,
    the improvement comprising said chalcogen atom being a tellurium atom.

14. A photographic element according to claim 13 wherein said dye is located between said silver halide emulsion layer and said support.

15. A photographic element according to claim 13 wherein said dye is located between said silver halide emulsion layer and exposing radiation.

16. A photographic element according to claim 13 wherein said dye is located within said silver halide emulsion layer.

17. A photographic element according to claim 16 wherein said dye is located in said dispersing medium.

18. A photographic element according to claim 17 wherein said dye is adsorbed to surfaces of said silver halide grains.

19. A photographic element according to claim 18 wherein said dye is adsorbed to surfaces of said silver halide grains in an amount sufficient to alter the sensitivity of silver halide grains to radiation.

20. A photographic element according to claim 19 wherein said dye is a sensitizing dye.

21. A photographic element according to claim 20 wherein said dye is a polymethine dye.

22. A photographic element according to claim 21 wherein said dye is a cyanine dye.

23. A photographic element according to claim 20 wherein said dye is capable of extending the sensitivity of silver halide grains to longer wavelengths of electromagnetic radiation.

24. A photographic element according to claim 23 wherein said dye is a green sensitizing dye.

25. A photographic element according to claim 23 wherein said dye is a red sensitizing dye.

26. A photographic element according to claim 23 wherein said dye is an infrared sensitizing dye.

27. A photographic element according to any one of claims 13 through 26 wherein said radiation sensitive silver halide grains form a predominantly surface latent image.

28. A photographic element according to any one of claims 13 through 26 wherein said radiation sensitive silver halide grains form a predominatnly internal latent image.

29. A photographic element according to any one of claims 13 through 26 which is capable of forming a direct positive photographic image.

30. A process of producing a viewable photographic image comprising photographically processing an imagewise exposed photographic element according to claim 2.

31. A photographic element according to claim 1 wherein said five membered fused ring is a tellurazole or tellurazoline ring and said aromatic ring is a carbocyclic aromatic ring.

32. A photographic element according to claim 31 wherein said five membered ring is a tellurazolinylidene ring.

33. A photographic element according to claim 31 wherein said addendum is a benzotellurazole or naphthotellurazole.

34. A photographic element according to claim 33 wherein the benzo or naphtho aromatic ring portion of said benzotellurazole or naphthotelluarazole includes at least one substituent chosen from among aliphatic or aromatic hydrocarbon moieties optionally linked through a divalent oxygen or sulfur atom, amino groups, amido groups, sulfonamido groups, sulfamoyl groups, ureido groups, thioureido groups, hydroxy groups, —C(O)M groups, and —S(O)$_2$M groups, wherein M is chosen to complete an acid, ester, thioester, or salt.

35. A photographic element according to claim 1 wherein said addendum includes a substituent of said interposed carbon atom of said five membered ring capable of providing a favored reaction site.

36. A photographic element according to claim 35 wherein said substituent is linked to said interposed carbon atom by a single or double carbon to carbon or carbon to nitrogen bond or a carbon to chalcogen bond.

37. A photographic element according to claim 36 wherein said substituent is chosen from among an aliphatic or aromatic hydrocarbon moiety optionally linked through a divalent oxy, thio, or carbonyl linkage, an imino group, an amino group, an amido group, a ureido group, a formamidine disulfide group, or a —C(O)M group, wherein M is chosen to complete an acid, ester, thioester, or salt.

38. A photographic element according to claim 33 wherein said benzotellurazole or naphthotellurazole include a hydrocarbon moiety bonded to said interposed carbon atom.

39. A photographic element according to claim 38 wherein said hydrocarbon moiety is an alkyl substituent.

40. A photographic element according to claim 39 wherein the benzo or naphtho aromatic ring portion includes at least one substituent chosen from the group consisting of alkyl, alkoxy, alkylthio, and hydroxy.

41. A photographic element according to claim 40 wherein said alkyl moieties contain in each occurrence from 1 to 6 carbon atoms.

42. A photographic element according to claim 41 in which said benzotellurazole or naphthotellurazole is chosen from among
a 2-methylbenzotellurazole,
a 5-hydroxy-2-methylbenzotellurazole,
a 5-methoxy-2-methylbenzotellurazole,
a 5,6-dimethoxy-2-methylbenzotellurazole,
a 2,5-dimethylbenzotellurazole,
a 2,6-dimethylbenzotellurazole,
a 2,5,6-trimethylbenzotellurazole,
a 2-methyl-5-methylthiobenzotellurazole,
a 2-ethylbenzotellurazole,
a 2-methylnaphtho[1,2,d]tellurazole,
a 2,5-dimethylnaphtho[1,2,d]tellurazole, and
a 7-methoxy-2-methylnaphtho[1,2,d]tellurazole.

43. A photographic element according to claim 1 in which said addendum is a heterocyclic ammonium salt containing an aromatic ring and, fused with said aromatic ring, a tellurazolinium or tellurazolium ring containing a protonated or quaternized nitrogen atom.

44. A photographic element including a heterocyclic ammonium salt according to claim 43 which is a benzotellurazolium or naphthotellurazolium salt.

45. A photographic element including a heterocyclic ammonium salt according to claim 44 including a carbon to nitrogen bond joining a quaternizing substituent to said ring nitrogen atom.

46. A photographic element including a heterocyclic quaternary ammonium salt according to claim 45 wherein said quaternizing substituent is comprised of an optionally substituted hydrocarbon moiety.

47. A photographic element including a heterocyclic quaternary ammonium salt according to claim 46 wherein said hydrocarbon moiety is substituted with an oxy, thio, sulfo, sulfonyl, sulfato, or carboxy group or or a halogen atom.

48. A photographic element including a heterocyclic quaternary ammonium salt according to claim 47 wherein said hydrocarbon moiety is an alkyl moiety.

49. A photographic element including a heterocyclic quaternary ammonium salt according to claim 47 wherein said said alkyl moiety contains from 1 to 6 carbon atoms.

50. A photographic element including a heterocyclic quaternary ammonium salt according to claim 46 wherein said quaternizing substituent is a sulfoalkyl or sulfatoalkyl radical.

51. A photographic element including a heterocyclic quaternary ammonium salt according to claim 45 wherein said quaternizing substituent is comprised of an alkynyl radical.

52. A photographic element including a heterocyclic quaternary ammonium salt according to claim 51 wherein said alkynyl radical contains from 3 to 5 carbon atoms.

53. A photographic element including a heterocyclic quaternary ammonium salt according to claim 52 wherein said alkynyl radical is a propargyl or 2-butynyl radical.

54. A photographic element including a heterocyclic quaternary ammonium salt according to claim 45 wherein said quaternizing substituent is comprised of an alkenyl radical.

55. A photographic element including a heterocyclic quaternary ammonium salt according to claim 54 wherein said alkenyl radical is an allyl radical.

56. A photographic element including a heterocyclic quaternary ammonium salt according to claim 45 wherein said quaternizing substituent is comprised of an aralkyl radical.

57. A photographic element including a heterocyclic quaternary ammonium salt according to claim 56 wherein said aralkyl radical is a benzyl radical.

58. A photographic element including a heterocyclic quaternary ammonium salt according to claim 45 wherein said quaternizing substituent includes an ester linkage.

59. A photographic element including a heterocyclic quaternary ammonium salt according to claim 45 wherein said quaternizing substituent includes a dioxolane ring.

60. A photographic element including a heterocyclic ammonium salt according to claim 43 including bonded to the carbon atom interposed between the tellurium and nitrogen atoms of said tellurazolium ring one of the following: an aliphatic or aromatic hydrocarbon moiety optionally linked through a divalent oxy, thio, or carbonyl linkage, an amino group, an amido group, a ureido group, a formamidine disulfide group, or a —C(O)M group, wherein M is chosen to complete an acid, ester, thioester, or salt.

61. A photographic element including a heterocyclic salt according to claim 60 wherein an amino group or hydrocarbon moiety is bonded to said interposed carbon atom.

62. A photographic element including a heterocyclic salt according to claim 61 wherein an alkyl substituent is bonded to said interposed carbon atom.

63. A photographic element including a heterocyclic salt according to claim 62 wherein said alkyl substituent contains from 1 to 6 carbon atoms.

64. A photographic element according to claim 2 in which said addendum is a dye containing at least one basic nucleus comprised of an aromatic ring and a fused tellurazolium ring.

65. A photographic element according to claim 64 wherein said tellurazolium ring represents one resonance extreme which rearranges to a tellurazolinylidene ring in a second resonance extreme.

66. A photographic element according to claim 65 which is chosen from the class consisting of a cyanine dye, including either a simple or complex cyanine dye, a merocyanine dye, including either a simple or complex merocyanine dye, a hemicyanine dye, a styryl dye, a neocyanine dye, an azacyanine dye, an allopolarcyanine dye, or a diazo dye.

67. A photographic element according to claim 66 in which said dye is a cyanine dye containing in addition to said one basic nucleus including said tellurazolium ring a second basic nucleus joined by a methine linkage.

68. A photographic element according to claim 67 wherein said methine linkage contains from 1 to 13 methine groups.

69. A photographic element according to claim 68 wherein said methine linkage contains from 1 to 5 methine groups.

70. A photographic element according to claim 2 in which said addendum is a cyanine dye of the formula

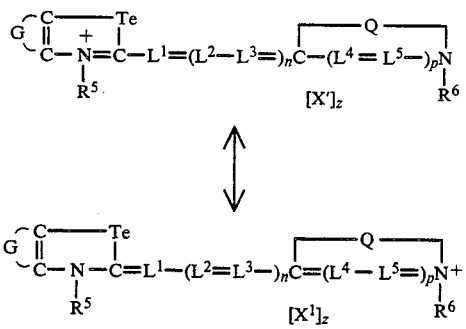

wherein
G represents the atoms completing a fused aromatic nucleus;
$L^1$, $L^2$, $L^3$, $L^4$, and $L^5$ each independently represent a methine group;
n represents zero, 1 or 2;
p represents zero or 1;
Q represents the atoms completing a basic azole or azine heterocyclic nucleus;
$R^5$ and $R^6$ each independently represent a quaternizing substituent;
$X^1$ represents a counterion, and
z is zero or a positive integer chosen to balance ionic charge.

71. A photographic element according to claim 70 wherein G completes a benzo or naphtho fused aromatic nucleus.

72. A photographic element according to claim 71 wherein said benzo or naphtho nucleus includes an electron donating substituent.

73. A photographic element according to claim 71 wherein said benzo or naphtho nucleus includes at least one substituent chosen from among aliphatic or aromatic groups comprised of hydrocarbon moieties optionally linked through a divalent oxygen or sulfur atom, amino groups, amido groups, sulfonamido groups, sulfamoyl groups, ureido groups, thioureido groups, hydroxy groups, —C(O)M groups, and —S(O)$_2$M groups, wherein M is chosen to complete an acid, ester, thioester, or salt.

74. A photographic element according to claim 70 wherein said methine group is a —C(H)=linking group.

75. A photographic element according to claim 74 wherein n is zero.

76. A photographic element according to claim 74 wherein n is 1.

77. A photographic element according to claim 74 wherein n is 2.

78. A photographic element according to claim 74 wherein p is zero.

79. A photographic element according to claim 74 wherein at least one of $R^5$ and $R^6$ is comprised of an optionally substituted hydrocarbon group.

80. A photographic element according to claim 79 wherein $R^5$ is comprised of an alkyl, cycloalkyl, alkenyl, alkynyl, aryl, aralkyl, or alkaryl group.

81. A photographic element according to claim 80 wherein $R^5$ additionally includes an oxy, thio, sulfonyl, sulfato, halo, or carboxy substituent of said hydrocarbon group.

82. A photographic element according to claim 81 wherein $R^5$ is a sulfoalkyl or sulfatoalkyl group.

83. A photographic element according to claim 80 wherein $R^5$ is comprised of an alkyl group which contains from 1 to 6 carbon atoms.

84. A photographic element according to claim 70 wherein Q is chosen from the group consisting of benzotellurazolinylidene, naphthotellurazolinylidene, 2- or 4-pyridylidene, imidazopyridylidene, 2- or 4-quinolinylidene, 1- or 3-isoquinolinylidene, benzoquinolinylidene, thiazoloquinolylidene, imidazoquinolylidene, 3H-indolylidene, 1H or 3H-benzindolylidene, oxazolidinylidene, oxazolinylidene, benzoxazolinylidene, naphthoxazolinylidene, oxadiazolinylidene, thiazolinylidene, phenanthrothiazolinylidene, acenaphthothiazolinylidene, thiazolinylidene, benzothiazolinylidene, naphthothiazolinylidene, tetrahydrobenzothiazolinylidene, dihydronaphthothiazolidinylidene, thiadioxazolinylidene, selenazolinylidene, selenazolidinylidene, benzoselenazolinylidene, naphthoselenazolinylidene, selenadiazolinylidene, pyrazolylidene, imidazolinylidene, imidazolidinylidene, benzimidazolinylidene, naphthimidazolinylidene, diazolinylidene, tetrazolinylidene, and imidazoquinoxalinylidene nuclei.

85. A photographic element according to claim 2 in which said addendum is a cyanine dye of the formula

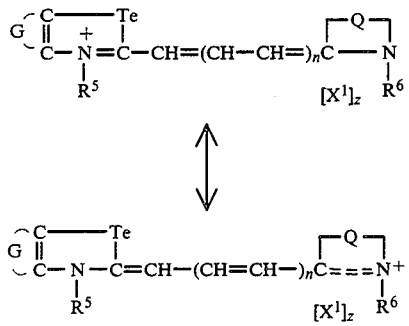

wherein
G completes a fused benzo or naphtho nucleus;
n is zero, 1, or 2;
$R^5$ and $R^6$ are independently alkyl radicals which are optionally sulfo substituted;
Q represents the atoms completing a basic azole or azine nucleus optionally including a fused benzo or naptho ring portion;
$X^1$ is a counterion; and
z is zero or a positive integer chosen to balance ionic charge.

86. A photographic element according to claim 85 wherein said alkyl radicals each contain from 1 to 6 carbon atoms.

87. A photographic element according to claim 85 wherein G completes a fused benzo or naphtho ring portion which includes one or a combination of alkyl, alkoxy, thioalkyl, and hydroxy substituents.

88. A photographic element according to claim 87 wherein said alkyl moieties of said benzo or naphtho ring substituents contain from 1 to 6 carbon atoms.

89. A photographic element according to claim 88 which is a symmetrical cyanine dye.

90. A photographic element according to claim 2 in which said addendum is a cyanine dye of the formula

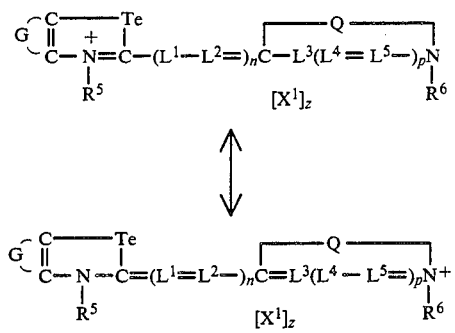

wherein
G represents the atoms completing a fused aromatic nucleus;
$L^1$, $L^2$, $L^3$, $L^4$, and $L^5$ each independently represent a methine group;
n represents zero, 1, or 2;
p represents zero or 1;
Q represents the atoms completing a basic heterocyclic azole or azine nucleus;
$R^5$ and $R^6$ each independently represent a quaternizing substituent;
$X^1$ represents a counterion, and
z is zero or a positive integer chosen to balance ionic chare.

91. A photographic element according to claim 90 wherein G completes a benzo or naphtho fused aromatic nucleus.

92. A photographic elenent according to claim 91 wherein said benzo or naphtho nucleus includes an electron donating subsituent.

93. A photographic element according to claim 91 wherein said benzo or naphtho nucleus includes at least one substituent chosen from among aliphatic or aromatic groups comprised of hydrocarbon moieties optionally linked through a divalent oxygen or sulfur atom, amino groups, amido groups, sulfonamido groups, sulfamoyl groups, ureido groups, thioureido groups, hydroxy groups, —C(O)M groups, and —S-(O)$_2$M groups, wherein M is chosen to complete an acid, ester, thioester, or salt.

94. A photographic element according to claim 90 wherein said methine group is a —C(H)=linking grup.

95. A photographic element according to claim 94 wherein n is zero.

96. A photographic element according to claim 94 wherein n is 1.

97. A photographic element according to claim 94 wherein n is 2.

98. A photographic element according to claim 94 wherein p is zero.

99. A photographic element according to claim 94 wherein at least one of $R^5$ and $R^6$ is comprised of an optionally substitued hydrocarbon group.

100. A photographic element according to claim 99 wherein $R^5$ is comprised of an alkyl, cycloalkyl, alkenyl, alkynyl, aryl, aralkyl, or alkaryl group.

101. A photographic element according to claim 100 wherein $R^5$ additionally includes an oxy, thio, sulfonyl, sulfato, halo, or carboxy substituent of said hydrocarbon group.

102. A photographic element according to claim 101 wherein $R^5$ is a sulfoalkyl or sulfatoalkyl group.

103. A photographic element according to claim 100 wherein $R^5$ is comprised of an alkyl group which contains from 1 to 6 carbon atoms.

104. A photographic element according to claim 90 wherein Q is chosen from the group consisting of pyrrolylidene, indolylidene, carbazolylidene, benzindolylidene, pyrazolylidene, indazolylidene, and pyrrolopyridinylidene nuclei.

105. A dye according to claim 66 which is a merocyanine dye containing in addition to said one basic nucleus including said tellurazolium ring a second, acidic nucleus joined to said basic nucleus directly or through a methine linkage.

106. A photographic element according to claim 105 in which said merocyanine dye is of the formula

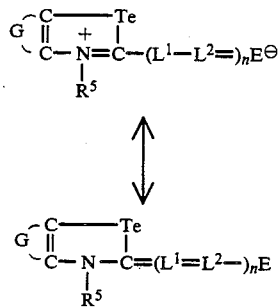

wherein

E represents an acidic nucleus;

G represents the atoms completing a fused aromatic nucleus;

$L^1$ and $L^2$ each independently represent a methine linkage;

n represents zero, 1, or 2; and $R^5$ represents a quaternizing substituent.

107. A photographic element according to claim 106 wherein G completes a benzo or naphtho fused aromatic nucleus.

108. A photographic element according to claim 107 wherein said benzo or naphtho nucleus includes an electron donating substituent.

109. A photographic element according to claim 107 wherein said benzo or naphtho nucleus includes at least one substituent chosen from among aliphatic or aromatic groups comprised of hydrocarbon moieties optionally linked through a divalent oxygen or sulfur atom, amino groups, amido groups, sulfonamido groups, sulfamoyl groups, ureido groups, thioureido groups, hydroxy groups, —C(O)M groups, and —S(O)$_2$M groups, wherein M is chosen to complete an acid, ester, thioester, or salt.

110. A photographic element according to claim 106 wherein said methine linkage is a —C(H)=linking group.

111. A photographic element according to claim 110 wherein n is zero.

112. A photographic element according to claim 110 wherein n is 1.

113. A photographic element according to claim 110 wherein n is 2.

114. A photographic element according to claim 106 wherein $R^5$ is comprised of an optionally substituted hydrocarbon group.

115. A photographic element according to claim 114 wherein $R^5$ is comprised of an alkyl, cycloalkyl, alkenyl, alkynyl, aryl, aralkyl, or alkaryl group.

116. A photographic element according to claim 115 wherein $R^5$ additionally includes an oxy, thio, sulfonyl, sulfato, halo, or carboxy substituent of said hydrocarbon group.

117. A photographic element according to claim 116 wherein $R^5$ is a sulfoalkyl or sulfatoalkyl group.

118. A photographic element according to claim 115 wherein $R^5$ is comprised of an alkyl group which contains from 1 to 6 carbon atoms.

119. A photographic element according to claim 106 wherein E is in one resonance extreme comprised of a methylene moiety bonded to a carbonyl, sulfo, or cyano group directly or through a methine linkage.

120. A photographic element according to claim 119 wherein E satisfies the formula

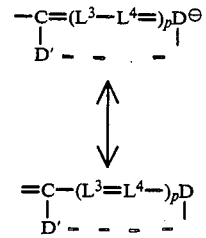

wherein

D is a cyano, sulfo, or carbonyl group,

D' is a methine substituent which can with D complete a five or six membered heterocyclic ring containing ring atoms chosen from the class consisting of carbon, nitrogen, oxygen, and sulfur.

121. A photographic element according to claim 120 wherein D' is a cyano group.

122. A photographic element according to claim 120 wherein D and D' together complete a 2-pyrazolin-5-one, pyrazolidene-3,5-dione, imidazoline-5-one, hydantoin, 2 or 4-thiohydantoin, 2-iminooxazoline-4-one, 2-oxazoline-5-one, 2-thiooxazolidine-2,4-dione, isoxazoline-5-one, 2-thiazoline-4-one, thiazolidine-4-one, thiazolidine-2,4-dione, rhodanine, thiazolidine-2,4-dithione, isorhodanine, indane-1,3-dione, thiophene-3-one, thiophene-3-1,1-dioxide, indoline-2-one, indoline-3-one, indazoline-3-one, 2-oxoindazolinium, 3-oxoindazolinium, 5,7-dioxo-6,7-dihydrothiazolo[3,2-a]pyrimidine, cycylohexane-1,3-dione, 3,4-dihydroisoquinoline-4-one, 1,3-dioxane-4,6-dione, barbituric acid, 2-thiobarbituric acid, chroman-2,4-dione, indazoline-2-one, and pyrido[1,2-a]pyrimidine-1,3-dione.

* * * * *